US011339378B2

(12) United States Patent
Smith et al.

(10) Patent No.: US 11,339,378 B2
(45) Date of Patent: *May 24, 2022

(54) NON-NEUROINVASIVE VIRUSES AND USES THEREOF

(71) Applicants: Northwestern University, Evanston, IL (US); Board of Regents of the University of Nebraska, Lincoln, NE (US); Trustees of Tufts College, Medford, MA (US)

(72) Inventors: Gregory A. Smith, Oak Park, IL (US); Patricia Jane Sollars, Lincoln, NE (US); Gary Edward Pickard, Lincoln, NE (US); Ekaterina E. Heldwein, Belmont, MA (US)

(73) Assignees: Northwestern University, Evanston, IL (US); Board of Regents of the University of Nebraska, Lincoln, NE (US); Trustees of Tufts College, Medford, MA (US)

( * ) Notice: Subject to any disclaimer, the term of this patent is extended or adjusted under 35 U.S.C. 154(b) by 54 days.

This patent is subject to a terminal disclaimer.

(21) Appl. No.: 16/868,246

(22) Filed: May 6, 2020

(65) Prior Publication Data
US 2020/0263147 A1 Aug. 20, 2020

Related U.S. Application Data

(63) Continuation of application No. 15/555,873, filed as application No. PCT/US2016/020960 on Mar. 4, 2016, now Pat. No. 10,647,964.

(60) Provisional application No. 62/128,613, filed on Mar. 5, 2015.

(51) Int. Cl.
| *A61K 35/763* | (2015.01) |
| *C12N 7/00* | (2006.01) |
| *C07K 14/005* | (2006.01) |
| *A61K 39/12* | (2006.01) |
| *A61K 39/245* | (2006.01) |
| *A61K 39/25* | (2006.01) |
| *A61K 39/00* | (2006.01) |

(52) U.S. Cl.
CPC .............. *C12N 7/00* (2013.01); *A61K 35/763* (2013.01); *A61K 39/12* (2013.01); *A61K 39/245* (2013.01); *A61K 39/25* (2013.01); *C07K 14/005* (2013.01); *A61K 2039/5254* (2013.01); *C07K 2299/00* (2013.01); *C12N 2710/16034* (2013.01); *C12N 2710/16621* (2013.01); *C12N 2710/16622* (2013.01); *C12N 2710/16632* (2013.01); *C12N 2710/16633* (2013.01); *C12N 2710/16634* (2013.01); *C12N 2710/16643* (2013.01); *C12N 2710/16721* (2013.01); *C12N 2710/16722* (2013.01); *C12N 2710/16732* (2013.01); *C12N 2710/16733* (2013.01); *C12N 2710/16734* (2013.01); *C12N 2710/16743* (2013.01)

(58) Field of Classification Search
CPC .................. A61K 39/245; C12N 15/86; C12N 2760/16134; C12N 2750/14143; C12N 2710/16034
See application file for complete search history.

(56) References Cited

U.S. PATENT DOCUMENTS

| 10,647,964 B2 * | 5/2020 | Smith .................... A61K 39/25 |
| 2005/0003342 A1 | 1/2005 | Poynter |

FOREIGN PATENT DOCUMENTS

| WO | 2012061637 A2 | 5/2012 |
| WO | 2014114691 | 7/2014 |

OTHER PUBLICATIONS

Antinone SE, Shubeita GT, Coller KE, Lee JI, Haverlock-Moyns S, Gross SP, Smith GA. 2006. The herpesvirus capsid surface protein, VP26, and the majority of the tegument proteins are dispensable for capsid transport toward the nucleus. J. Virol. 80:5494-5498.
Bucks et al. (Virology 2007, vol. 361 (2), pp. 316-324.
Bucks MA, Murphy MA, O'Regan KJ, Courtney RJ. 2011. Identification of interaction domains within the UL37 tegument protein of herpes sim-plex virus type 1. Virology 416:42-53.
Copeland AM, Newcomb WW, Brown JC. 2009. Herpes simplex virus replication: roles of viral proteins and nucleoporins in capsid-nucleus attachment. J. Virol. 83:1660-1668.
David, Andrew T. et al. "A Herpes Simplex Virus 1 (McKrae) Mutant Lacking the Glycoprotein K Gene Is Unable to Infect via Neuronal Axons and Egress from Neuronal Cell Bodies." mBio 3.4 (2012): e00144-12. PMC.
Desai P, Sexton GL, Huang E, Person S. 2008. Localization of herpes simplex virus type 1 UL37 in the Golgi complex requires UL36 but not capsid structures. J. Virol. 82:11354-11361.
Desai P, Sexton GL, McCaffery JM, Person S. A null mutation in the gene encoding the herpes simplex virus type 1 UL37 polypeptide abrogates virus maturation. J Virol. Nov. 2001;75(21):10259-71.
Desai PJ. 2000. A null mutation in the UL36 gene of herpes simplex virus type 1 results in accumulation of unenveloped DNA-filled capsids in the cytoplasm of infected cells. J. Virol. 74:11608-11618.
Fuchs W, Klupp BG, Granzow H, Mettenleiter TC. 2004. Essential function of the pseudorabies virus UL36 gene product is independent of its interaction with the UL37 protein. J. Virol. 78:11879-11889.
International Search Report and Written Opinion for PCT Application No. PCT/US2016/020960 dated Aug. 12, 2016.

(Continued)

*Primary Examiner* — Bao Q Li
(74) *Attorney, Agent, or Firm* — Quarles & Brady, LLP; Tambryn Vanheyningen

(57) ABSTRACT

Provided herein are compositions and methods for vaccination and research applications. In particular, provided herein are non-neuroinvasive herpesviruses and alpha herpesviruses and uses thereof.

26 Claims, 16 Drawing Sheets

Specification includes a Sequence Listing.

(56) References Cited

OTHER PUBLICATIONS

Kelly BJ, Mijatov B, Fraefel C, Cunningham AL, Diefenbach RJ. 2012. Identification of a single amino acid residue which is critical for the interaction between HSV-1 inner tegument proteins pUL36 and pUL37. Virology 422:308-316.

Klopfleisch, R et al. Influence of Tegument Proteins of Pseudorabies Virus on Neuroinvasion and Transneuronal Spread in the Nervous System of Adult Mice after Intranasal Inoculation. Journal of Virology. Mar. 2004; vol. 78, No. 6; pp. 2956-2966; abstract; p. 2957, second column, paragraph 6; p. 2961, second column, paragraphs 4-5; DOI: 10.1128/JVI.78.6.2956-2966.2004.

Klupp BG, Fuchs W, Granzow H, Nixdorf R, Mettenleiter TC. 2002, Pseudorabies virus UL36 tegument protein physically interacts with the UL37 protein. J. Virol. 76:3065-3071.

Klupp BG, Granzow H, Mundt E, Mettenleiter TC. Pseudorabies virus UL37 gene product is involved in secondary envelopment. J Virol. Oct. 2001;75(19):8927-36.

Ko DH, Cunningham AL, Diefenbach RJ. 2010. The major determinant for addition of tegument protein pUL48 (VP16) to capsids in herpes simplex virus type 1 is the presence of the major tegument protein pUL36 (VPI/2). J. Virol. 84:1397-1405.

Krautwald M, Fuchs W, Klupp BG, Mettenleiter TC. Translocation of incoming pseudorabies virus capsids to the cell nucleus is delayed in the absence of tegument protein pUL37. J Virol. Apr. 2009;83(7):3389-96.

Lee JH, Vittone V, Diefenbach E, Cunningham AL, Diefenbach RJ. 2008. Identification of structural protein-protein interactions of herpes simplex virus type 1. Virology 378:347-354.

Leege T, Granzow H, Fuchs W, Klupp BG, Mettenleiter TC. 2009. Phenotypic similarities and differences between UL37-deleted pseudorabies virus and herpes simplex virus type 1. J. Gen. Virol. 90:1560-1568.

Lulla, V et al. Presentation Overrides Specificity: Probing the Plasticity of Alphaviral Proteolytic Activity through Mutational Analysis. Journal of Virology. Jul. 17, 2013; vol. 87, No. 18; pp. 10207-10220; p. 10209, first column, paragraph 2; DOI: 10.1128/JVI.01485-13.

Luxton GW, Haverlock S, Coller KE, Antinone SE, Pincetic A, Smith GA. 2005. Targeting of herpesvirus capsid transport in axons is coupled to association with specific sets of tegument proteins. Proc. Natl. Acad. Sci. U.S. A. 102:5832-5837.

Luxton GW, Lee JI, Haverlock-Moyns S, Schober JM, Smith GA. 2006. The pseudorabies virus VPI/2 tegument protein is required for intracellular capsid transport. J. Virol. 80:201-209.

McElwee M, Beilstein F, Labetoulle M, Rixon FJ, Pasdeloup D. 2013. Dystonin/BPAGI promotes plus-end-directed transport of herpes simplex virus 1 capsids on microtubules during entry. J. Virol. 87:11008-11018.

Mettenleiter TC, Klupp BG, Granzow H. 2009. Herpesvirus assembly: an update. Virus Res. 143:222-234.

Newcomb WW, Brown JC. 2010. Structure and capsid association of the herpesvirus large tegument protein UL36. J. Virol. 84:9408-9414.

Pasdeloup D, Beilstein F, Roberts AP, McElwee M, McNab D, Rixon FJ. 2010. Inner tegument protein pUL37 of herpes simplex virus type 1 is involved in directing capsids to the trans-Golgi network for envelopment. J. Gen. Virol. 91:2145-2151.

Pasdeloup D, McElwee M, Beilstein F, Labetoulle M, Rixon FJ. 2013. Herpesvirus tegument protein pUL37 interacts with dystonin/BPAGI to promote capsid transport on microtubules during egress. J. Virol. 87:2857-2867.

Pietzsch, J et al. Human anti-HIV-neutralizing Antibodies Frequently Target a Conserved 7 Epitope Essential for Viral Fitness. The Journal of Experimental Medicine. Aug. 2, 2010; vol. 207, No. 9; pages.

Pitts, Klabis, Richards, Smith, Heidwein . Crystal structure of the herpesvirus inner tegument protein UL37 supports its essential role in control of viral trafficking. J Virol. May 2014;88(10):5462-73.

Roberts AP, Abaitua F, O'Hare P, McNab D, Rixon FJ, Pasdeloup D. 2009. Differing roles of inner tegnment proteins pUL36 and pUL37 during entry of herpes simplex virus type 1. J. Virol. 83:105-116.

Rozen R, Sathish N, Li Y, Yuan Y. 2008. Virion-wide protein interactions of Kaposi's sarcoma-associated herpesvirus. J. Virol. 82:4742-4750.

Ryan SD, Bhanot K, Ferrier A, De Repentigny Y, Chu A, Blais A, Kothary R. 2012. Microtubule stability, Golgi organization, and transport flux require dystonin-a2-MAP1B interaction. J. Cell Biol. 196:727-742.

Sandbaumhuter M, Dohner K, Schipke J, Binz A, Pohlmann A, Sodeik B, Bauerfeind R. 2013. Cytosolic herpes simplex virus capsids not only require binding inner tegnment protein pUL36 but also pUL37 for active transport prior to secondary envelopment. Cell. Microbial. 15:248-269.

Schmitz JB, Albright AG, Kinchington PR, Jenkins FJ. The UL37 protein of herpes simplex virus type 1 is associated with the tegument of purified virions. Virology. Feb. 1, 1995;206(2):1055-65.

Shanda SK, Wilson DW. 2008. UL36p is required for efficient transport of membrane-associated herpes simplex virus type 1 along microtubules. J. Virol. 82:7388-7394.

Stellberger T, Hauser R, Baiker A, Pothineni VR, Haas J, Uetz P. 2010. Improving the yeast two-hybrid system with permutated fusions proteins: the varicella zoster virus interactome. Proteome Sci. 8:8.

To A, Bai Y, Shen A, Gong H, Umamoto S, Lu S, Liu F. 2011. Yeast two hybrid analyses reveal novel binary interactions between human cytomegalovirus-encoded virion proteins. PLoS One 6:e17796.

Vittone V, Diefenbach E, Triffett D, Douglas MW, Cunningham AL, Diefenbach RJ. 2005. Determination of interactions between tegument proteins of herpes simplex virus type 1. J. Virol. 79:9566-9571.

Watanabe D, Ushijima Y, Goshima F, Takakuwa H, Tomita Y, Nishiyama Y. 2000. Identification of nuclear export signal in UL37 protein of herpes simplex virus type 2. Biochem. Biophys. Res. Commun. 276:1248-1254.

Xia, D et cil. Vciricella-Zoster Virus Open Reading Frame 21, Which Is Expressed during Latency, Is Essential for Virus Replication but Dispensable for F.stablishment of Latency. Journal of Virology. Jan. 2003; vol. 77, No. 2; pp. 1211-1218.

\* cited by examiner

NON-NEUROINVASIVE VIRUSES AND USES THEREOF

CROSS REFERENCE TO RELATED APPLICATIONS

The present Application is a Continuation Application of U.S. patent application Ser. No. 15/555,873, filed Sep. 5,2017, and issued as U.S. Pat. No. 10,647,964 on May 12, 2020, which is national stage filing under 35 U.S.C. 371 of International Application No. PCT/US2016/020960, filed Mar. 4, 2016, which claims priority to U.S. Provisional Patent Application Ser. No. 62/128,613 filed Mar. 5, 2015, all of which are herein incorporated by reference in their entirety.

GOVERNMENT SUPPORT

This invention was made with government support under R01 A1056346 and OD001996 both of which were awarded by the National Institutes of Health. The government has certain rights in the invention.

REFERENCE TO SEQUENCE LISTING SUBMITTED VIA EFS-WEB

This application is being filed electronically via EFS-Web and includes an electronically submitted Sequence Listing in .txt format. The .txt file contains a sequence listing entitled "2016-03-04_5369-00332_Sequence_Listing.txt" created on Mar. 4, 2016 and is 76 kilobytes in size. The Sequence Listing contained in this .txt file is part of the specification and is hereby incorporated by reference herein in its entirety.

Please inset the Sequence Listing, enclosed herewith, immediately after the Abstract.

FIELD OF THE DISCLOSURE

Provided herein are compositions and methods for vaccination and research applications. In particular, provided herein are non-neuroinvasive herpesviruses and alpha herpesviruses and uses thereof.

BACKGROUND OF THE DISCLOSURE

Alphaherpesviruses are neuroinvasive pathogens of humans and livestock. All cause a range of disease manifestations from mild to severe, establish life-long infections by invading and residing in the nervous system, and once infected there is no cure.

Of the three human pathogens, varicella zoster virus (VZV) and herpes simplex virus type 1 (HSV-1) and type 2 (HSV-2), there is a vaccine only for VZV. The VZV vaccine is a live-attenuated virus that retains full neuroinvasive properties.

Additional vaccines for alphaherpesviruses are needed, preferably utilizing viruses without neuroinvasive properties.

SUMMARY OF THE DISCLOSURE

Provided herein are compositions and methods for vaccination and research applications. In particular, provided herein are non-neuroinvasive herpesviruses and alpha herpesviruses and uses thereof.

For example, in some embodiments, the present disclosure provides a non-neuroinvasive herepsvirus or alphaherpesvirus (e.g., HSV-1, HSV-2, PRV, VZV, BHV, or EHV). In some embodiments, the UL37 protein of the virus has at least 70% (e.g., at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, or 97%) sequence identity to a sequence selected, for example, SEQ ID NOS: 22-36.

In some embodiments, the virus comprises one or more mutations in the neuroinvasive (R2) domain. Examples include, for example, a variant herpes simplex virus 1 or 2 particle comprising a mutant UL37 protein, wherein said mutant UL37 protein comprises one or more mutations selected from Q403A, E452A, Q455A, Q511A, or R515A; a variant varicella zoster virus particle comprising a mutant UL37 protein, wherein said mutant UL37 protein comprises one or more mutations selected from Q363A, D413A, Q416A, Q472A, or R476A; and a variant pseudorabies virus particle comprising a mutant UL37 protein, wherein said mutant UL37 protein comprises one or more mutations selected from Q324A, D362A, R365A, H421A, or H425A. In some embodiments, the one or more mutations is two or more (e.g., three, four, or all) of the mutations. In some embodiments, the virus particle exhibits reduced neuroinvasiveness relative to a virus particle lacking the mutations. In some embodiments, the virus is avirulent.

Further embodiments provide a nucleic acid or vector encoding the virus particles described herein.

Additional embodiments provide a pharmaceutical composition or vaccine composition comprising the virus particle, nucleic acid, or vector described herein and a pharmaceutically acceptable carrier. In some embodiments, the composition further comprises an adjuvant.

Still other embodiments provide a method of inducing an immune response against a virus, comprising: administering the composition described herein to a subject under conditions such that said subject generates an immune response to the virus. In some embodiments, the subject exhibits immunity to the virus.

Yet other embodiments provide the use of the compositions described herein to generate an immune response against a virus in a subject.

Certain embodiments provide method of preventing infection by a virus, comprising: administering the compositions described herein to a subject under conditions such that the subject generates an immune response to the virus and is immune to infection by the virus. In some embodiments, the subject is human or a non-human animal (e.g., bovine, equine, companion animal, livestock, etc.).

In some embodiments, the present disclosure provides the use of the compositions described herein to prevent infection by a virus in a subject.

Still further embodiments provide a method or use of treating or preventing cancer, comprising: administering the composition described herein to a subject diagnosed with cancer under conditions such that the cancer is reduced or eliminated.

Additional embodiments are described herein.

DESCRIPTION OF THE DRAWINGS

FIG. 1 shows UL37N structure. (A) Linear diagram of UL37 constructs expressed. HS, the His6-SUMO tag. (B) Coomassie-stained SDS-polyacrylamide gel showing purified His6-SUMO-tagged UL37 contaminated with the His6-SUMO-tagged UL37N proteolytic cleavage product and purified monodisperse UL37N. (C) Crystal structure of a UL37N monomer shown in two orientations related by a 180-degree rotation around the vertical axis. (D) A close-up view of residue W477 and its surroundings. (E) UL37N domains are shown individually.

Figure 4:
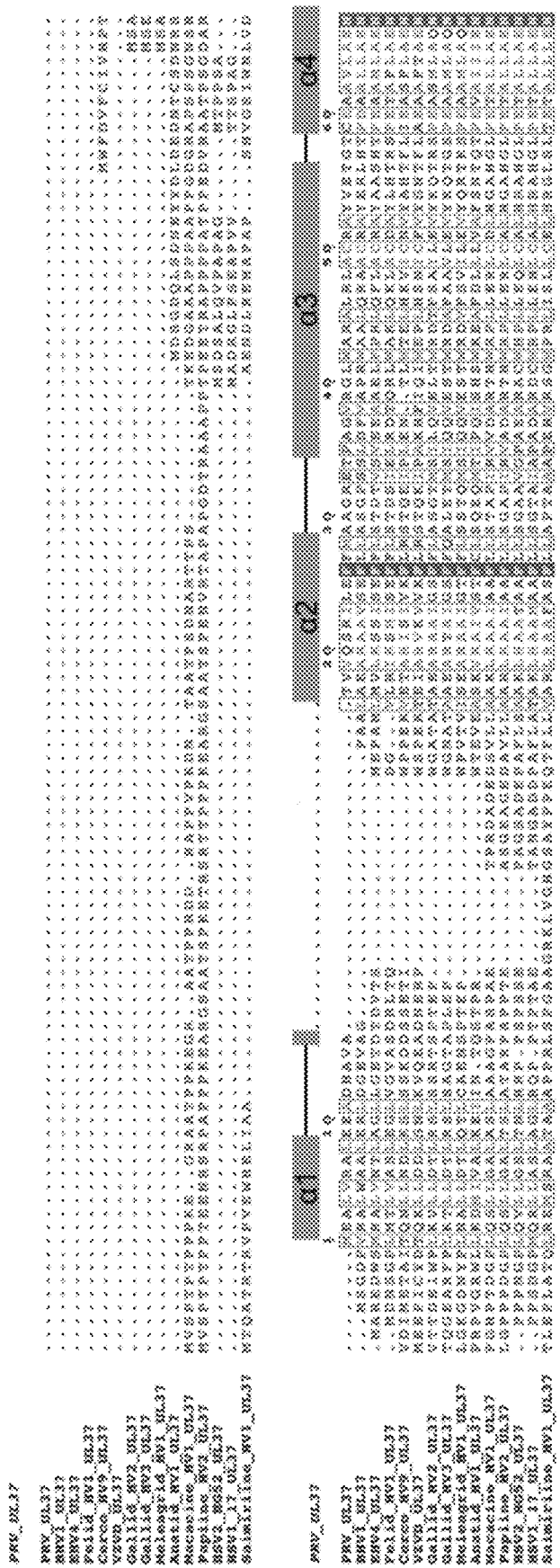
Figure 4:
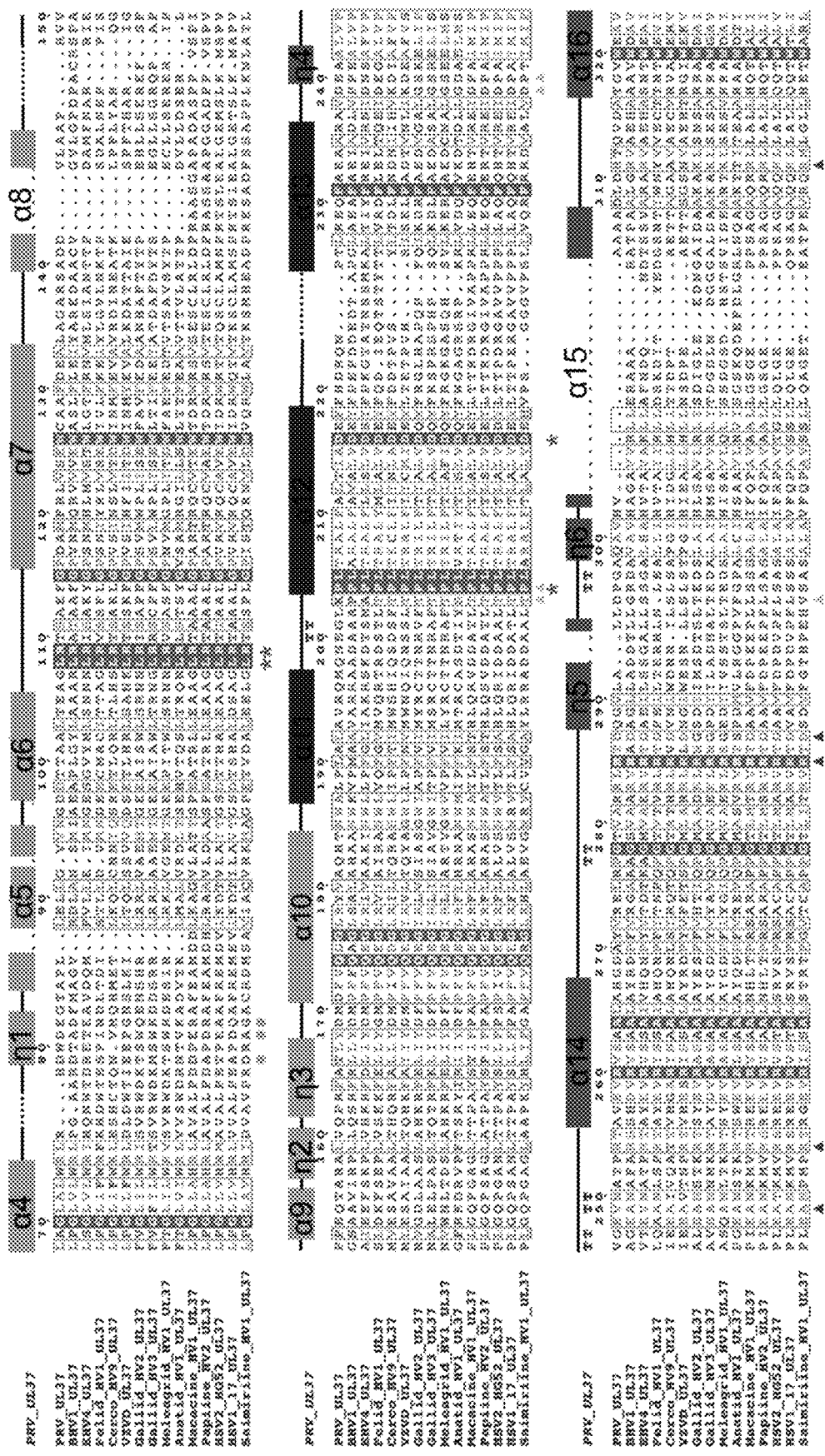
Figure 4:
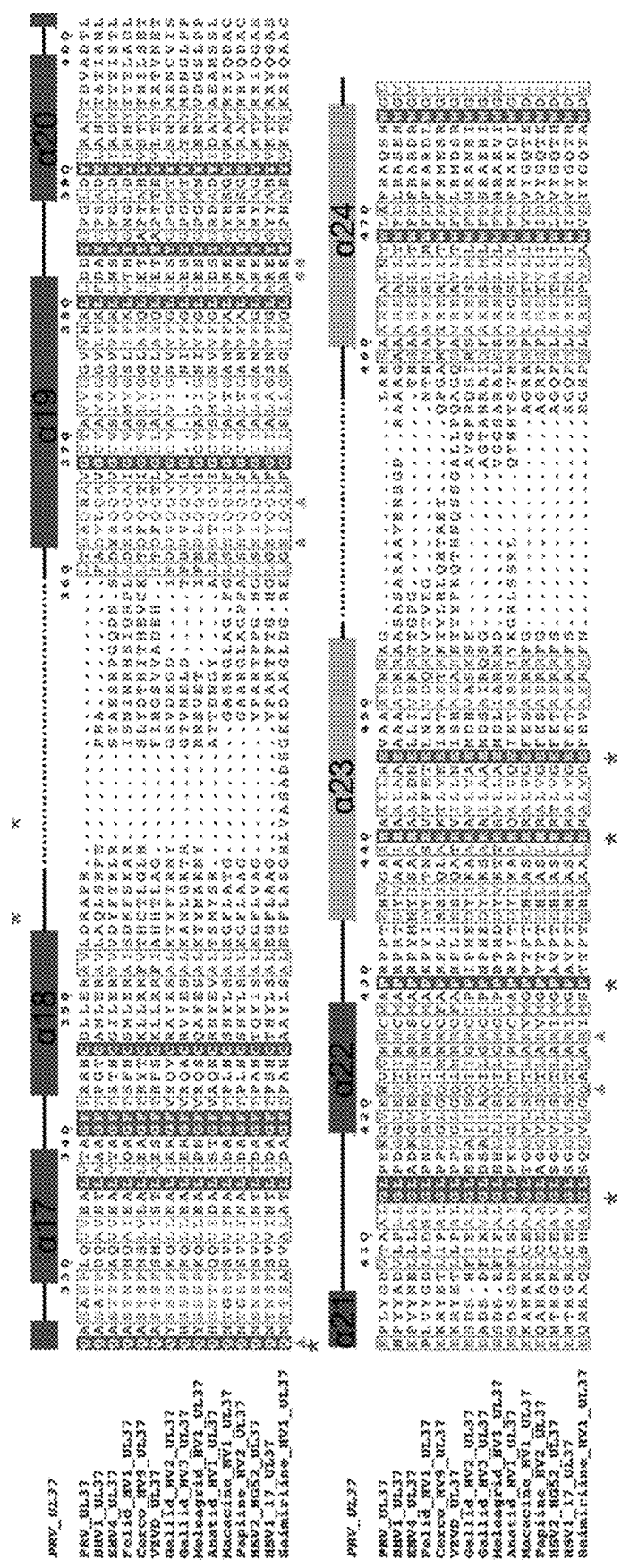

FIG. 4 shows a sequence alignment of 15 UL37 homologs from alphaherpesviruses. The 15 UL37 homologs shown in the alignment are PRV_UL37 (SEQ ID NO: 22), BHV1_UL37 (SEQ ID NO: 23), EHV4_UL37 (SEQ ID NO: 24), Fetid_HV1_UL37 (SEQ ID NO: 25), Cerco_HV9_UL37 (SEQ ID NO: 26), VZVD_UL37 (SEQ ID NO: 27), Gallid_HV2_UL37 (SEQ ID NO: 28), Gallid_HV3_UL37 (SEQ ID NO: 29), Meleagrid_HV1_UL37 (SEQ ID NO: 30), Anatid_HV1_UL37 (SEQ ID NO: 31), Macacine_HV1_UL37 (SEQ ID NO: 32), Papiine_HV2_UL37 (SEQ ID NO: 33), HSV2_HG52_UL37 (SEQ ID NO: 34), HSV1_17_UL37 (SEQ ID NO: 35), Saimiriine_HV1_UL37 (SEQ ID NO: 36).

Figure 5:
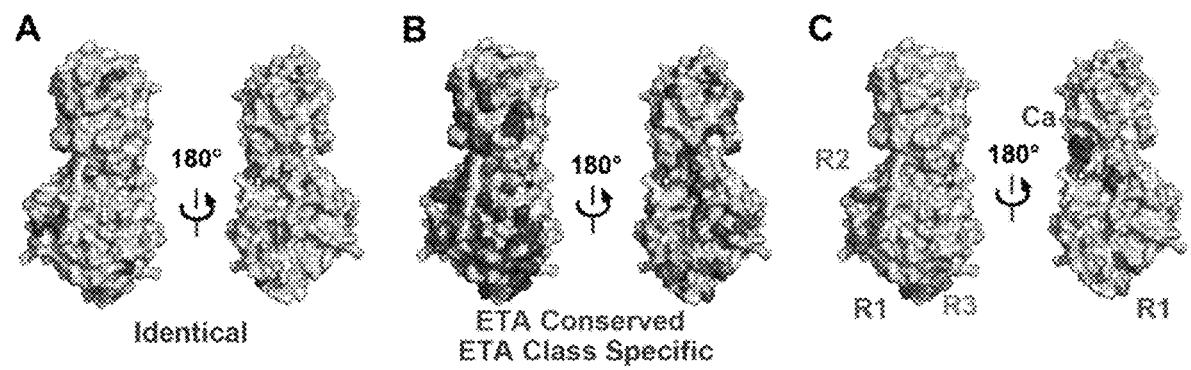

FIG. 5 shows residue conservation on the surface of UL37N. (A) The UL37N structure is shown in surface representation. (B) ETA class conserved and class specific. (C) Mutated residues in R1, R2, R3, and the calcium-binding site (Ca).

Figure 6:
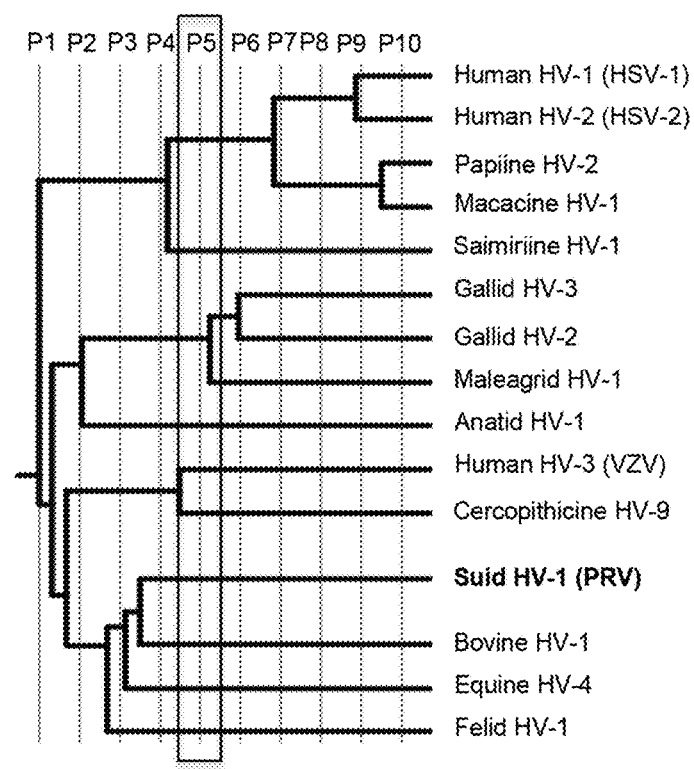

FIG. 6 shows a phylogenetic tree from ETA using UL37 homologs from 15 alphaherpesviruses.

Figure 7:
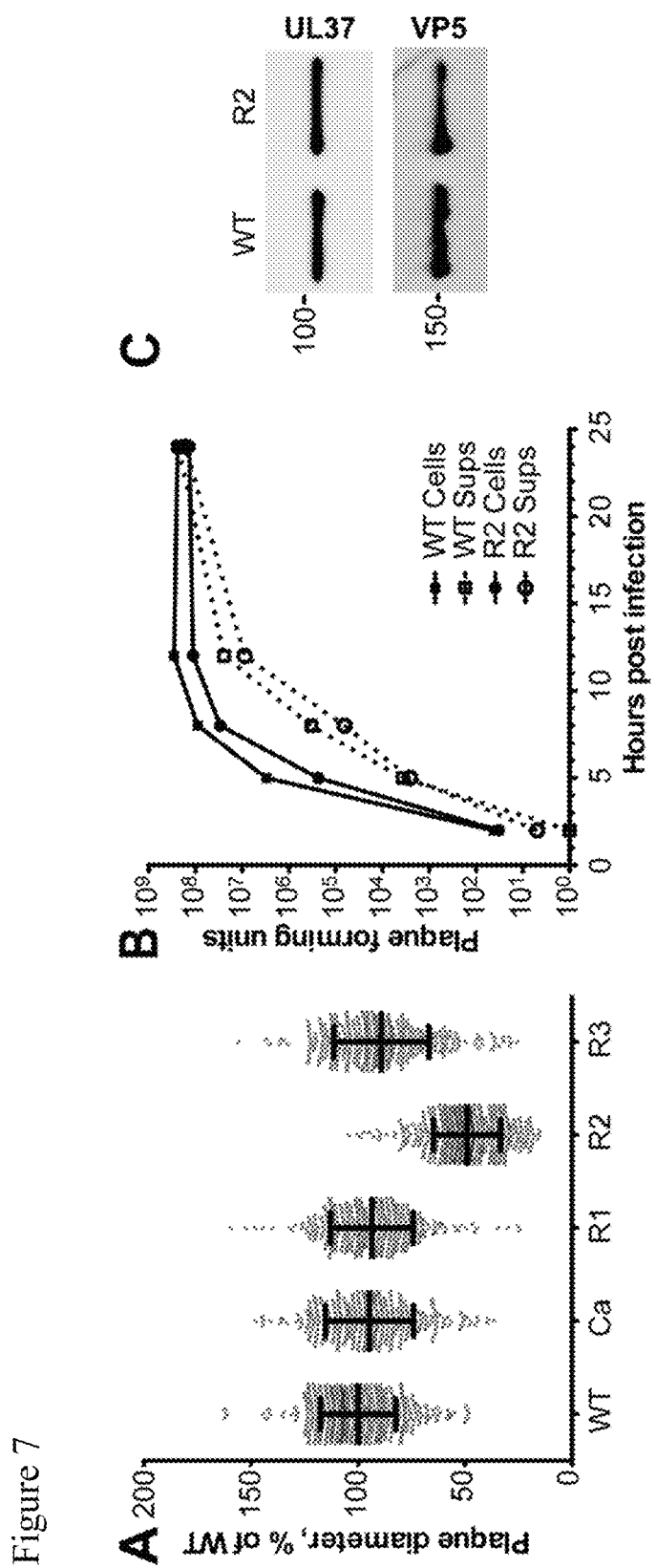

FIG. 7 shows propagation and spread of PRV encoding mutant forms of UL37. (A) Relative plaque diameters of mutant viruses Ca (PRV-GS5476), R1 (PRV-GS5321), R2 (PRV-GS5604), and R3 (PRV-GS5350). (B) Single-step growth curves comparing propagation of PRV-GS4284 (UL37 WT) and PRV-GS5604 (UL37 R2 mutant). (C) Western blot analysis of UL37 protein incorporation into WT and R2 mutant extracellular virions.

Figure 8:
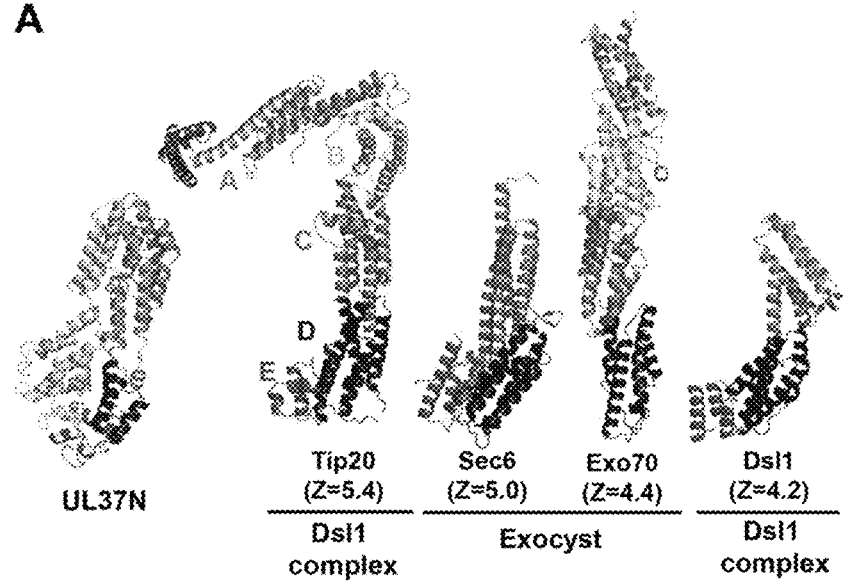
Figure 8:
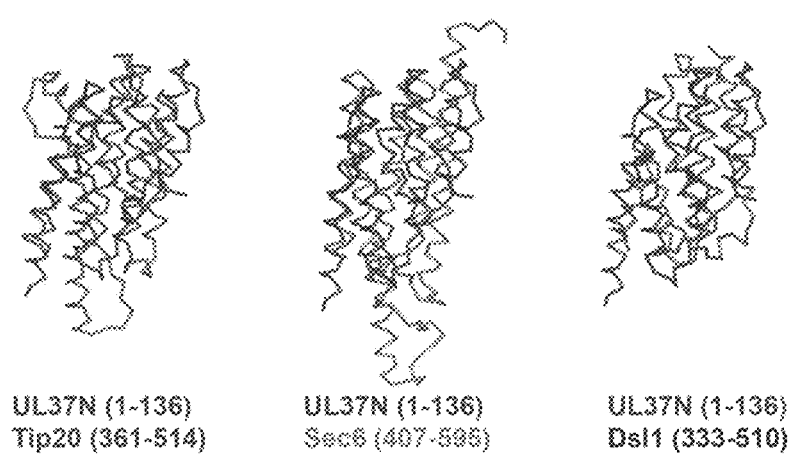
Figure 8:
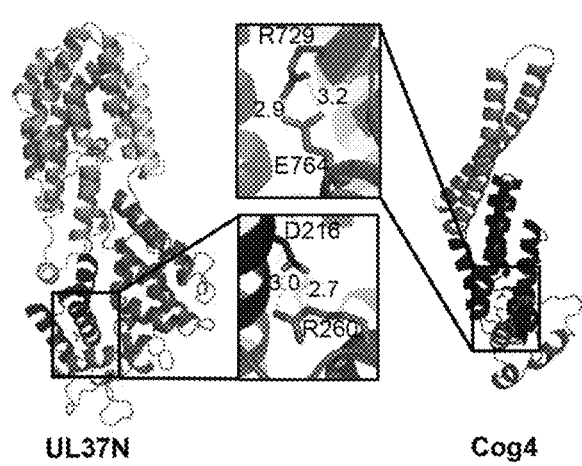
Figure 9:
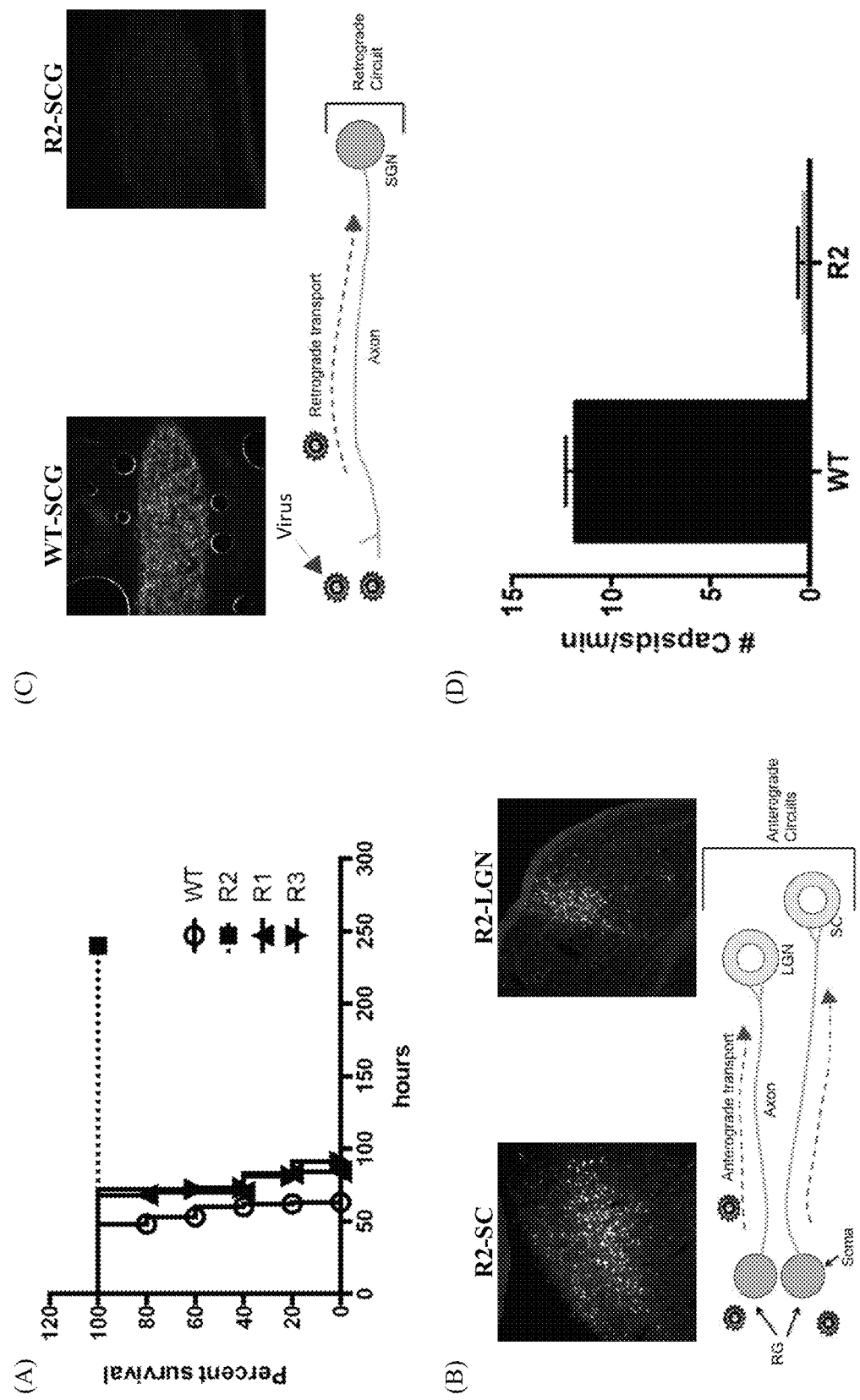

FIG. 8 shows that UL37N shares structural similarities with several subunits of cellular MTCs. (A) UL37N is shown side by side with the Tip20 (PDB accession no. 3FHN) and Dsl1 (PDB accession no. 3K8P) subunits of the Dsl1 complex and the Sec6 (PDB accession no. 2FJI) and Exo70 (PDB accession no. 2B7M) subunits of the exocyst complex, with the Z-score for each alignment displayed. (B) Overlays of regions of Tip20, Sec6, and Dsl1 that align onto residues 1 to 136 of UL37N. (C) The salt bridge in domain II between putative D and E subdomains of UL37N is strictly conserved among FIG. 9 shows characterization of the neuroinvasive properties of the R2 mutant. (A) The R2 region is essential for virulence in a mouse model of infection. (B) The R2 region is essential for retrograde mediated neuroinvasion. (C) The R2 region is dispensable for anterograde spread through neurons. (D) The R2 mutant does not travel retrograde down axons upon infection.

Figure 10:
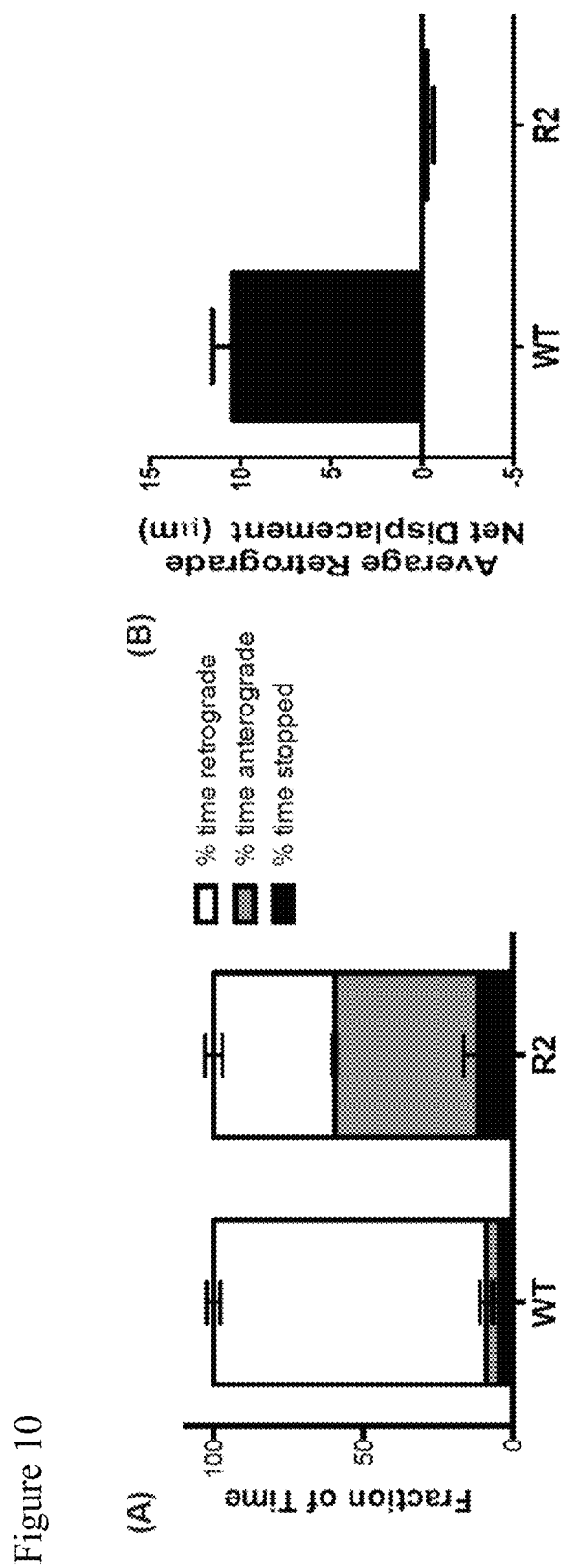
Figure 11:
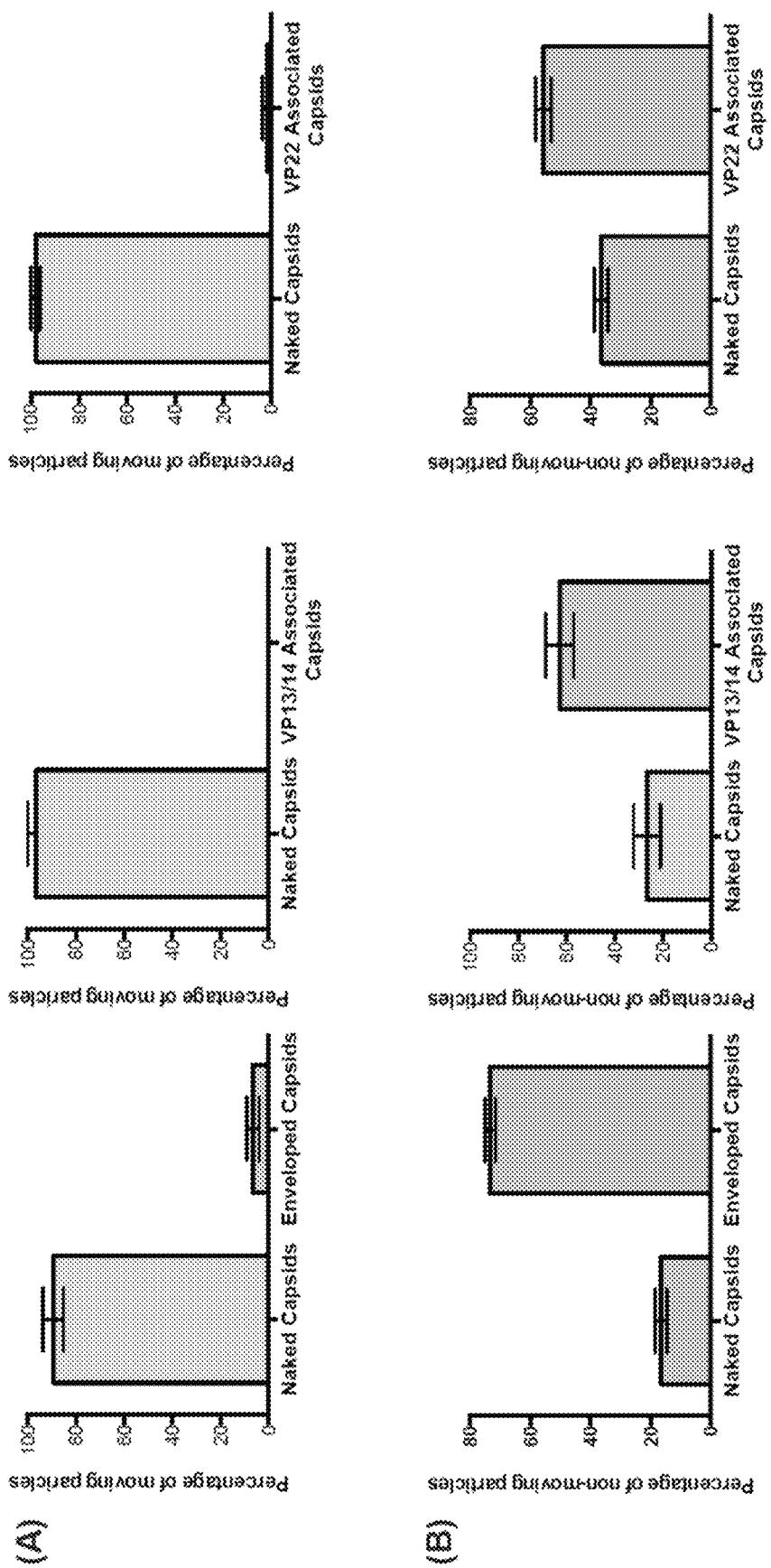

FIG. 10 shows that R2 mutant particles display aberrant non-processive motion. (A) Mutation of the R2 region significantly increases the severity of stop and reversal events. (B) Aberrant motion of R2 mutant particles does not result in overall movement towards the soma FIG. 11 shows that motion of R2 particles does not result from endocytosis of virions or retention of outer tegument proteins following entry. (A) Moving particles are not associated with the gD envelope protein or the outer tegument proteins VP22 and VP13/14. (B) Non-moving particles are predominantly associated with envelope and tegument proteins.

Figure 12:
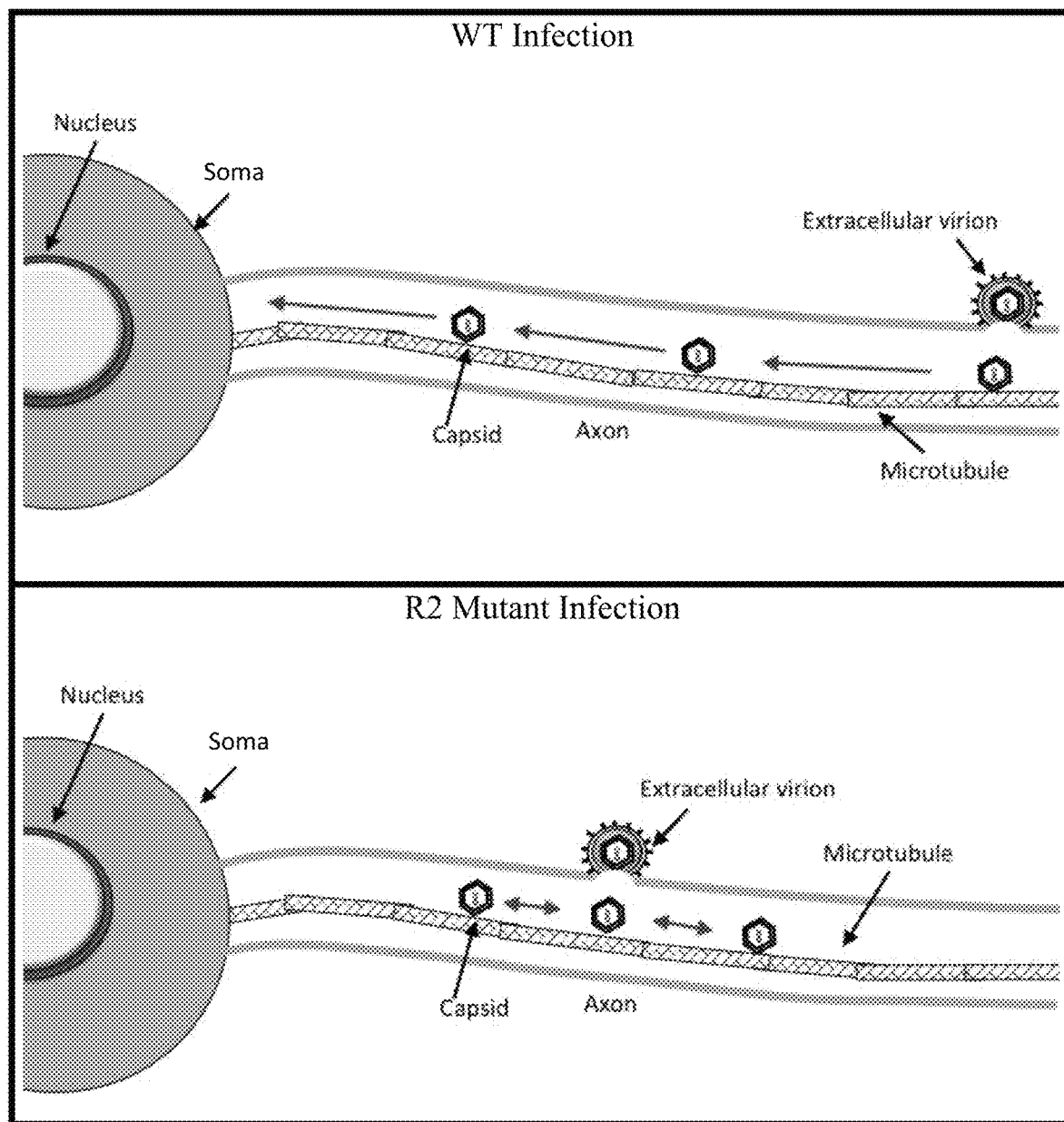

FIG. 12 shows modeling of wild-type and the R2 mutant trafficking in neuronal cells
(Top) Herpesvirus replication occurs in the nucleus, this requires incoming particles to traverse the cytoplasm following entry into the cell. (Bottom) R2 mutant virions fuse with the plasma membrane of the axon however the released capsids alternate between motion towards (retrograde) and away (anterograde) from the soma.

Figure 13:
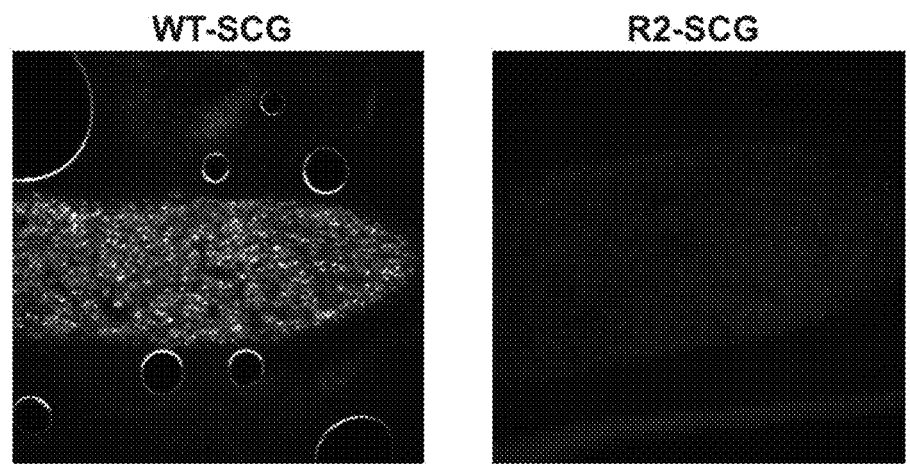

FIG. 13 shows that PRV R2 lacks neuroinvasive properties.

Figure 14:
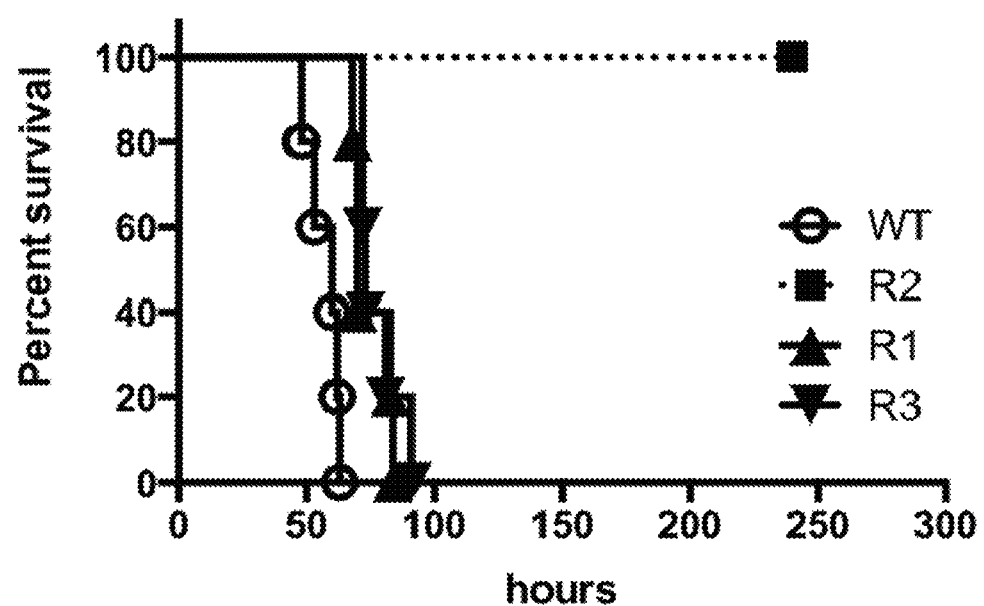

FIG. 14 shows that PRV R2 is avirulent.

Figure 15:
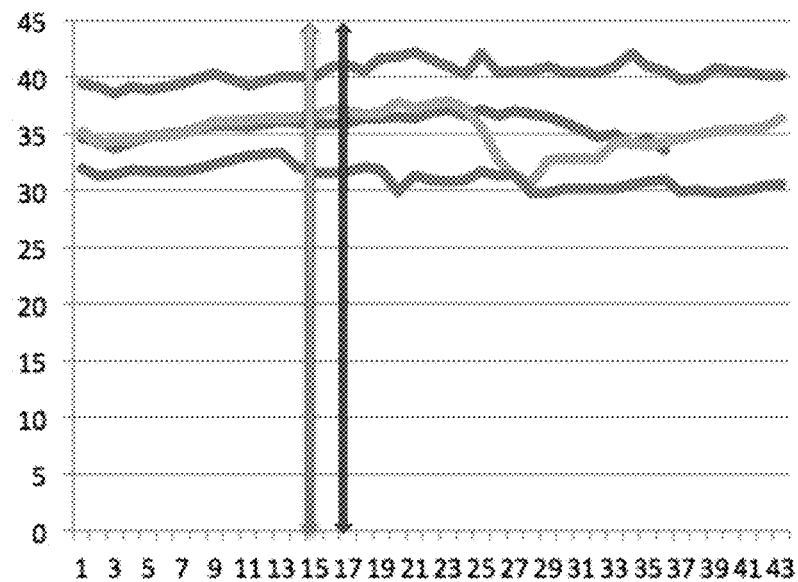

FIG. 15 shows that PRV R2 is a potent live-attenuated vaccine.

Figure 16:
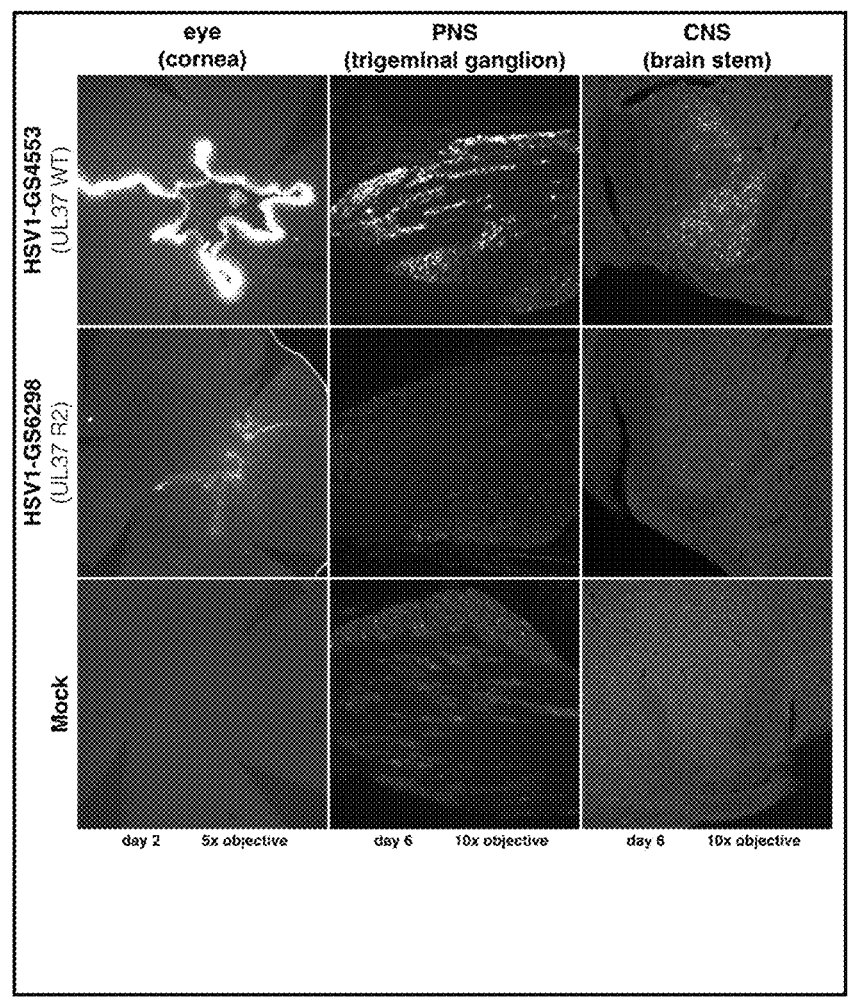

FIG. 16 shows that the HSV-1 R2 mutant (HSV1-GS6298) is incapable of transmitting into the nervous system following replication in the mouse cornea.

Figure 17:
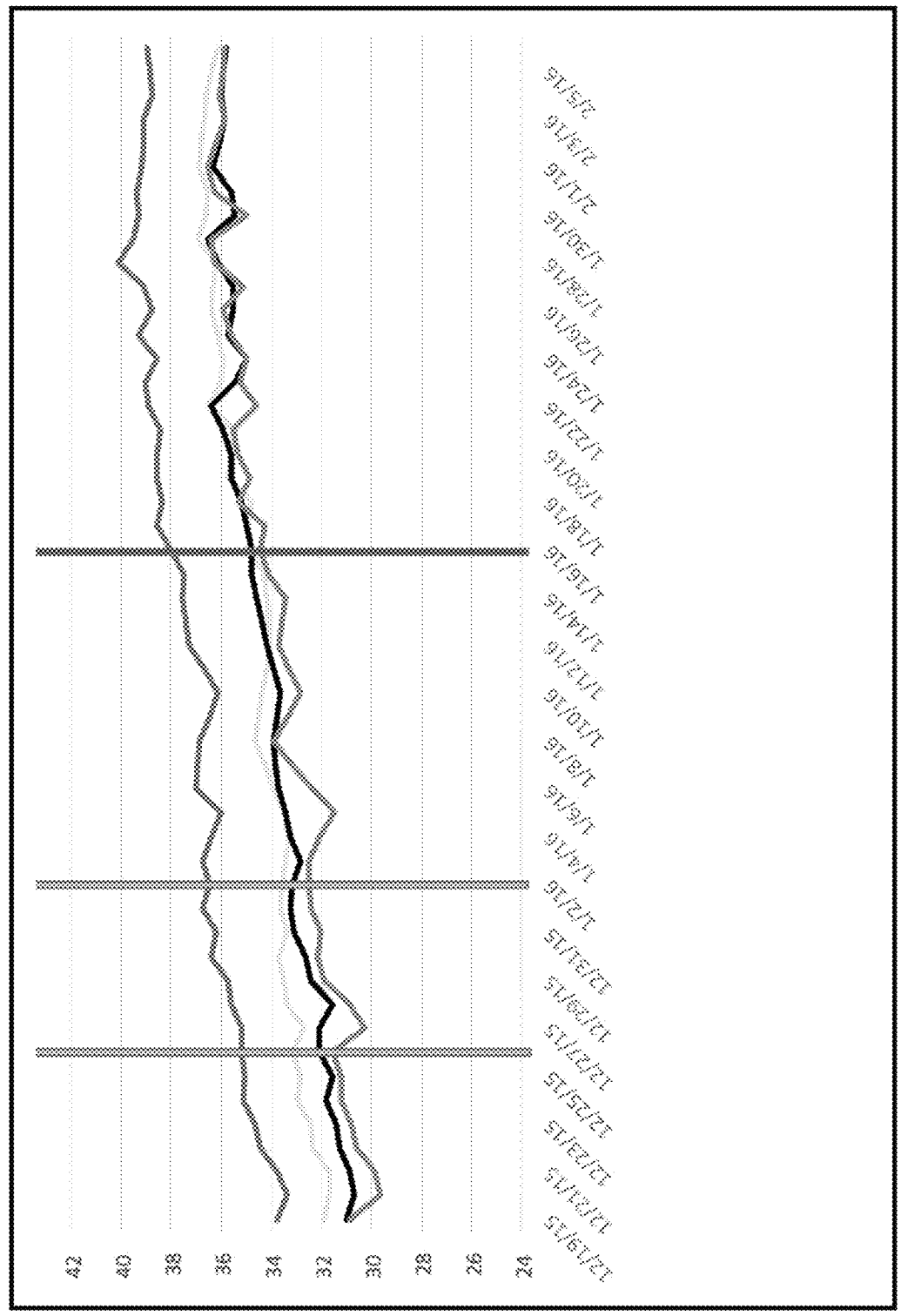

FIG. 17 shows protection of mice from lethal PRV challenge following vaccination with PRV encoding the R2 deletion.

DEFINITIONS

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "co-administration" refers to the administration of at least two agent(s) (e.g., a composition described herein and a anti-viral agent) or therapies to a subject. In some embodiments, the co-administration of two or more agents/therapies is concurrent. In other embodiments, a first agent/therapy is administered prior to a second agent/therapy. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to a molecule which stimulates a response from the adaptive immune system, which may include responses drawn from the group comprising an antibody response, a cytotoxic T cell response, a T helper response, and a T cell memory. An immunogen may stimulate an upregulation of the immune response with a resultant inflammatory response, or may result in down regulation or immunosuppression. Thus the T-cell response may be a T regulatory response. An immunogen also may stimulate a B-cell response and lead to an increase in antibody titer.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the term "peptide" refers to a polymer of two or more amino acids joined via peptide bonds or modified peptide bonds. As used herein, the term "dipeptides" refers to a polymer of two amino acids joined via a peptide or modified peptide bond.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "neuroinvasive" refers to a property of a microorganism (e.g., virus) to enter the nervous system of a subject. In some embodiments, neuroinvasive viruses persist in the nervous system for an extended period of time (e.g., many years to an entire lifetime). In some embodiments, neuroinvasive viruses exhibit periods of dormancy followed by repeat disease.

As used herein, the term "non-neuroinvasive" refers to a virus or other microorganism that lacks neuroinvasive properties.

As used herein, the term "virulent" refers to a microorganism (e.g., virus) that is able to cause disease or symptoms of disease in a subject.

As used herein, the term "avirulent" refers to virus (e.g., variant herpesvirus or alphaherpesvirus of embodiments of the present disclosure) that has reduced or no virulence (e.g., does not cause disease or symptoms of disease).

DETAILED DESCRIPTION OF THE DISCLOSURE

Provided herein are compositions and methods for vaccination and research applications. In particular, provided herein are non-neuroinvasive herpesviruses and alpha herpesviruses and uses thereof.

Alpha-herpesviruses enter the nervous system following initial replication at exposed body surfaces. This neuroinvasive property is a critical step to the establishment of life-long infection. However, this property is un-desirable for clinical applications such as vaccines and cancer therapy.

Accordingly, in some embodiments, the present disclosure provides a non-neuroinvasive herepsvirus or alphaherpesvirus. In some embodiments, the virus comprises one or more mutation in the R2 domain. Examples include, for example, a variant herpes simplex virus 1 or 2 particle comprising a mutant UL37 protein, wherein said mutant UL37 protein comprises one or more mutations selected from Q403A, E452A, Q455A, Q511A, or R515A; a variant varicella zoster virus particle comprising a mutant UL37 protein, wherein said mutant UL37 protein comprises one or more mutations selected from Q363A, D413A, Q416A, Q472A, or R476A; and a variant pseudorabies virus particle comprising a mutant UL37 protein, wherein said mutant UL37 protein comprises one or more mutations selected from Q324A, D362A, R365A, H421A, or H425A. In some embodiments, the one or more mutations is two or more (e.g., three, four, or all) of the mutations. In some embodiments, the virus particle exhibits reduced neuro-invasiveness relative to a virus particle lacking the mutations. In some embodiments, the virus is avirulent.

The present disclosure is not limited to particular herpes or alpha herpes viruses. Examples include, but are not limited to, herpes simplex virus-1 (HSV-1), herpes simplex virus-2 (HSV-2), pseudorabies virus (PRV), varicella-zoster virus (VRV), bovine herpesvirus-1 (BHV-1; causative agent of bovine infectious rhinotracheitis and pustular vulvovaginitis), bovine herpes virus 5 (BHV-5; causative agent of meningoencephalitis and respiratory disease in cattle and sheep); equine herpes virus 1 (EHV-1; causative agent of equine abortions and respiratory disease); equine herpes virus 3 (EHV-3; causative agent of equine coital exanthema); and equine herpes virus 4 (EHV-4; causative agent of equine rhinopneumonitis). Mutations in the R2 domain of the described viruses are identified using the methods described herein (e.g., by homology to PRV and as described in Examples 2-4).

The non-neuroinvasive viruses described herein find use in a variety of research, screening, and therapeutic applications (e.g., for use in preparing vaccine and oncolytic virus compositions).

I. Compositions

In some embodiments, the present disclosure provides vaccine and/or pharmaceutical compositions comprising a variant herpesvirus described herein. The present disclosure is not limited by the particular formulation of a composition. Indeed, a vaccine or pharmaceutical composition of the present disclosure may comprise one or more different agents in addition to the variant herpesvirus. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a vaccine composition comprising a variant herpesvirus comprises an agent and/or co-factor that enhance the ability of the antigen to induce an immune response (e.g., an adjuvant). In some embodiments, the presence of one or more co-factors or agents reduces the amount of antigen required for induction of an immune response (e.g., a protective immune response (e.g., protective immunization)). In some embodiments, the presence of one or more co-factors or agents can be used to skew the immune response towards a cellular (e.g., T cell mediated) or humoral (e.g., antibody mediated) immune response. The present disclosure is not limited by the type of co-factor or agent used in a therapeutic agent of the present disclosure.

Adjuvants are described in general in Vaccine Design—the Subunit and Adjuvant Approach, edited by Powell and Newman, Plenum Press, New York, 1995. The present disclosure is not limited by the type of adjuvant utilized (e.g., for use in a composition (e.g., pharmaceutical composition). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th-type responses (cell-mediated response), and B cell responses (humoral response).

Stimulation of an immune response can result from a direct or indirect response of a cell or component of the immune system to an intervention (e.g., exposure to an antigen or immunogen). Immune responses can be measured in many ways including activation, proliferation or differentiation of cells of the immune system (e.g., B cells; T cells; APCs such as for example dendritic cells and macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

In some embodiments, the present disclosure provides a method of stimulating a Th1-type immune response in a subject comprising administering to a subject a composition comprising a non-neuroinvasive herpes or alphaherpes virus. However, in other embodiments, the present disclosure provides a method of stimulating a Th2-type immune response in a subject (e.g., if balancing of a T cell mediated response is desired) comprising administering to a subject a composition comprising a non-neuroinvasive herpes or alphaherpes virus. In further preferred embodiments, adjuvants can be used (e.g., can be co-administered with a composition of the present disclosure) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present disclosure. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an adjuvant (e.g., Th1-type adjuvant) in a composition of the present disclosure. Saponins are well known adjuvants (See, e.g., Lacaille-Dubois and Wagner (1996) Phytomedicine vol 2 pp 363-386). Examples of saponins include Quil A (derived from the bark of the South American tree *Quillaja saponaria* Molina), and fractions thereof (See, e.g., U.S. Pat. No. 5,057,540; Kensil, Crit Rev Ther Drug Carrier Syst, 1996, 12 (1-2):1-55; and EP 0 362 279, each of which is hereby incorporated by reference in its entirety). Also contemplated to be useful in the present disclosure are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant. CpG is an abbreviation for cytosine-guanosine dinucleotide motifs present in DNA. CpG is known in the art as being an adjuvant when administered by both systemic and mucosal routes (See, e.g., WO 96/02555; EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present disclosure and the present disclosure is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present disclosure for inducing an immune response. In some embodiments, a free solution of CpG is co-administered together with an antigen (e.g., present within a solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. AcadSci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an *E. Coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present disclosure) are used with a composition comprising a non-neuroinvasive herpes or alphaherpes virus of the present disclosure.

Additional examples of adjuvants that find use in the present disclosure include poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Adjuvants may be added to a composition comprising a non-neuroinvasive herpes or alphaherpes virus, or, the adjuvant may be formulated with carriers, for example liposomes, or metallic salts (e.g., aluminium salts (e.g., aluminium hydroxide)) prior to combining with or co-administration with a composition.

In some embodiments, a composition comprising a non-neuroinvasive herpes or alphaherpes virus comprises a single adjuvant. In other embodiments, a composition comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising an antigen or immunogen comprises one or more mucoadhesives (See, e.g., U.S. Pat. App. No. 20050281843, hereby incorporated by reference in its entirety). The present disclosure is not limited by the type of mucoadhesive utilized. Indeed, a variety of mucoadhesives are contemplated to be useful in the present disclosure including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present disclosure and the present disclosure is not limited to any particular mechanism of action, in some embodiments, use of a mucoadhesive (e.g., in a composition comprising a non-neuroinvasive herpes or alphaherpes virus) enhances induction of an immune response in a subject (e.g., administered a composition of the present disclosure) due to an increase in duration and/or amount of exposure to a non-neuroinvasive herpes or alphaherpes virus that a subject experiences when a mucoadhesive is used compared to the duration and/or amount of exposure to a non-neuroinvasive herpes or alphaherpes virus in the absence of using the mucoadhesive.

In some embodiments, a composition of the present disclosure may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium.

For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a variant viral particle of the present disclosure can be used therapeutically (e.g., to enhance an immune response) or as a prophylactic (e.g., for immunization (e.g., to prevent signs or symptoms of disease)) or as an oncolytic virus. A composition can be administered to a subject via a number of different delivery routes and methods.

In some embodiments, compositions of the present disclosure are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), including via cell, vesicles, and liposomes, each of which is hereby incorporated by reference in its entirety). Alternatively, the compositions of the present disclosure may be administered dermally or transdermally, using standard techniques (See, e.g., Remington: The Science and Practice of Pharmacy, Mack Publishing Company, Easton, Pa., 19th edition, 1995). The present disclosure is not limited by the route of administration.

Although an understanding of the mechanism is not necessary to practice the present disclosure and the present disclosure is not limited to any particular mechanism of action, in some embodiments, mucosal vaccination is the preferred route of administration as it has been shown that mucosal administration of antigens has a greater efficacy of inducing protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). More advantageously, in further preferred embodiments, in addition to inducing mucosal immune responses, mucosal vaccination also induces systemic immunity. In some embodiments, non-parenteral administration (e.g., muscosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a non-neuroinvasive herpes or alphaherpes virus of the present disclosure may be used to protect or treat a subject susceptible to, or suffering from, disease by means of administering a composition of the present disclosure via a mucosal route (e.g., an oral/alimentary or nasal route). Alternative mucosal routes include intravaginal and intra-rectal routes. In preferred embodiments of the present disclosure, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition is provided. Enteric formulations such as gastro resistant capsules for oral administration, suppositories for rectal or vaginal administration also form part of this disclosure. Compositions of the present disclosure may also be administered via the oral route. Under these circumstances, a composition comprising a non-neuroinvasive herpes or alphaherpes virus may comprise a pharmaceutically acceptable excipient and/or include alkaline buffers, or enteric capsules. Formulations for nasal delivery may include those with dextran or cyclodextran and saponin as an adjuvant.

Compositions of the present disclosure may also be administered via a vaginal route. In such cases, a composition comprising a non-neuroinvasive herpes or alphaherpes virus may comprise pharmaceutically acceptable excipients and/or emulsifiers, polymers (e.g., CARBOPOL), and other known stabilizers of vaginal creams and suppositories. In some embodiments, compositions of the present disclosure are administered via a rectal route. In such cases, compositions may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response.

For example, in some embodiments, a composition comprising a non-neuroinvasive herpes or alphaherpes virus is administered to a mucosal surface of a subject in either a priming or boosting vaccination regime. Alternatively, in some embodiments, the composition is administered systemically in either a priming or boosting vaccination regime. In some embodiments, a composition is administered to a subject in a priming vaccination regimen via mucosal administration and a boosting regimen via systemic administration. In some embodiments, a composition is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising a non-neuroinvasive herpes or alphaherpes virus may be used for both prophylactic and therapeutic purposes.

In some embodiments, compositions of the present disclosure are administered by pulmonary delivery. For example, a composition of the present disclosure can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colorado; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this disclosure are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this disclosure are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising an variant virus of the present disclosure may be used to protect and/or treat a subject susceptible to, or suffering from, a disease by means of administering the composition by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present disclosure may also be used to enhance the immunogenicity of antigens applied to the skin (transdermal or transcutaneous delivery, See, e.g., WO 98/20734; WO 98/28037, each of which are hereby incorporated by reference).

The present disclosure is not limited by the type of subject administered (e.g., in order to stimulate an immune response (e.g., in order to generate protective immunity (e.g., mucosal and/or systemic immunity) or to target cancer cells) a composition of the present disclosure. Indeed, a wide variety of subjects are contemplated to be benefited from administration of a composition of the present disclosure. In some embodiments, the subject is a human or non-human animal. In some embodiments, human subjects are of any age (e.g., adults, children, infants, etc.) that have been or are likely to become exposed to a microorganism (e.g., herpesvirus). In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present disclosure (e.g., to prevent the occurrence or spread of disease). For example, in some embodiments, compositions and methods of the present disclosure are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits or other animal). In some embodiments, compositions and methods of the present disclosure are utilized in research settings (e.g., with research animals).

A composition of the present disclosure may be formulated for administration by any route, such as mucosal, oral, transdermal, intranasal, intramuscular, parenteral or other route described herein. The compositions may be in any one or more different forms including, but not limited to, tablets, capsules, powders, granules, lozenges, foams, creams or liquid preparations.

Topical formulations of the present disclosure may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl) pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the disclosure, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins. Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present disclosure may be formulated and used as foams. Pharmaceutical foams include formulations such as, but not limited to, emulsions, microemulsions, creams, jellies and liposomes. While basically similar in nature these formulations vary in the components and the consistency of the final product. The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, preferably do not unduly interfere with the biological activities of the components of the compositions of the present disclosure. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the non-neuroinvasive herpes or alpha-herpes virus or other components of the formulation. In some embodiments, immunostimulatory compositions of the present disclosure are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, vaccine compositions are co-administered with one or more antibiotics or antiviral agents. There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

In some embodiments, compositions comprising variant viruses are administered in combination with anti-cancer (e.g., chemotherapy agents). Various classes of antineoplastic (e.g., anticancer) agents are contemplated for use in certain embodiments of the present disclosure. Anticancer agents suitable for use with the present disclosure include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present disclosure include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies.

In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, chemotherapy agents, adjuvants, etc.) can be any of the well-known agents in the art, including, but not limited to, those that are currently in clinical use.

In some embodiments, a composition comprising a non-neuroinvasive herpes or alphaherpes virus is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some embodiments, administration via mucosal route is sufficient to induce both mucosal as well as systemic immunity towards the herpes or alphaherpes virus. In other embodiments, administration via multiple routes serves to provide both mucosal and systemic immunity. Thus, although an understanding of the mechanism is not necessary to practice the present disclosure and the present disclosure is not limited to any particular mechanism of action, in some embodiments, it is contemplated that a subject administered a composition of the present disclosure via multiple routes of administration (e.g., immunization (e.g., mucosal as well as airway or parenteral administration of the composition) may have a stronger immune response to a non-neuroinvasive herpes or alphaherpes virus than a subject administered a composition via just one route.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In some embodiments, a vaccine or pharmaceutical composition of the present disclosure is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose). Concentrated compositions are contemplated to be useful in a setting in which large numbers of subjects may be administered a composition of the present disclosure (e.g., an immunization clinic, hospital, school, etc.). In some embodiments, a composition comprising a non-neuroinvasive herpes or alphaherpes virus of the present disclosure (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks. The present disclosure further provides kits comprising the vaccine or pharmaceutical compositions comprised herein. In some embodiments, the kit includes all of the components necessary, sufficient or useful for administering the vaccine. For example, in some embodiments, the kits comprise devices for administering the vaccine (e.g., needles or other injection devices), temperature control components (e.g., refrigeration or other cooling components), sanitation components (e.g., alcohol swabs for sanitizing the site of injection) and instructions for administering the vaccine.

II. Uses

The non-neuroinvasive viruses described herein find use in a variety of research, screening, and therapeutic applications.

Embodiments of the present disclosure provide vaccine compositions for use in the prevention of disease in human and non-human animals (e.g., livestock and companion animals).

In some embodiments, the non-neuroinvasive viruses described herein find use in cancer therapy (e.g., as oncolytic viruses). An oncolytic virus is a virus that preferentially infects and kills cancer cells. As the infected cancer cells are destroyed by lysis, they release new infectious virus particles to help destroy the remaining tumor. Oncolytic viruses are thought not only to cause direct destruction of the tumor cells, but also to stimulate host antitumor immune responses. Oncolytic herpesviruses are described, for example, in Varghese, et al. (Cancer Gene Therapy 9 (12): 967-78). In some embodiments, the modified non-neuroinvasive viruses described herein find use as oncolytic viruses (e.g., as described herein or with further modification).

In some embodiments, the viral compositions described herein find use in vaccination (e.g., against herpesvirus and alphaherpes virus infection).

In some embodiments, following an initial administration of a composition of the present disclosure (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eights, ninth, tenth, and/or more than tenth administration. Although an understanding of the mechanism is not necessary to practice the present disclosure and the present disclosure is not limited to any particular mechanism of action, in some embodiments, reintroduction of a non-neuroinvasive herpes or alphaherpes virus in a boost dose enables vigorous systemic immunity in a subject. The boost can be with the same formulation given for the primary immune response, or can be with a different formulation that contains the virus. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

In some embodiments, the compositions described herein find use in research uses (e.g., to identify neurons in cells and non-human animals). For example, in some embodiments, the modified viruses described herein find use as anterograde-specific trans-synaptic tracers of the mammalian nervous system.

EXPERIMENTAL

The following examples are provided in order to demonstrate and further illustrate certain preferred embodiments and aspects of the present disclosure and are not to be construed as limiting the scope thereof.

Example 1

Crystal Structure of the Herpesvirus Inner Tegument Protein UL37
Materials and Methods
Cloning.

Plasmid pGS3610 encodes the PRV Becker UL37 gene fused to an N-terminal His6-SUMO tandem tag. This was made by cutting the pETDuet-SUMO vector (a derivative of pETDuet-1 and a gift from Thomas Schwartz) and the pGS1740 subclone of UL37 with BamHI and HindIII. The pJP4 plasmid, which contains a His6-SUMO-PreScission tag in frame with the BamHI restriction site of the multiple-cloning site in a pET24b vector, was made through PCR of the His6-SUMO-PreScission tag from pETDuet-SUMO using the primers 5=-GGGAATTC-CATATGGGCAGCAGCCATCACCATCA (SEQ ID NO: 1) and 3=-CTAGGGATCCGGGCCCCTGGAACAGAACTT (SEQ ID NO: 2). The PCR product was subcloned into pET24b using NdeI and BamHI restriction sites. The PRV UL37 gene for *Escherichia coli* expression was synthesized by GeneArt. The N-terminal half (residues 1 to 496) of codon-optimized PRV UL37 (referred to as UL37N) was amplified by PCR from the full-length PRV codon-optimized UL37 gene using the primers 5=-CTAGGGATC-CATGGAAGCACTGGTTCGTGC (SEQ ID NO: 3) and 3=-CTAGAAGCTTCTAGGCTGCGCTGGTCGGTG (SEQ ID NO: 4). The PCR product was subcloned into pJP4 using the BamHI and HindIII restriction sites to yield plasmid pJP23.
Virus Construction.

All recombinant PRV (strain Becker) isolates were derived from a variant of the pBecker3 infectious clone, pGS4284, that encodes the mCherry red fluorescent protein fused in frame to the UL25 capsid protein (Bohannon K P, Sollars P J, Pickard G E, Smith G A. 2012. Fusion of a fluorescent protein to the pUL25 minor capsid protein of pseudorabies virus allows live-cell capsid imaging with negligible impact on infection. J. Gen. Virol. 93:124-129). Viruses were produced by electroporation of infectious clones into the pig kidney epithelial cell line PK15, as previously described (Luxton G W, Haverlock S, Coller K E, Antinone S E, Pincetic A, Smith G A. 2005. Targeting of herpesvirus capsid transport in axons is coupled to association with specific sets of tegument proteins. Proc. Natl. Acad. Sci. U.S.A 102:5832-5837). PK15 cells were maintained in Dulbecco modified Eagle medium (DMEM; Invitrogen) supplemented with 10% bovine growth supplement (BGS; HyClone), which was reduced to 2% during transfection and infection. The harvested virus was passaged once to produce a high-titer stock by infecting a 10-cm dish of PK15 cells with 1 µl virus. Transfection of pGS4284 resulted in PRV-GS4284, which upon passage propagated to titers of >5×10$^8$ PFU/ml. To make PRV encoding the pentuple mutations D79A/D81A/E82A/D382A/D383A in the calcium-binding region (Ca) of UL37, codon changes were introduced through two rounds of en passant mutagenesis of pGS4284. The first set of primers, 5=CTCGCCGAGAACCTGGC CGGCCTGGCGCTGTGGCGCCTGCGC-CACGCCTGGGCCGCGGGCACGGCCCCGCT GAG-GATGACGACGATAAGTAGGG (SEQ ID NO: 5) and 5=GTCGCCGTTGACGACCCCCAG-GAGCTCCAGCAGCGGGGCCGTGCCCGCGGCC CAGGCGTGGCGCAGGCGCCACAACCAATTAAC-CAATTCTGATTAG (SEQ ID NO: 6), was used to generate the D382A/D383A mutations (mutated bases are in bold) and produced pGS5456. The second set of primers, 5=GTCGGCTGCACGGCGGTCGTCGGCGGCGTCGTG CACCGCCTCCTCGCCGCCTA CGGGCCCGGGCT-GAGGATGACGACGATAAGTAGGG (SEQ ID NO: 7) and 5=CGCGACGTCCGTGTAGGCGCGCACGTAGTCCAG CCCGGGCCCGTAGGCGGCG AGGAGGCGGTGCAC-CAACCAATTAACCAATTCTGATTAG (SEQ ID NO: 8), was used to generate the D79A/D81A/E82A mutations, which were introduced into pGS5456 to produce the final mutant, pGS5476. PRV-GS5476 typically propagated to a titer of >5×108 PFU/ml. The region 2 (R2) and region 3 (R3) mutant viruses were produced in the same manner as the Ca mutant. For R2, mutations were introduced into pGS4284 in three sequential rounds using primers 5=-CTCGAC-CACACGCAGGTGGACGCCACGGGCGTGTGG-GAGGCGGTGGCGGCCAG CGCCTCGCCGAG-GATGACGACGATAAGTAGGG (SEQ ID NO: 9) and 5=-CGCGGTCACGAGCGCCTC-CACGACCTGCAGCGGCGAGGCGCTGGCCGC-CACCGC CTCCCACACCAACCAATTAACCAATTCT-GATTAG (SEQ ID NO: 10) (encoding Q324A), 5=-GACCTCCTCGAGCGCGCCGTGCTGGACCGCGCG CCCCGCCTGACGGCCGCGCAG GCTGCCGTCGGCTGCACGAGGATGACGACGA-TAAGTAGGG (SEQ ID NO: 11) and 5=-GAGGCGGTGCACGACGCCGCCGACGACCGCCG TGCAGCCGACGGCAGCCTGCGC GGCCGTCAGGCGGGGCGCCAACCAATTAACCAAT-TCTGATTAG (SEQ ID NO: 12) (encoding D362A/R365A), and 5=-GGGGACGTGACGGCGGCGCTGGGGCTCCCCGA GAAGGGCGTGGAGGCCGTGGT GCGCGCTTG-CATGGCGCCGCGCAGGATGACGACGATAAGTAGGG (SEQ ID NO: 13) and 5=-GCGCGCCGCGCC-CACGTGCTCCGTGGGCGGGCGCGGCGC-CATGCAAGCGCCAC CACGGCCTC-CACGCCCTTCTCCAACCAATTAACCAATTCTGATTAG (SEQ ID NO: 14) (encoding H421A/H425A). The first PCR product was recombined into pGS4284, resulting in pGS5483. The second PCR product was then recombined into pGS5483, resulting in pGS5558. The final recombination was made into pGS5558, resulting in pGS5604. PRV-GS5604 typically propagated to a titer of >5×10⁸ PFU/ml. The R3 mutations were introduced in two rounds using primers 5=-CTGCCGCTGGCGTTGGCGGTGCGCCA-GATGCAGAACGAGGGCCTGGCGCAGCTG ACGCGCGCGCTCAGGATGACGACGATAAGTAGGG (SEQ ID NO: 15) and 5=-GAAGAACTCGTCGGC-GATCGT-GAGGGCAAAGAGCGCGCGCGTCAGCTGCGCCA GGCCCTCGTTCTGCAACCAATTAACCAATTCT-GATTAG (SEQ ID NO: 16) (encoding D239A/E240A) and primers 5=AACCCGACGCTGCGCGAGCAGTTCGCCGAGGC GGCGCGGGCCGTGGCCGCGG CGGCGCTGGTGCCCAGGATGACGACGA-TAAGTAGGG (SEQ ID NO: 17) and 5=-CGTGCGCGGCGTGGCGTTGACCTCGCC-CACGGGCACCAGCGCCGCCGCGGCCAC GGCCCGCGCCGCCAACCAATTAACCAATTCT-GATTAG (SEQ ID NO: 18) (encoding K203A/P204Q). The first PCR product was recombined into pGS4284, resulting in pGS5242. The second PCR product was then recombined into pGS5242, resulting in pGS5350. PRV-GS5350 typically propagated to a titer of >5×10⁸ PFU/ml. The region 1 (R1) mutant virus (V249R/R254A/R285A/D287A/H311A) was generated using a modified two-step recombination. The region of the UL37 gene encoding amino acids 249 to 311 was first replaced with the kanamycin resistance cassette of pEPkan-S using primers 5=-CCGAGGCGGCGCGGGCCGTGGACGAGGCGGCG CTGGTGCCCGTGGGCGAGACG CAGGTGGACGC-CACGGGAGGATGACGACGATAAGTAGGG (SEQ ID NO: 19) and 5=-GAGGCGCTGGCCTGCACCGCCTCC-CACACGCCCGTGGCGTCCACCTGCGTCTCGC CCACGGGCACCAGCGCAACCAATTAACCAATTCT-GATTAG (SEQ ID NO: 20). The PCR product was recombined into pGS4284, resulting in the intermediate construct pGS5313. The deletion in pGS5313 was then repaired using a 489-bp synthetic DNA encoding the missing UL37 sequence with the five codon changes and 150 bp of flanking homologous sequence to each side (pGS5267; Integrated DNA Technologies). The synthetic DNA was released from a pIDTSmart vector using flanking HindIII sites and recombined into pGS5313. Recombination was carried out by growing E. coli strain GS1783 harboring pGS5313 in 30 ml of Luria Broth (LB) supplemented with 20 µg/ml chloramphenicol to an optical density at 600 nm (OD600) of 0.6 at 32° C. in a baffled flask.

At this point, 20 ml of LB supplemented with 20 µg/ml chloramphenicol and 2% L-arabinose was added, and the culture was incubated with shaking at 32° C. for 70 min. The culture was then transferred to a 42° C. shaking water bath for 15 min, and the contents were then transferred to a 50-ml conical tube and chilled on ice. The chilled bacteria were washed three times, and the final pellet was suspended in 300 ml double-distilled H2O, of which 48 µl was used in an electroporation with 2 µl of the pGS5267 synthetic fragment. After recovery, the reaction mixture was plated on LB agar plates supplemented with 20 µg/ml chloramphenicol and 2% L-arabinose. The resulting isolate was saved as pGS5321. PRV-GS5321 typically propagated to a titer of >5×10⁸ PFU/ml. The sequences of all genetic modifications in the infectious clones were confirmed.

Viral Propagation Kinetics, Viral Titers, and Plaque Size Analysis.

Quantitation of viral propagation kinetics was assessed by single-step growth in PK15 cells infected at a multiplicity of infection (MOI) of 10 for each viral stain. Viral titers from cells or medium supernatants harvested at 2, 5, 8, 12, or 24 h postinfection (hpi) were determined in duplicate by plaque assay, as previously described (Smith G A, Enquist L W. 1999. Construction and transposon mutagenesis in *Escherichia coli* of a full-length infectious clone of pseudorabies virus, an alphaherpesvirus. J. Virol. 73:6405-6414). Measurements of plaque diameters were obtained by infection of PK15 cells in 6-well trays with serial 10-fold dilutions for each virus. At 4 days postinfection, images were captured with a λ4 objective on a Nikon TE2000 inverted fluorescence microscopy (Nikon Instruments) fitted with a Cool-Snap HQ2 camera (Photometrics). Two orthogonal diameter measurements of each fluorescent plaque were obtained using the Metamorph software package (Molecular Devices) and averaged. The reported plaque diameters represented an average of more than 50 plaques per virus. Measurements of the plaque diameters of mutant viruses were always conducted side by side with measurement of the plaque diameter of PRV-GS4284 (the virus encoding wild-type [WT] UL37), and the diameters of the mutant viruses were normalized to that diameter. Single-step growth and plaque diameters were plotted using the Prism software package (GraphPad Software).

Virion Protein Incorporation.

PK15 cells were infected with either PRV-GS4284 (WT) or PRV-GS604 (R2) at an MOI of 3. Infections were carried out in 15-cm dishes of confluent cells. Infected cells and extracellular media were harvested once all cells displayed a cytopathic effect, which was typically at 18 hpi. Cellular debris was removed by centrifugation at 5,000×g, and virions were concentrated from the supernatant by pelleting through a 10% Nycodenz cushion at 13,000 rpm in an SW28 rotor (Beckman). The resulting pellet was resuspended in 100 µl of THE buffer (150 mM NaCl, 50 mM Tris [pH 7.4], 10 mM EDTA). Viral particles were dispersed by 10 1-s pulses of sonication in a cup horn ultrasonic processor (VCX-500; Sonics and Materials, Newtown, Conn.). The sample was loaded onto a 12 to 32% dextran gradient and centrifuged at 20,000 rpm for 1 h at 4° C. The heavy viral band was collected and spun at 25,000 rpm in a Beckman SW50.1 rotor at 4° C. for 30 min. The final pellet was resuspended in final sample buffer (10 mM Tris [pH 7.4], 150 mM NaCl, 1% Triton X-100) containing 10% β-mercaptoethanol, and the samples were boiled for 5 min prior to electrophoresis of 5 µl of each sample through an 8% sodium dodecyl sulfate (SDS)-polyacrylamide gel. Proteins were subsequently transferred onto an Immobilon polyvinylidene difluoride membrane (Millipore), and VP5 was detected using the 3C10 mouse monoclonal antibody (a gift of Lynn Enquist) at a 1:1,000 dilution. UL37 was detected using D1789, a rabbit antiserum raised against a peptide derived from the PRV UL37 sequence (REAADRVLGDYHE), at a 1:2,500 dilution. The secondary goat antimouse and anti-rabbit dye-labeled antibodies (LiCor) were used at 1:5,000 dilutions. Proteins were visualized and quantitated using an Odyssey Fc imager and ImageStudio software (LiCor). The ratio of UL37 to VP5 was quantified for four independent experiments and normalized to the average value obtained for the UL37-to-VP5 ratio for WT virus. Data were plotted using the Prism software package (GraphPad Software), and significance was determined using an unpaired Student's t test.

Protein Expression and Purification.

Both UL37 and UL37N constructs were expressed as N-terminal His6-SUMO fusions in T7 Express *E. coli* (New England BioLabs). Freshly transformed cells were incubated at 37° C. overnight in 5 ml LB starter culture supplemented with 50 µg/ml kanamycin. The starter culture was diluted into 1 liter LB supplemented with 50 µg/ml kanamycin and grown at 37° C. until the OD600 reached 0.8 to 1.0. At this point, the temperature was shifted to 16° C. and the cells were induced with 0.5 mM isopropyl-β-D-thiogalactopyranoside (IPTG). For production of UL37N, expression was induced for 16 to 20 h. Cells were harvested by centrifugation at 12,000×g for 40 min, resuspended in 25 ml 20 mM piperazine-N,N'-bis(2-ethanesulfonic acid) (PIPES), pH 7.0, 50 mM NaCl, 0.1% Igepal CA-630 (Sigma), 5% glycerol, 10 mM imidazole, 0.1 mM tris(2-carboxyethyl)phosphine (TCEP), and 1 EDTA free complete protease inhibitor cocktail tablet (Roche), and lysed by use of a French press. The insoluble fraction was removed by centrifugation of the whole-cell lysate at 14,000×g for 30 min at 4° C. Soluble lysate was loaded onto a 5-ml Ni-Sepharose 6B FF column (GE Healthcare). The column was subsequently washed with 10 column volumes (CVs) of 20 mM PIPES, pH 7.0, 50 mM NaCl, 0.1 mM TCEP (buffer A) containing increasing amounts of imidazole at 10 mM or 25 mM. Protein was eluted in buffer A containing 100 mM imidazole. The eluate was immediately concentrated, and the imidazole was removed by buffer exchange into buffer A using an Ultra-15 50-kDa-cutoff concentrator (Millipore). The protein concentration was determined from the absorbance at 280 nm using a calculated extinction coefficient. Glutathione S-transferase (GST)-tagged PreScission protease was added to the protein solution at a 1:50 protease-to-protein ratio, and the protein was cleaved overnight at 4° C. to remove the His6-SUMO tag. The protease-protein solution was sequentially applied to glutathione-Sepharose 4B (GE Healthcare) and Ni-Sepharose 6B to remove the GST-tagged PreScission protease and the His6-SUMO tag, respectively. Cleaved protein was present in the unbound and wash fractions. UL37N was further purified by size exclusion chromatography using a Superdex 200 column (GE Healthcare) and concentrated to 3.5 to 4.0 mg/ml using an Ultra-15 30-kDa-cutoff concentrator (Millipore). Protein purity was assessed by SDS-polyacrylamide gel electrophoresis (PAGE) and Coomassie G-250 staining. The final yield was 18 mg of pure protein per 1 liter of *E. coli* culture. All UL37N protein samples used for crystallization and biochemical studies were stored in 20 mM PIPES, pH 7.0, 50 mM NaCl, and 0.5 mM TCEP.

A BL21 *E. coli* strain expressing GST-tagged PreScission protease was a gift from Peter Cherepanov (London Research Institute, London, United Kingdom). Protein expression was induced with 0.5 mM IPTG at 30° C. for 4 h before the cells were harvested and lysed. The PreScission protease was purified over glutathione-Sepharose in a buffer containing 20 mM Tris, pH 8.0, 200 mM NaCl, and 1 mM TCEP. The column was washed 3 times with 10 CVs of the binding buffer, and protein was eluted from the column in binding buffer containing 5 mM reduced glutathione. The eluted protein was concentrated in a 30-kDa-cutoff concentrator (Millipore) and further purified over a Superdex 200 size exclusion column equilibrated with the binding buffer. The protein was concentrated to 1 mg/ml, flash frozen, and stored at −80° C.

Thermofluor Assay.

The optimal buffer composition and the optimal NaCl concentration for the stability of the UL37N protein (PIPES, pH 7.0, and 50 mM NaCl) were determined using the Thermofluor method (34). Protein was diluted to 0.15 mg/ml in the storage buffer, and a fluorescent dye, SYPRO orange (Invitrogen), was added at a 1:1,000 dilution. Ten microliters of the protein-dye solution was pipetted into each well of a 96-well PCR microplate. Next, 10 µl of buffer (from a custom-made screen containing buffers at pH 4.5 to 10.5 and NaCl concentrations ranging from 0 to 500 mM) was added to wells containing the protein dye solution. The plate was sealed and centrifuged for 1 min at 500×g and 25° C. Samples were analyzed on a Roche LightCycler 480 quantitative PCR machine using an excitation wavelength of 465 nm and detection of emission at 610 nm. The emission signal was analyzed from 25° C. to 95° C. at a continuous acquisition rate of 3 measurements per ° C. Data were analyzed using the ThermoQ software program. Conditions that stabilized UL37N further increased its solubility.

Mass Spectrometry.

For mass spectrometry analysis, the UL37 protein was analyzed using sinapinic acid (Agilent Technologies) as the matrix. Mass spectrometry measurements were performed on a Voyager DE-Pro matrix-assisted laser desorption ionization-time of flight mass spectrometer (Applied Biosystems).

Crystallization and structure determination. Crystals of UL37N were grown by vapor diffusion at room temperature in hanging drops using 1 µl protein and 1 µl well solution containing 24 to 26% polyethylene glycol 1000, 0.3M $Ca(CH_3COO)_2$, and 0.1M imidazole, pH8.0. Large plates formed in 3 to 8 days and were harvested 2 to 4 weeks later. For data collection, crystals were incubated in a solution identical to the well solution plus 10% glycerol for 30 s to 2 min prior to flash freezing in liquid N2. Heavy atom derivative crystals were obtained by soaking native crystals in well solution containing 5 mM thimerosal (Na salt of ethylmercurithiosalicylic acid or $C_9H_9HgNaO_2S$) for 12 to 16 h. Derivative crystals were harvested and frozen using the protocol developed for the native crystals. X-ray diffraction data were collected at 100 K at the X25 beam line at the National Synchrotron Light Source. The data were processed using HKL2000 (Otwinowski Z, Minor W. 1997. Processing of X-ray diffraction data collected in oscillation mode. Methods Enzymol. 276:307-326) and indexed in space group P21 (Table 1). The native data set was processed up to a 2.0-Å resolution, and the single-wavelength anomalous dispersion (SAD) Hg data set was processed to a 2.3-Å resolution (Table 1). All 12 heavy atom sites were found using the phenix.autosol program, and the experimental density allowed the tracing of the residues in the phenix.autobuild program. Additional residues were manually built using the Coot program (Emsley P, Cowtan K. 2004. Coot: model-building tools for molecular graphics. Acta Crystallogr. D Biol. Crystallogr. 60:2126-2132). There are two UL37N molecules in the asymmetric unit.

Before refinement of the heavy atom model, 10% of the data was set aside for cross-validation. The model was refined against the SAD Hg data set to 2.3-Å resolution using the phenix.refine program. Next, test set flags were transferred to the native data set; additionally, 10% of the native data between 2.3 and 2.0 Å was set aside for cross-validation. After several cycles of refinement in the phenix.refine program (Adams P D, Grosse-Kunstleve R W, Hung L W, Ioerger T R, McCoy A J, Moriarty N W, Read R J, Sacchettini J C, Sauter N K, Terwilliger T C. 2002. PHENIX: building new software for automated crystallographic structure determination. Acta Crystallogr. D Biol. Crystallogr. 58:1948-1954) and rebuilding in Coot (Emsley et al, supra), Rwork was 17.3% and Rfree was 22.0%. The final model contained all amino acids from residues 1 to 479, including 3 of the 4 linker residues left after protease cleavage of the N-terminal tag. The final model is missing residues 480 to 496 in both chains. The MolProbity server (Davis I W, Leaver-Fay A, Chen V B, Block J N, Kapral G J, Wang X, Murray L W, Arendall W B, III, Snoeyink J, Richardson J S, Richardson D C. 2007. MolProbity: all-atom contacts and structure validation for proteins and nucleic acids. Nucleic Acids Res. 35:W375-W383) was used to assess the stereochemical quality of all models. According to MolProbity, 99.0% of the residues lie in the most favored regions of the Ramachandran plot and 1% lie in the additionally allowed regions of the Ramachandran plot. Final statistics are listed in Table 1.

Structure Analysis.

The sequence alignment was generated and analyzed using the ClustalW (Larkin M A, Blackshields G, Brown N P, Chenna R, McGettigan P A, McWilliam H, Valentin F, Wallace I M, Wilm A, Lopez R, Thompson J D, Gibson T J, Higgins D G. 2007. Clustal W and Clustal X version 2.0. Bioinformatics 23:2947-2948) and ESPRIPT (Gouet P, Courcelle E, Stuart D I, Metoz F. 1999. ESPript: analysis of multiple sequence alignments in PostScript. Bioinformatics 15:305-308) programs. Interfaces were analyzed using the PISA program (Krissinel E, Henrick K. 2007. Inference of macromolecular assemblies from crystalline state. J. Mol. Biol. 372:774-797). Structural homology searches were performed using the Dali server (Holm L, Rosenstrom P. 2010. Dali server: conservation mapping in 3D. Nucleic Acids Res. 38:W545-W549), and the top hits were superposed onto the UL37N protein using the Dalilite pairwise comparison tool. The Evolutionary Trace server was used for evolutionary trace analysis. All structure figures were made in the PyMOL program.

Protein Structure Accession Number.

Atomic coordinates and structure factors for the UL37N structure have been deposited in the RCSB Protein Data Bank under accession number 4K70.

Results

Characterization of UL37N.

Figure 1:
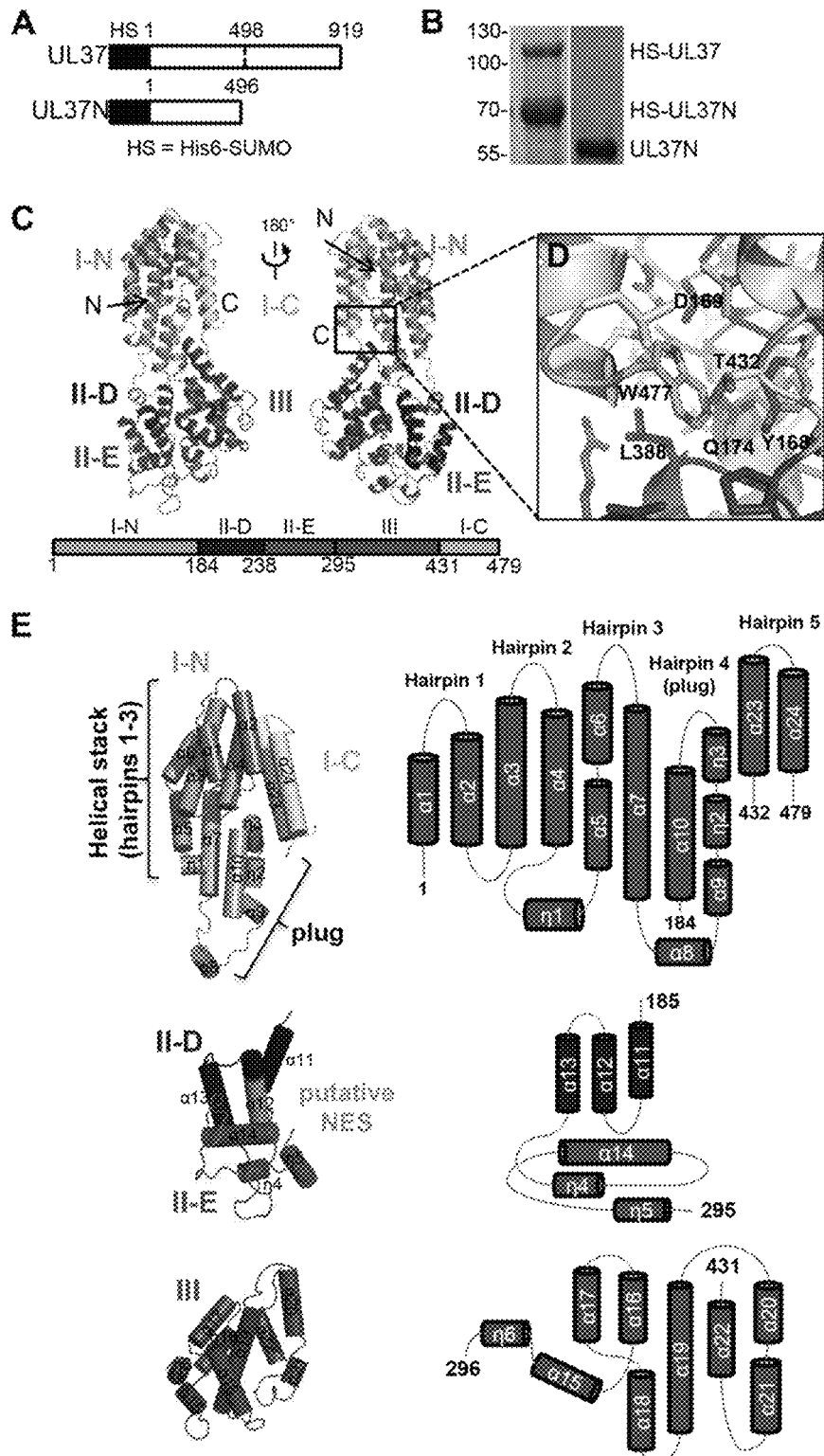

Initially, full-length PRV UL37 was expressed with an N-terminal His6-SUMO tag in *E. coli* (FIG. 1A). During expression, this protein underwent spontaneous proteolysis, which generated a fragment containing the His6-SUMO tag and the N terminus of UL37 (FIG. 1B). Using mass spectrometry, the proteolytic site was localized around residue 498, which is approximately in the middle of the UL37 sequence. The difficulty in separating full-length UL37 from the truncated UL37 resulted in a very low yield of the purified full-length UL37, ~200 µg/liter cell culture. Unlike full-length UL37, which was prone to aggregation, the N-terminal product of proteolytic cleavage was readily soluble and was pursued further. A fragment containing residues 1 to 496 of UL37 (UL37N) plus an N-terminal His6-SUMO tag was expressed in *E. coli* (FIG. 1A), purified to homogeneity, and the His6-SUMO tag was cleaved (FIG. 1B), obtaining a yield of ~18 to 20 mg per liter of cell culture. The optimal buffer composition and NaCl concentration for protein stability, PIPES, pH7.0, and 50 mM NaCl, were determined using the Thermofluor method. These conditions further increased the solubility of UL37N. All UL37N protein samples used for crystallization and biochemical studies were stored in 20 mM PIPES, pH 7.0, 50 mM NaCl, and 0.5 mM TCEP.

Architecture of UL37N.

The crystal structure of UL37N was determined using single anomalous dispersion and refined against a 2.0-Å native data set (Table 1). There are two monomers in the asymmetric unit, and the final model included residues 1 to 479 plus N-terminal linker residues PGS in both monomers (Table 1). The two monomers adopted very similar conformations, with the root mean square deviation (RMSD) being 0.4 for 482 common C-α residues (Holm et al., supra). UL37N is an elongated molecule with dimensions of 99 by 42 by λ6 Å composed of 24 α helices and 6 310 helices arranged into a series of helical bundles (FIG. 1C). The structure can be divided into three domains: domain I, residues 1 to 184 and 432 to 479; domain II, residues 185 to 295; and domain III, residues 296 to 431 (FIGS. 1C and E).

Domain I is formed by two noncontiguous segments of the polypeptide chain, residues 1 to 184 and residues 432 to 479 (FIG. 1E). Residue 479 is the last resolved residue; no electron density was observed for residues 480 to 496, and they are likely disordered. Domain I consists of five helical hairpins with the up-down topology which are formed by 12 α helices (α 1 to α 10, α 23, and α 24) and 3 310 helices (η1 to η3). Linker residues GS, which precede the start methionine, form the N terminus of helix α 1. Hairpins 1 through 3 form a helical stack (FIG. 1E). Hairpin 1 consists of two short antiparallel helices, while hairpin 2 consists of two longer kinked helices, and hairpin 3 has two up helices followed by a loop and a single down helix. Helix η1 connects hairpins 2 and 3. The last two helices, α 23 and α 24, form hairpin 5 (FIG. 1E). Only the top part of hairpin 5 interacts with hairpins 1 to 3, an arrangement that results in a large U-shaped groove within domain I. Hairpin 4, formed by helix α 10 running antiparallel to helices α 9 and η2, forms a plug in the U-shaped groove in domain I. Helix η3 forms the tip of the plug. At the opposite end of the plug, a solitary helix, α 8, at the tip of a long extension interacts with domain II.

Figure 2:
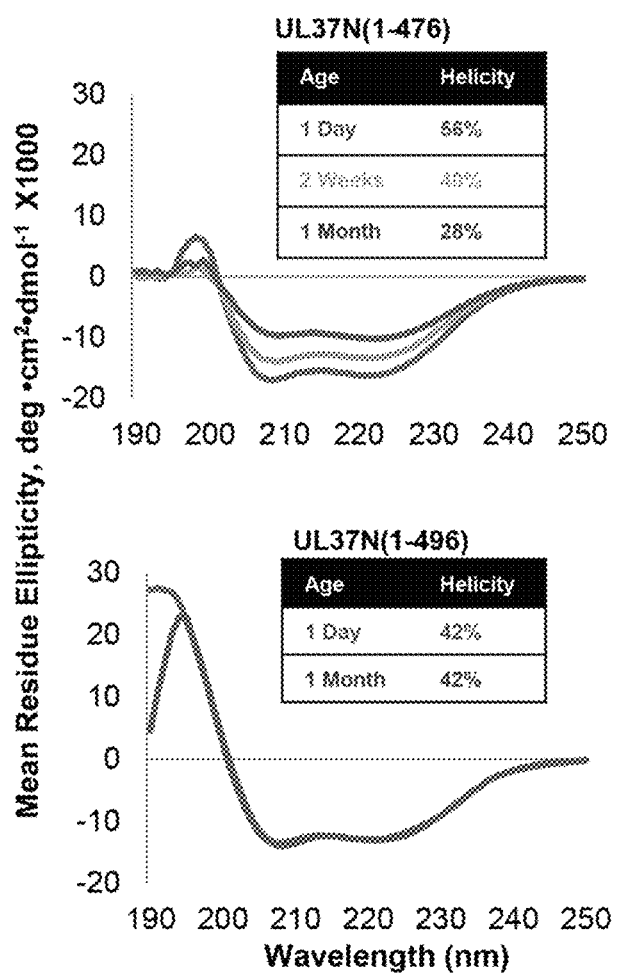
FIG. 2 shows that UL37N (1 to 496) is more stable over time than UL37N (1 to 476), as measured using circular dichroism on protein aged 1 day, 2 weeks, or 1 month.

The Dali structural homology search (Holm et al., supra) revealed that domain I bears a structural resemblance to the helical bundle domains of several subunits of multisubunit tethering complexes. Conserved residue W477 plays a key role in the stability of not only domain I but also the entire UL37N because a shorter construct, UL37N from residues 1 to 476 [UL37N(1 to 476)], which lacks residue W477, has a lower thermal stability and progressively loses secondary structure during storage (FIG. 2). W477 helps anchor the hairpin 4 plug in domain I through van der Waals interactions with several hydrophobic residues and a hydrogen bond with the carboxyl of D169 (FIG. 1D), as well as van der Waals interactions with several hydrophobic residues in domain III. Domain II, residues 185 to 295, consists of helices α 11 to α 14 and two 310 helices (η4 and η5) (FIG. 1E). Helices α 11 to α 13 form a helical bundle, in which the last turn of helix α 12 adopts a π-helix conformation. The putative nuclear export signal (NES), residues 263 to 273 in HSV-2 (Watanabe D, Ushijima Y, Goshima F, Takakuwa H, Tomita Y, Nishiyama Y. 2000. Identification of nuclear export signal in UL37 protein of herpes simplex virus type 2. Biochem. Biophys. Res. Commun. 276:1248-1254), maps to buried helix α 12 (FIG. 1E) and is unlikely to be functional. Two long loops at the bottom of domain II are well structured (FIG. 1E) and adopt similar conformations in the two UL37N molecules present within the crystal asymmetric unit. Helix α 14 appears to buttress both loops. Domain II does not have any structural homologs according to the Dali server (Holm et al., supra). Domain III, residues 296 to 431, is composed of helices α 15 to α 22 and one 310 helix (η6) (FIG. 1E). This domain is also a helical bundle, with the α 19 central helix surrounded by the other six helices. This central helix maintains the structural integrity of domain III and is highly conserved.

UL37N is a Dimer in Crystals but a Monomer in Solution.

Figure 3:
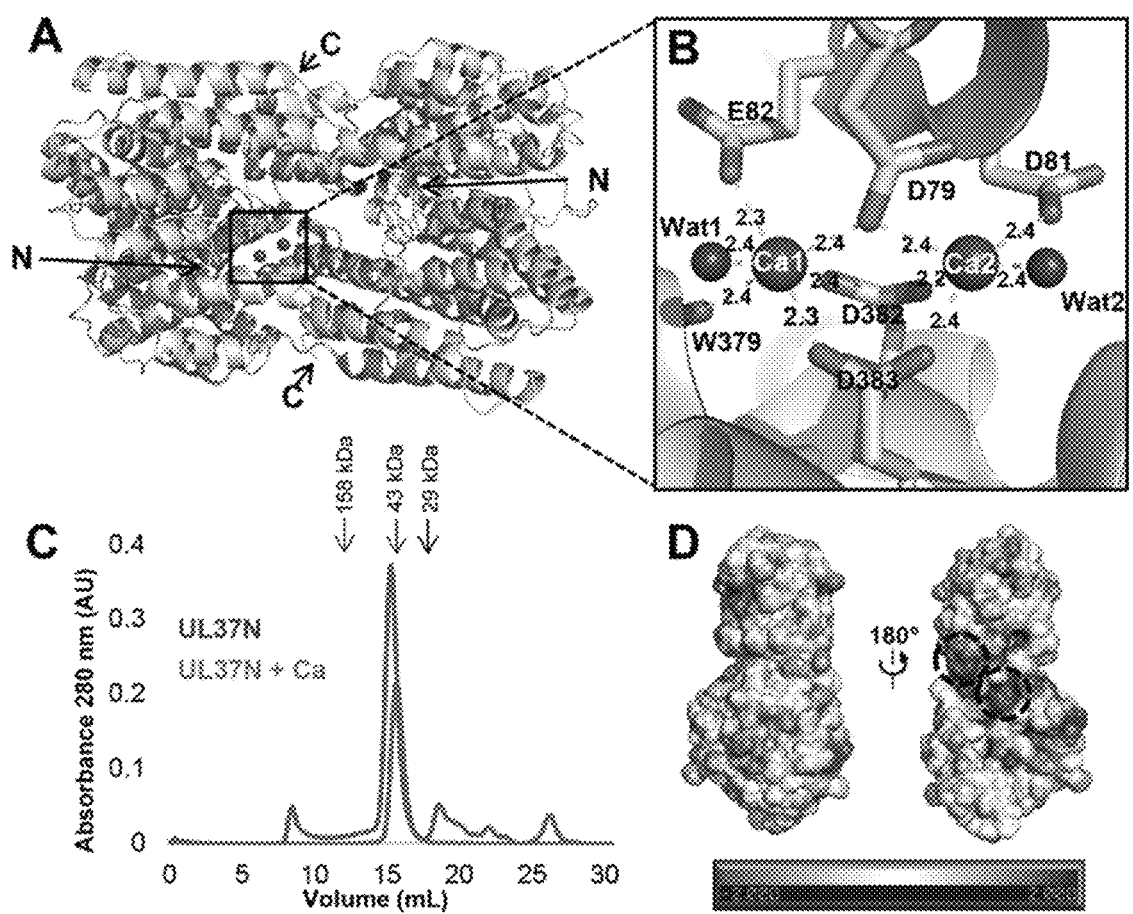
FIG. 3 shows that UL37N is a calcium-dependent dimer in crystals but not in solution.
(A) Two UL37N monomers in the asymmetric unit. (B) A close-up view of the calcium-binding site at the dimer interface. (C) Overlay of size exclusion chromatograms of UL37N with or without 0.2 M CaCl2. (D) Electrostatic surface potential map of UL37N generated using the Charmm program.

Two UL37N monomers in the asymmetric unit form an X-shaped dimer (FIG. 3A) that buries 1,734.8 Å2 of surface area. Four calcium ions are coordinated at the dimer interface as two symmetry related sets of two calcium ions. Each set is coordinated by carboxyl oxygens from the side chains of Asp79, Asp81, and Glu82 of one monomer, carboxyl oxygens from the side chains of Asp382 and Asp383 plus the carbonyl oxygen of Trp379 of the other monomer, and two water molecules (FIG. 3B). As a result, one calcium ion is hexahedrally coordinated, while the second is pentahedrally coordinated.

Despite forming a dimer in crystals, UL37N is a monomer in solution. Crystal formation required the presence of at least 0.1M $Ca(CH_3COO)_2$, and the best crystals were obtained in the presence of 0.3M $Ca(CH_3COO)_2$. In solution, UL37N remained monomeric even in the presence of 0.2M $CaCl_2$, judging by its elution volume on size exclusion chromatography (FIG. 3C). It was concluded that the dimerization of UL37N observed in crystals is likely induced by crystallization conditions (a high protein concentration and the presence of calcium). The coordination of four calcium ions at the dimer interface helps explain the importance of calcium ions in mediating crystal contacts. In the absence of calcium, the buried interface would have been smaller, 1,504.0 Å2 instead of 1,734.8 Å2. Although UL37N does not dimerize in solution, the dimerization interface features multiple grooves and several negatively charged patches (FIG. 3D). In full-length UL37, this area may participate in intramolecular contacts with the C-terminal half of UL37, which is also conserved among alphaherpesviruses and is predicted to be largely α helical.

ETA reveals several conserved surface clusters within UL37N. To analyze sequence conservation within UL37N, a sequence alignment of 15 UL37 homologs from alphaherpesviruses, a subfamily of herpesviruses that includes HSV and PRV, was generated. Thirty five strictly conserved residues (FIG. 4) were identified. Most are located within the hydrophobic core and are used for maintaining the structural integrity of the protein, but 11 of these conserved residues are surface exposed (FIGS. 3 and 5A) and are a logical choice for mutational analysis because surface-exposed conserved residues often participate in protein-protein interactions. None of these, however, clustered in a way that would help pinpoint regions of potential functional importance (FIG. 5A).

To locate potentially important functional sites on the surface of UL37N, ETA (43) was performed on the same sequence alignment (FIG. 6). ETA uses a sequence alignment of homologous proteins to generate a phylogenetic tree, which is then broken up into partitions, with more closely related sequences being grouped into classes. Within each partition, consensus sequences are generated for each set of sequences within a class. Each position within the sequence alignment is designated conserved, class specific, or neutral. Conserved residues have the same residue in all consensus sequences, whereas class-specific residues have a common residue for each closely related subgroup, but that residue is different among more divergent subgroups. Positions lacking consensus among the members of at least one subgroup are considered neutral. Clustering of conserved and class-specific residues on the protein surface may indicate regions of potential functional importance (Lichtarge O, Bourne H R, Cohen F E. 1996. An evolutionary trace method defines binding surfaces common to protein families. J. Mol. Biol. 257: 342-358). This method has been used to detect functional sites in a number of proteins (Sowa M E, He W, Slep K C, Kercher M A, Lichtarge O, Wensel T G. 2001. Prediction and confirmation of a site critical for effector regulation of RGS domain activity. Nat. Struct. Biol. 8:234-237; Chakravarty S, Hutson A M, Estes M K, Prasad B V. 2005. Evolutionary trace residues in noroviruses: importance in receptor binding, antigenicity, virion assembly, and strain diversity. J. Virol. 79:554-568).

ETA on UL37N revealed several surface clusters which contained both conserved and class-specific residues (FIGS. 5A and B). Several of these were not considered further because they either contained salt bridges, which are likely essential for protein stability alone, or contained several residues with only partially exposed side chains. Three clusters were chosen for further analysis. To probe their functional roles, 4 to 5 residues within each cluster were mutated to either eliminate a bulky side chain or, in two cases, to replace a small side chain with a bulky one. Three mutants with the following mutations were generated: V249R/R254A/R285A/D287A/H311A (R1 mutant), Q324A/D362A/R365A/H421A/H425A (R2 mutant), and K203A/P204Q/D239A/E240A/D295A (R3 mutant) (FIG. 5C). Mutated residues define three regions of potential functional importance, referred to as regions 1 through 3 (R1 to R3, respectively). R1 and R3 are located in domain II of UL37N, and R2 is located in domain III of UL37N. Additionally, residues involved in calcium binding were mutated to confirm that potential calcium-induced dimerization of UL37 is not essential for function, generating the mutant D79A/D81A/E82A/D382A/D383A (Ca).

UL37 Region 2 is Required for Efficient Viral Spread.

All mutations were introduced into the PRV strain Becker background, and each virus was propagated to wild-type titers. To further investigate these mutants, viral replication and spread were measured in single-step growth and plaque formation assays, respectively. The Ca, R1, and R3 mutants did not display any reduction in plaque size or viral replication. In contrast, the R2 mutant plaques were restricted to about half the diameter of virus encoding wild-type UL37 (FIG. 7A). A defect in plaque formation can be the result of a defect in cell-cell spread or propagation kinetics. To address this question, the rates of cell-associated virus production and virus release into the supernatant were measured. The amount of virus released into the supernatant by the UL37 R2 mutant virus was similar to the amount released by the WT virus, indicating that the R2 mutations cause a defect in cell-cell spread (FIG. 7B). There was no reduction in the structural incorporation of the UL37 R2 mutant protein relative to that of wild-type UL37 on the basis of immune detection in purified extracellular virions (FIG. 7C). In fact, the R2 mutant protein was slightly increased in virions relative to the amount of wild-type UL37 (161%; n 4), but this was not statistically significant. It is contemplated that the R2 cluster serves as a binding site for as of yet unidentified cellular or viral proteins important for UL37 function in virus trafficking, which is essential in cell-cell spread.

UL37 Shares Structural Similarity with Subunits of the CATCHR Family of Tethering Complexes.

The UL37 proteins have no notable sequence homology to any viral or host proteins.

A Dali search (Holm et al., supra) revealed that domain I resembles several subunits of eukaryotic multisubunit tethering complexes (MTCs) (Jackson L P, Kummel D, Reinisch K M, Owen D J. 2012. Structures and mechanisms of vesicle coat components and multisubunit tethering complexes. Curr. Opin. Cell Biol. 24:475-483; Brocker C, Engelbrecht-Vandre S, Ungermann C. 2010. Multisubunit tethering complexes and their role in membrane fusion. Curr. Biol. 20: R943-R952). In intracellular trafficking pathways, MTCs tether vesicles to the target organelles to which they localize both to bring the vesicles closer to their target membranes and to help ensure the delivery of the vesicle to the correct target organelle (Brocker et al., supra). Several subunits of four MTCs, the Dsl1 complex, the exocyst complex, the Golgi-associated retrograde protein (GARP) complex, and the conserved oligomeric Golgi protein (COG) complex, share strong structural similarities, despite low sequence identity (Jackson et al., supra; Richardson B C, Smith R D, Ungar D, Nakamura A, Jeffrey P D, Lupashin V V, Hughson F M. 2009. Structural basis for a human glycosylation disorder caused by mutation of the COG4 gene. Proc. Natl. Acad. Sci. U.S.A 106:13329-13334; Tripathi A, Ren Y, Jeffrey P D, Hughson F M. 2009. Structural characterization of Tip20p and Dsl1p, subunits of the Dsl1p vesicle tethering complex. Nat. Struct. Mol. Biol. 16:114-123 Dong G, Hutagalung A H, Fu C, Novick P, Reinisch K M. 2005. The structures of exocyst subunit Exo70p and the Exo84p C-terminal domains reveal a common motif. Nat. Struct. Mol. Biol. 12:1094-1100), a finding which points to their common evolutionary origin and mechanistic similarities. Their structures consist of one to five helical bundle domains of similar folds. UL37N shares the highest structural similarity with several subunits of the Dsl1 complex and the exocyst, with Dali Z-scores of 4.2 to 5.4 (FIG. 8 and Table 2), while similarity to other MTC subunits is less pronounced. Although these similarity scores for the top hits are modest, they are comparable to the scores for some of the more distantly related MTC subunits. The structural similarity to MTC subunits is particularly remarkable because the sequence identity is under 10% (Holm et al., supra).

Residues 1 to 136 of domain I resemble the helical bundles of MTCs the most and typically align with domain C of MTCs (Jackson et al., supra), but the structural similarity between UL37N and MTCs extends beyond domain I and includes domain II (FIG. 8A). The domain I and domain II module resembles domains C, D, and E of MTC subunits and has an overall J shape (FIG. 8A), which is found in some tethering subunits as the result of an additional domain E that follows domains C and D. Although the tip of domain II of UL37N only remotely resembles domain E of MTC subunits, the folds of domain E diverge even among MTC subunits themselves (FIG. 8A). The Cog4 subunit of the COG tethering complex has a salt bridge between domains D and E that involves a conserved arginine (48). UL37N also has a salt bridge between D216 and R260 in subdomains II-D and II-E, respectively (FIG. 8C), that is strictly conserved among alphaherpesviruses (FIG. 4). Despite noticeable similarity, the structure of UL37N differs from the structures of MTC subunits in several aspects. First, instead of multiple helical bundles of similar topology (51), it has only one helical bundle with a topology similar to the topologies found in MTC subunits. Second, unlike in MTC subunits, where domain D or E is C terminal, the polypeptide chain in UL37N continues into domain III and a hairpin in domain I. Thus, the structural resemblance of domains I and II of UL37N to the MTCs may be the result of convergent evolution.

TABLE 1

Data collection and refinement statistics

| Parameter | Value for[a]: | |
|---|---|---|
| | Native Crystal | Native crystal soaked in thimerosal |
| Data collection | | |
| Space group | $P2_1$ | $P2_1$ |
| Unit cell dimensions | | |
| a, b, c, (Å) | 51.67, 156.59, 67.38 | 51.53, 156.30, 66.34 |
| α, β, γ (°) | 90, 91.33, 90 | 90, 91.78, 90 |
| Resolution (Å) | 43.12-2.00 (2.07-2.00) | 48.91-2.05 (2.12-2.05) |
| $R_{sym}$ or $R_{merge}$ | 0.086 (0.516) | 0.097 (0.280) |
| I/σI | 20.32 (2.74) | 13.87 (2.18) |
| Completeness (%) | 89.4 (49.5) | 85.1 (35.31) |
| Redunancy | 6.3 (4.4) | 3.9 (2.1) |
| Refinement statistics | | |
| Resolution Range (Å) | 43.12-2.00 | |
| No. of reflections (free) | 64,342 (2,347) | |
| $R_{work}/R_{free}$ | 17.30/22.01 | |
| No. of atoms | 7,983 | |
| Protein | 7,342 | |
| Ligand/ion | 45 | |
| Water | 596 | |
| B-factors[b] | 35.05 | |
| Protein | 35.03 | |
| Ligand/ion | 42.8 | |
| Water | 37.5 | |
| RMSD | | |
| Bond length (Å) | 0.007 | |
| Bond angle (°) | 0.96 | |

[a]Values in parentheses are for the highest-resolution shell.
[b]B-factor, isotropic displacement parameter.

TABLE 2

Alignments of UL37N with components of MTCs[a]

| Protein | Z-score | RMSD | No. of aligned residues | % identity |
|---|---|---|---|---|
| Tip20 | 5.4 (3.8) | 10.1 (3.8) | 186 (92) | 4 (14) |
| Sec6 | 5.0 (5.1) | 3.9 (3.7) | 145 (111) | 7 (8) |
| Exo70 | 4.4 (5.8) | 15.7 (3.3) | 182 (123) | 6 (9) |
| Dsl1 | 4.2 (5.7) | 11.1 (3.8) | 159 (98) | 6 (7) |
| Cog4 | 3.6 (3.8) | 4.7 (4.6) | 135 (107) | 10 (10) |
| Sec15 | 3.2 (4.4) | 3.4 (3.5) | 72 (97) | 4 (4) |
| Exo84 | 2.5 (5.4) | 4.1 (4.0) | 75 (102) | 4 (9) |

[a]All alignments were carried out using the Dali server (42). Either the entire UL37N or just the helical bundle from the residues 1 to 136 (for which the data are given in parentheses) was used in the Dali search.

Example 2

A Surface-Exposed Region of the UL37 Protein that is Essential for Alphaherpesvirus Neuroinvasion Alphaherpesviruses are pathogens that proficiently invade the peripheral nervous system of their host. Although infections are not typically associated with significant symptoms, debilitating diseases including shingles, encephalitis and blindness can arise from the active replication of these viruses coupled with their ability to spread within neural circuits (Levitz R E. Herpes simplex encephalitis: A review. Heart Lung. 1998 May-June; 27(3):209-12; Lichtarge O, Bourne H R, Cohen F E. An evolutionary trace method defines binding surfaces common to protein families. J Mol Biol. 1996 Mar. 29; 257(2):342-58). Unfortunately, the viral factors that contribute to neuroinvasion remain largely unknown. Transport of herpesvirus capsids from the cell periphery to the nucleus is useful for viral replication. In neuronal cells this distance often spans the length of the axon, eliminating passive diffusion as a viable means of delivery. The UL37 protein is a member of a small subset of viral proteins that remain associated with capsids as they travel down the axon towards the nucleus to begin replication (Schmitz J B, Albright A G, Kinchington P R, Jenkins F J. The UL37 protein of herpes simplex virus type 1 is associated with the tegument of purified virions. Virology. 1995 Feb. 1; 206(2):1055-65). Viruses deficient in this protein either fail to propagate or demonstrate delays in transport of capsids to the nucleus prior to replication and in morphogenesis post-replication (Desai P, Sexton G L, McCaffery J M, Person S. A null mutation in the gene encoding the herpes simplex virus type 1 UL37 polypeptide abrogates virus maturation. J Virol. 2001 November; 75(21): 10259-71; Klupp B G, Granzow H, Mundt E, Mettenleiter T C. Pseudorabies virus UL37 gene product is involved in secondary envelopment. J Virol. 2001 October; 75(19): 8927-36; Krautwald M, Fuchs W, Klupp B G, Mettenleiter T C. Translocation of incoming pseudorabies virus capsids to the cell nucleus is delayed in the absence of tegument protein pUL37. J Virol. 2009 April; 83(7):3389-96). This supports an essential role for UL37 in the intracellular transport of capsids during infection. A UL37N crystal structure (UL37N is the amino terminal half of the protein) identified three conserved surface-exposed regions (Pitts J D, Klabis J, Richards A L, Smith G A, Heldwein E E. Crystal structure of the herpesvirus inner segment protein UL37 supports its essential role in control of viral trafficking. J Virol. 2014 May; 88(10):5462-73). The data demonstrated that pseudorabies virus (PRV) mutated in one of these regions, designated R2, is ablated in a critical neuroinvasion property: retrograde axon transport. Although R2 mutant particles fuse with the axon plasma membrane to release the viral capsid, these capsids are defective at initiating long distance retrograde axon transport towards the nucleus to begin genome replication. Despite this dramatic neural defect, the R2 mutant propagates with wild-type kinetics in epithelial cells (Pitts et al., supra). UL37 performs effector functions that are required specifically during neural delivery. The UL37 R2 region is essential for long distance retrograde motion in both in vivo and in vitro systems R2 mutant particles exhibit short non-processive motion in axons The non-processive movement of R2 mutant particles is not the result of retention of envelope or outer tegument proteins following fusion with the cell membrane Results are shown in FIGS. 9-12. FIG. 9 shows characterization of the neuroinvasive properties of the R2 mutant. As shown in FIG. 9A, the R2 region is essential for virulence in a mouse model of infection. CD-1 mice were infected by intranasal instillation of either wild-type (WT) PRV or PRV carrying mutations in the R1, R2, or R3 regions of the amino terminal portion of the UL37 protein. Mice infected with the R2 mutant did not present any symptoms of infection and were sacrificed at 240 hpi. A total of five mice were infected for each virus tested.

FIG. 9B shows that the R2 region is essential for retrograde mediated neuroinvasion. The eye anterior chamber of Long-Evans rats was injected with wild-type (WT) or R2 mutant PRV encoding a fluorescent reporter. In this model, wild-type PRV initially replicates in the iris and ciliary body then invades autonomic nerve endings to spread by retrograde axon transport to the superior cervical ganglion (SCG). By 48 hpi the wild-type PRV was detected in neurons in the SCG, Following infection with the R2 mutant virus was not observed in the SCG, images were taken at 120 hpi. FIG. 9C shows that the R2 region is dispensable for anterograde spread through neurons. For imaging of anterograde circuits virus was injected into the vitreous humor of the eye of the rat, which exposes the soma of retinal ganglion (RG) neurons to the inoculum. RG neurons project axons to the lateral geniculate nucleus (LGN) and superior colliculus (SC) therefore invasion of the LGN and SC by anterograde transport can be observed during infection. The R2 mutant was detected in both the SC and the LGN at 102 hpi. FIG. 9D shows That the R2 mutant does not travel retrograde down axons upon infection. Dorsal root ganglion (DRG) sensory neurons were isolated from embryonic chickens (embryonic day 8 [E8] to E10). Explants were cultured for three days prior to infection with $3.5 \times 10^7$ PFU/coverslip of both a RFP-tagged R2 mutant (R2) and a GFP-tagged wild-type (WT) virus. Mid segments of axons were imaged during the first hour post infection (hpi). The frequency of axon transport is reported as the average number of capsids entering the field of view per minute (error bars=SEM).

FIG. 10 shows that R2 mutant particles display aberrant non-processive motion. DRG explants were cultures as described in FIG. 9. FIG. 10A shows that mutation of the R2 region significantly increases the severity of stop and reversal events. Explants were infected were infected with $7.0 \times 10^7$ PFU/coverslip of either WT or R2 mutant virus and imaged at 3.5 hpi. Kymographs were generated using the Metamorph software package. Entire particle paths, whether moving, stalled, or reversing, were traced within the kymograph using the "Multi-line" tool. Fraction of time stopped and faction of time anterograde were calculated for each particle by dividing the total time the particle was either stopped or moving in the anterograde direction by the total time the particle was imaged. Greater than 30 particles were analyzed per virus for three replicate experiments and an average value calculated for each virus. Values reported represent the mean of the average values obtained. (error bars=SEM). FIG. 9B shows that aberrant motion of R2 mutant particles does not result in overall movement towards the soma. The average net displacement of all moving virus particles over a 10 second period was calculated. Inset image is a montage of six frames from a subregion of a time-lapse recording of the R2 mutant. Each frame is a 100 ms exposure representing every fifteenth frame of the original recording (the montage represents a 7.5 s time window). Retrograde motion of the particle is indicated with a red arrow while anterograde motion is shown with a white arrow (error bars=SEM).

FIG. 11 shows that motion of R2 particles does not result from endocytosis of virions or retention of outer tegument proteins following entry. Fusion of extracellular enveloped virions with the plasma membrane results in separation of the viral capsid from the envelope and the majority of tegument proteins. To examine the role of the R2 region in these events a R2 mutant virus was generated with RFP fused to the capsid and GFP fused to either the gD envelope protein or the VP13/14 or VP22 tegument proteins. These "dual-fluorescent" viruses allow for monitoring of capsid entry and tegument disassociation as determined by loss of the GFP signal. DRG explants were cultured as described in FIG. 9. Explants were infected were infected with $7.0 \times 10^7$ PFU/coverslip of the appropriate R2 mutant virus and imaged at 3.5 hpi. FIG. 11A shows that moving particles are not associated with the gD envelope protein or the outer tegument proteins VP22 and VP13/14. Moving particles were scored as either "Naked capsids": capsids lacking coincident GFP signal or as being associated with the respective GFP tagged protein gD (envelope), VP13/14, or VP22. Moving particles were defined as those that traveled >2.5 μm. Particles were tallied across two independent experiments with greater then three fields imaged per experiment. The fraction of the total number of moving particles that were positive for either only the RFP signal or both the RFP and GFP signals was calculated (error bars=SEM). FIG. 11B shows that non-moving particles are predominantly associated with envelope and tegument proteins. As described in panel (A) non-moving particles were scored as either "Naked capsids": capsids lacking coincident GFP signal or as being associated with the respective GFP tagged protein. Particles were tallied across two independent experiments with greater then three fields imaged per experiment. The fraction of the total number of non-moving particles that were positive for either only the RFP signal or both the RFP and GFP signals was calculated (error bars=SEM).

FIG. 12 shows modeling of wild-type and the R2 mutant trafficking in neuronal cells. The top view shows that herpesvirus replication occurs in the nucleus, this requires incoming particles to traverse the cytoplasm following entry into the cell. Wild-type virions fuse with the axon plasma membrane, which results in release of the capsid into the cell. Capsids travel along axonal microtubules towards the nucleus within the soma of the neuron (Sodeik B, Ebersold M W, Helenius A. Microtubule-mediated transport of incoming herpes simplex virus 1 capsids to the nucleus. J Cell Biol. 1997 Mar. 10; 136(5):1007-21). The bottom view shows that R2 mutant virions fuse with the plasma membrane of the axon however the released capsids alternate between motion towards (retrograde) and away (anterograde) from the soma. This "non-processive" motion prevents particles from reaching the soma to begin replication.

Example 3

Non-Neuroinvasive Herpesviruses for Vaccine and Oncolytic Vector Applications

This example describes a conserved feature in herpesviruses that, when mutated, eliminates the neuroinvasive property of the virus. This allows for the production of live-attenuated vaccine strains that lack the neuroinvasive property, thereby preventing the establishment of life-long infections while retaining the ability of the virus to replicate and spread in peripheral tissues to generate a robust sterilizing immune response.

Three conserved surface regions in the UL37 tegument protein were observed when the three dimensional structure of this protein was determined (Pitts et al., supra). Mutation of one of these regions (region 2) reduced the capacity of PRV to spread in epithelial cells, but did not impact its replication.

The important feature of the UL37 R2 mutants described herein is robust infection at the peripheral site of inoculation to produce a robust immune response and immune memory, with no involvement of the nervous system (which prevents establishment of life-long latent infections and subsequent complications).

Identifying the sites to mutate in related viruses (such as HSV and VZV) was a two step process. First, the crystal structure of PRV UL37 (Example 1) was used as a base model to map out the corresponding amino acids from the other viruses (homology modeling and structure model analysis). Second, the relevance of the positions was confirmed based on primary sequence alignments.

The mutations that destroy neuroinvasive properties are generally conserved in all alpha herpesviruses, but are unique to each virus (Table 3).

TABLE 3

Mutations to eliminate the virus neuroinvasive properties

| Human pathogens | |
|---|---|
| Herpes simplex virus types 1 & 2 | Q403A/E452A/Q455A/Q511A/R515A |
| Varicella zoster virus | Q363A/D413A/Q416A/Q472A/R476A |
| Veterinary pathogens | |
| Pseudorabies virus | Q324A/D362A/R365A/H421A/H425A |

PRV mutants with the above mutations were engineered (PRV-R2). FIG. 13 shows that PRV R2 lacks neuroinvasive properties. Mice were exposed to either wild type PRV (WT) or the PRV UL37 R2 mutant (R2) by eye injection, and neuroinvasion was assessed by isolating the superior cervical ganglion (SCG) that innervates the iris. Virus activity marked by glowing neurons in the WT infection are absent in the R2 infection.

FIG. 14 shows that PRV R2 is avirulent. Groups of five mice were infected with either wild-type PRV (WT) or PRV mutated in one of the UL37 surface regions. The region 2 (R2) mutant strain of PRV was avirulent. The mice infected with R2 displayed no symptoms or weight loss during the course of the experiment.

FIG. 15 shows that PRV R2 is a potent live-attenuated vaccine. Four mice were administered the PRV R2 neuroinvasive mutant on day 1 (x-axis). The weight of the animals in grams (y-axis) was monitored daily. On day 14, the animals received a lethal challenge of wild-type PRV (blue vertical line). The red vertical line indicates the maximum life-expectancy for unvaccinated animals. All four test animals survived to day 35 with only minimal fluctuations in weight.

Example 4

Non-Invasive Herpes Simplex Virus

A herpes simplex virus type 1 (HSV-1) non-invasive mutant encoding five codon changes in the R2 effector region of the pUL37 tegument protein: Q403A, E452A, Q455A, Q511A, R515A was engineered.

The HSV-1 pUL37 R2 mutant (HSV1-GS6298) was confirmed unable to enter the peripheral (trigeminal ganglion) and central (brain stem) nervous system of mice following inoculation into the periphery (eye; corneal scarification model) (FIG. 16). In addition, the R2 mutant also displayed attenuated spread in the cornea.

The R2 mutagenesis method results in HSV-1 lacking neuroinvasive properties, consistent with our original findings with PRV. This documents that a live-attenuated non-invasive vaccine strain of HSV-1 is useful. Furthermore, the neuroinvasive effector function of R2 is conserved in PRV and HSV-1, which is consistent with R2 functional conservation across the neuroinvasive herpesviruses given that the R2 sequence is conserved. Therefore, live-attenuated non-invasive vaccines of clinically- and agriculturally-relevant herpesvirus are produced using this technology (e.g., varicella-zoster virus, bovine herpesvirus, equine herpesvirus).

Example 5

R2 Mutation Design for Increased Safety

To simplify the production and stabilize R2 mutants, a new mutation design was developed based on an in-frame deletion and insertion of a 10 aa linker coding sequence (linker sequence: GSGSGSGSGS (SEQ ID NO: 21)). The linker was designed to span the cleft resulting from the deleted R2 region and thereby maintain proper folding of the pUL37 protein, based on predictions made from pUL37 structural data. Mutants of HSV-1 and PRV were produced, and the latter was tested in a vaccine model (FIG. 17).

An improved non-invasive design intended to prevent spontaneous reversion of the vaccine strain is able to protect mice from lethal PRV challenge.

All publications, patents, patent applications and accession numbers mentioned in the above specification are herein incorporated by reference in their entirety. Although the disclosure has been described in connection with specific embodiments, it should be understood that the disclosure as claimed should not be unduly limited to such specific embodiments. Indeed, various modifications and variations of the described compositions and methods of the disclosure will be apparent to those of ordinary skill in the art and are intended to be within the scope of the following claims.

We claim:

1. A variant herpesvirus or alphaherpes virus particle comprising at least one mutation in a UL37 protein, wherein said UL37 protein has at least 90% sequence identity to SEQ ID NO: 34 or SEQ ID NO: 35, wherein said at least one mutation is at one or more amino acid positions selected from the group consisting of Q403, E452, Q455, Q511, and R515, and wherein said virus particle exhibits reduced neuro-invasiveness relative to a virus particle lacking said mutation.

2. The virus particle of claim 1, wherein said virus is selected from the group consisting of herpes simplex virus-1 (HSV-1) and herpes simplex virus-2 (HSV-2).

3. The virus particle of claim 1, wherein said UL37 protein of said virus has at least 95% sequence identity to a sequence according to SEQ ID NO: 34 or SEQ ID NO: 35.

4. The virus particle of claim 1, wherein the ability of said virus to replicate in peripheral tissues is retained.

5. The virus particle of claim 1, wherein said at least one mutation is selected from Q403A, E452A, Q455A, Q511A, and R515A.

6. The virus particle of claim 1, wherein said at least one mutation is at two or more of said amino acid positions.

7. The virus particle of claim 1, wherein said at least one mutation is at three or more of said amino acid positions.

8. The virus particle of claim 1, wherein said at least one mutation is at four or more of said amino acid positions.

9. The virus particle of claim 1, wherein said at least one mutation is at all five of said amino acid positions.

10. The virus particle of claim 7, wherein said at least one mutation comprises Q403A, E452A, Q455A, Q511A, and R515A.

11. The virus particle of claim 1, wherein said virus is avirulent.

12. A nucleic acid encoding the virus particle of claim 1.

13. A vector comprising the nucleic acid of claim 12.

14. A pharmaceutical composition comprising the virus particle of claim 1, a nucleic acid encoding the virus particle of claim 1, or a vector comprising the nucleic acid encoding the virus particle of claim 1 and a pharmaceutically acceptable carrier.

15. A vaccine composition comprising the virus particle of claim 1, a nucleic acid encoding the virus particle of claim 1, or a vector comprising the nucleic acid encoding the virus particle of claim 1 and a pharmaceutically acceptable carrier.

16. A method of inducing an immune response against a virus, comprising:

administering the composition of claim 14 to a subject under conditions such that said subject generates an immune response to said virus.

17. The method of claim 16, wherein said subject is human or is a non-human animal.

18. A method of preventing infection by a virus, comprising:

administering the composition of claim 14 to a subject under conditions such that said subject generates an immune response to said virus.

19. A method of treating cancer, comprising:

administering the composition of claim 11 to a subject diagnosed with cancer under conditions such that the growth of said cancer is reduced.

20. The method of claim 19, wherein the composition is administered intravenously.

21. The method of claim 19, wherein the composition is administered in combination with an anti-cancer agent.

22. The method of claim 21, wherein said anti-cancer agent comprises an alkaloid, a covalent DNA-binding agent (alkylating agent), a noncovalent DNA-binding agent, an antimetabolite, an agent that induces tumor cell differentiation, or a platinum compound.

23. The method of claim 21, wherein said anti-cancer agent comprises an enzyme, a hormone, an antisense therapy technique, a hematopoietic growth factor, or an angiogenesis inhibitor.

24. The method of claim 21, wherein said anti-cancer agent comprises a proteosome inhibitor, an inhibitor of acetylation and/or methylation, a NF kappa B modulator, an inhibitor of cell cycle regulation, or a modulator of p53 protein function.

25. The method of claim 21, wherein said anti-cancer agent comprises an interferon, an interleukin, a tumor vaccine, or a monoclonal antibody conjugated with an anticancer drug, toxin, and/or radionuclide.

26. The method of claim 19, used in combination with radiation or adoptive immunotherapy.

* * * * *

```
                             SEQUENCE LISTING

<160> NUMBER OF SEQ ID NOS: 36

<210> SEQ ID NO 1
<211> LENGTH: 34
<212> TYPE: DNA
<213> ORGANISM: Artificial sequence
<220> FEATURE:
<223> OTHER INFORMATION: DNA Primer

<400> SEQUENCE: 1
gggaattcca tatgggcagc agccatcacc atca                                   34

<210> SEQ ID NO 2
<211> LENGTH: 30
<212> TYPE: DNA
<213> ORGANISM: Artificial sequence
<220> FEATURE:
<223> OTHER INFORMATION: DNA Primer

<400> SEQUENCE: 2
ttcaagacaa ggtccccggg cctagggatc                                        30

<210> SEQ ID NO 3
<211> LENGTH: 30
<212> TYPE: DNA
<213> ORGANISM: Artificial sequence
<220> FEATURE:
<223> OTHER INFORMATION: DNA Primer

<400> SEQUENCE: 3
ctagggatcc atggaagcac tggttcgtgc                                        30

<210> SEQ ID NO 4
<211> LENGTH: 29
<212> TYPE: DNA
<213> ORGANISM: Artificial sequence
<220> FEATURE:
<223> OTHER INFORMATION: DNA Primer

<400> SEQUENCE: 4
gtggctggcg cgtcggatct tcgaagatc                                         29

<210> SEQ ID NO 5
<211> LENGTH: 94
<212> TYPE: DNA
<213> ORGANISM: Artificial sequence
<220> FEATURE:
<223> OTHER INFORMATION: DNA Primer

<400> SEQUENCE: 5
ctcgccgaga acctggccgg cctggcgctg tggcgcctgc gccacgcctg ggccgcgggc       60
```
acggccccgc tgaggatgac gacgataagt aggg        94

<210> SEQ ID NO 6
<211> LENGTH: 97
<212> TYPE: DNA
<213> ORGANISM: Artificial sequence
<220> FEATURE:
<223> OTHER INFORMATION: DNA Primer

<400> SEQUENCE: 6
gtcgccgttg acgacccca ggagctccag cagcggggcc gtgcccgcgg cccaggcgtg        60
gcgcaggcgc cacaaccaat taaccaattc tgattag        97

<210> SEQ ID NO 7
<211> LENGTH: 88
<212> TYPE: DNA
<213> ORGANISM: Artificial sequence
<220> FEATURE:
<223> OTHER INFORMATION: DNA Primer

<400> SEQUENCE: 7
gtcggctgca cggcggtcgt cggcggcgtc gtgcaccgcc tcctcgccgc ctacgggccc        60
gggctgagga tgacgacgat aagtaggg        88

<210> SEQ ID NO 8
<211> LENGTH: 91
<212> TYPE: DNA
<213> ORGANISM: Artificial sequence
<220> FEATURE:
<223> OTHER INFORMATION: DNA Primer

<400> SEQUENCE: 8
cgcgacgtcc gtgtaggcgc gcacgtagtc cagcccgggc ccgtaggcgg cgaggaggcg        60
gtgcaccaac caattaacca attctgatta g        91

<210> SEQ ID NO 9
<211> LENGTH: 85
<212> TYPE: DNA
<213> ORGANISM: Artificial sequence
<220> FEATURE:
<223> OTHER INFORMATION: DNA Primer

<400> SEQUENCE: 9
ctcgaccaca cgcaggtgga cgccacgggc gtgtgggagg cggtggcggc cagcgcctcg        60
ccgaggatga cgacgataag taggg        85

<210> SEQ ID NO 10
<211> LENGTH: 88
<212> TYPE: DNA
<213> ORGANISM: Artificial sequence
<220> FEATURE:
<223> OTHER INFORMATION: DNA Primer

<400> SEQUENCE: 10
cgcggtcacg agcgcctcca cgacctgcag cggcgaggcg ctggccgcca ccgcctccca        60
caccaaccaa ttaaccaatt ctgattag        88

<210> SEQ ID NO 11
<211> LENGTH: 94
<212> TYPE: DNA
<213> ORGANISM: Artificial sequence
<220> FEATURE:
<223> OTHER INFORMATION: DNA Primer

<400> SEQUENCE: 11

```
gacctcctcg agcgcgccgt gctggaccgc gcgccccgcc tgacggccgc gcaggctgcc    60
gtcggctgca cgaggatgac gacgataagt aggg                                94
```

<210> SEQ ID NO 12
<211> LENGTH: 97
<212> TYPE: DNA
<213> ORGANISM: Artificial sequence
<220> FEATURE:
<223> OTHER INFORMATION: DNA Primer

<400> SEQUENCE: 12

```
gaggcggtgc acgacgccgc cgacgaccgc cgtgcagccg acggcagcct gcgcggccgt    60
caggcggggc gccaaccaat taaccaattc tgattag                             97
```

<210> SEQ ID NO 13
<211> LENGTH: 97
<212> TYPE: DNA
<213> ORGANISM: Artificial sequence
<220> FEATURE:
<223> OTHER INFORMATION: DNA Primer

<400> SEQUENCE: 13

```
ggggacgtga cggcggcgct ggggctcccc gagaagggcg tggaggccgt ggtgcgcgct    60
tgcatggcgc cgcgcaggat gacgacgata agtaggg                             97
```

<210> SEQ ID NO 14
<211> LENGTH: 100
<212> TYPE: DNA
<213> ORGANISM: Artificial sequence
<220> FEATURE:
<223> OTHER INFORMATION: DNA Primer

<400> SEQUENCE: 14

```
gcgcgccgcg cccacgtgct ccgtgggcgg gcgcggcgcc atgcaagcgc gcaccacggc    60
ctccacgccc ttctccaacc aattaaccaa ttctgattag                         100
```

<210> SEQ ID NO 15
<211> LENGTH: 88
<212> TYPE: DNA
<213> ORGANISM: Artificial sequence
<220> FEATURE:
<223> OTHER INFORMATION: DNA Primer

<400> SEQUENCE: 15

```
ctgccgctgg cgttggcggt gcgccagatg cagaacgagg gcctggcgca gctgacgcgc    60
gcgctcagga tgacgacgat aagtaggg                                       88
```

<210> SEQ ID NO 16
<211> LENGTH: 91
<212> TYPE: DNA
<213> ORGANISM: Artificial sequence
<220> FEATURE:
<223> OTHER INFORMATION: DNA Primer

<400> SEQUENCE: 16

```
gaagaactcg tcggcgatcg tgagggcaaa gagcgcgcgc gtcagctgcg ccaggccctc    60
gttctgcaac caattaacca attctgatta g                                   91
```

<210> SEQ ID NO 17

<210> SEQ ID NO 17
<211> LENGTH: 88
<212> TYPE: DNA
<213> ORGANISM: Artificial sequence
<220> FEATURE:
<223> OTHER INFORMATION: DNA Primer

<400> SEQUENCE: 17

```
aacccgacgc tgcgcgagca gttcgccgag gcggcgcggg ccgtggccgc ggcggcgctg    60
gtgcccagga tgacgacgat aagtaggg                                       88
```

<210> SEQ ID NO 18
<211> LENGTH: 91
<212> TYPE: DNA
<213> ORGANISM: Artificial sequence
<220> FEATURE:
<223> OTHER INFORMATION: DNA Primer

<400> SEQUENCE: 18

```
cgtgcgcggc gtggcgttga cctcgcccac gggcaccagc gccgccgcgg ccacggcccg    60
cgccgccaac caattaacca attctgatta g                                   91
```

<210> SEQ ID NO 19
<211> LENGTH: 92
<212> TYPE: DNA
<213> ORGANISM: Artificial sequence
<220> FEATURE:
<223> OTHER INFORMATION: DNA Primer

<400> SEQUENCE: 19

```
ccgaggcggc gcgggccgtg gacgaggcgg cgctggtgcc cgtgggcgag acgcaggtgg    60
acgccacggg aggatgacga cgataagtag gg                                  92
```

<210> SEQ ID NO 20
<211> LENGTH: 95
<212> TYPE: DNA
<213> ORGANISM: Artificial sequence
<220> FEATURE:
<223> OTHER INFORMATION: DNA Primer

<400> SEQUENCE: 20

```
gaggcgctgg cctgcaccgc ctcccacacg cccgtggcgt ccacctgcgt ctcgcccacg    60
ggcaccagcg caaccaatta accaattctg attag                               95
```

<210> SEQ ID NO 21
<211> LENGTH: 10
<212> TYPE: DNA
<213> ORGANISM: Artificial sequence
<220> FEATURE:
<223> OTHER INFORMATION: Linker sequence

<400> SEQUENCE: 21

```
gsgsgsgsgs                                                           10
```

<210> SEQ ID NO 22
<211> LENGTH: 424
<212> TYPE: PRT
<213> ORGANISM: Herpes virus

<400> SEQUENCE: 22

```
Met Glu Ala Leu Val Arg Ala Leu Glu Glu Ala Asp His Ala Val Ala
1               5                   10                  15

Thr Val Val Gln Ser Arg Ile Leu Glu Phe Phe Met Ala Ala Gly Arg
            20                  25                  30
```

Glu Thr Pro Ala Gly Val Arg Gly Leu Trp Ala Arg Ala Leu Arg Leu
       35                  40                  45

Ala Cys Arg Ala Tyr Val Glu Thr Gly Thr Cys Glu Ala Ala Val Leu
    50                  55                  60

Ala Glu Asn Leu Ala Gly Leu Ala Leu Trp Arg Leu Arg His Asp Trp
65                  70                  75                  80

Asp Glu Gly Thr Ala Pro Leu Leu Glu Leu Leu Gly Val Val Asn Gly
                85                  90                  95

Asp Asp Thr Thr Ala Ala Leu Thr Glu Ala Gly Leu Arg Thr Ser Ala
            100                 105                 110

Glu Phe Gly Pro Asp Ala Met Phe Arg Leu Val Ser Glu Trp Cys Ala
        115                 120                 125

Ala Phe Asp Glu Ala Leu Ala Gly Ala Arg Ser Ala Asp Asp Val Leu
    130                 135                 140

Ala Ala Pro Arg Val Val Pro Pro Glu Gln Thr Ala Arg Ala Leu Val
145                 150                 155                 160

Gln Pro Arg Phe Ala Thr Leu Tyr Asp Met Asp Phe Val Gln Asp Gly
                165                 170                 175

Leu Arg Tyr Val Ala Gln His Thr Asn Trp Ala Leu Pro Leu Ala Leu
            180                 185                 190

Ala Val Arg Gln Met Gln Asn Glu Gly Leu Lys Pro Leu Thr Arg Ala
        195                 200                 205

Leu Phe Ala His Gly Asp Ala Tyr Val Arg Glu Leu Arg Pro Gly Thr
    210                 215                 220

Val Ala Arg Arg Leu Arg Thr Asp Gln Gly Val Leu Ala Leu Leu Asp
225                 230                 235                 240

Pro Gly Ala Gln Ala Val His Val Ala Ala Ala Asp Leu Asp His
                245                 250                 255

Thr Gln Val Asp Ala Thr Gly Val Trp Glu Ala Val Gln Ala Ser Ala
                260                 265                 270

Ser Pro Leu Gln Val Val Glu Ala Leu Val Thr Ala Gly Phe Thr Arg
    275                 280                 285

Arg His Cys Asp Leu Leu Glu Arg Ala Val Leu Asp Arg Ala Pro Arg
    290                 295                 300

Leu Thr Asp Ala Gln Arg Ala Val Gly Cys Thr Ala Val Val Gly Gly
305                 310                 315                 320

Val Val His Arg Leu Leu Asp Asp Tyr Gly Pro Gly Leu Asp Tyr Val
                325                 330                 335

Arg Ala Tyr Thr Asp Val Ala Asp Thr Leu Glu Pro Leu Tyr Gly Asp
            340                 345                 350

Val Thr Ala Ala Leu Gly Leu Pro Glu Lys Gly Val Glu His Val Val
        355                 360                 365

Arg His Cys Met Ala Pro Arg Pro Thr Glu His Val Gly Ala Ala
    370                 375                 380

Arg Ala Ala Leu Leu Arg Glu Val Ala Ala Glu Arg Ala Gly
385                 390                 395                 400

Leu Ala His Ser Ala Ala Arg Glu Ala Leu Asn Thr Trp Leu Ala Phe
                405                 410                 415

Arg Ala Gln Ser Arg Trp Gly Leu
            420

<210> SEQ ID NO 23
<211> LENGTH: 537

<212> TYPE: PRT
<213> ORGANISM: Bovine herpesvirus

<400> SEQUENCE: 23

```
Met Ser Gly Asp Pro Val Arg Ala Leu Trp Ala Ala Leu Glu Arg Leu
1               5                   10                  15

Asp Gly Glu Val Ala Gly Pro Ala Ala Leu Ala Glu Ala Arg Ala Ala
            20                  25                  30

Val Ser Glu Phe Leu Leu Ala Ser Gly Pro Ser Ser Leu Asp Phe Val
        35                  40                  45

Ala Pro Arg Trp Ala Ala Leu Gln Arg Ala Ala Cys Arg Ala Tyr Glu
    50                  55                  60

Arg Leu His Thr Pro Asp Ala Ala Leu Leu Ala Glu Asn Leu Pro Gly
65                  70                  75                  80

Leu Val Leu Trp Arg Leu Pro Gly Ala Ala Arg Asp Thr Ala Asp Phe
                85                  90                  95

Met Ala Gly Val Arg Asp Leu Ala Asn Ser Met Ile Ala Glu Ala Pro
            100                 105                 110

Leu Gly Tyr Leu Ala Ala Ala Arg Leu Arg Ala Thr Ala Ala Phe Gly
        115                 120                 125

Pro Val Asn Met Gln Arg Val Val Glu Trp Ala Ser Leu Phe Leu
130                 135                 140

Glu Ile Tyr Ala Arg Glu Asp Ala Ala Cys Val Gly Val Leu Gly Pro
145                 150                 155                 160

Asp Pro Ala Cys Arg Ser Pro Ala Gly Ser Ala Ala Val Ile Arg Pro
                165                 170                 175

Leu Leu Gln Ser Arg Phe Arg Leu Leu Tyr Asp Met Pro Phe Phe Gln
            180                 185                 190

Ala Gly Leu Ser Ala Leu Ala His Ala Ala Asn Trp Lys Val Pro Met
        195                 200                 205

Ala Ala Val Ala Arg Arg Ala Ala Asp Ala Ala Ala Pro Pro Leu Ala
    210                 215                 220

Arg Ala Leu Phe Ala Val Ala Leu Val Asp Glu Tyr Phe Pro Glu Pro
225                 230                 235                 240

Asp Asp Glu Asp Thr Ala Pro Gly Leu Ala Glu Ala Phe Ala Glu Ile
                245                 250                 255

Ala Asp Leu Val Pro Pro Glu Ala Leu Val Pro Ala Gly Glu Ala Asn
            260                 265                 270

Ala Phe Ala Arg Ser Ser His Asp Val Arg Val Ser Ala Ala Leu Ala
        275                 280                 285

Tyr Arg Asp Pro Phe Val Arg Gly Ala Ala Gly Ser Val Ala Ala
    290                 295                 300

Arg Val Arg Ala Asp Gly Leu Leu Ala Asp Asp Thr Leu Leu Gly
305                 310                 315                 320

Arg Asp Ala Val Ala Val His Ala Gly Ala Val Val Arg Leu Leu Glu
                325                 330                 335

Arg Ala Ala Ala Arg Ala Thr Pro Ala Ala Leu Gly Arg Val Ala Glu
            340                 345                 350

His Ala Ala Ala Val Trp Asp Ala Val Gln Ala Ser Ala Thr Pro Asp
        355                 360                 365

Gln Ala Val Glu Thr Leu Ala Ala Ala Gly Phe Thr Pro Gly Thr Cys
    370                 375                 380

Ala Met Leu Glu Arg Ala Val Leu Ala Gln Leu Ser Arg Pro Glu Pro
385                 390                 395                 400
```

Arg Ala Pro Ala Asp Val Leu Gln Ala Val Gly Cys Val Ala Val Ala
            405                 410                 415

Gly Gly Val Leu Phe Lys Leu Phe Asp Ala Tyr Gly Pro Ser Ala Asp
            420                 425                 430

Tyr Leu Ala His Tyr Thr Ala Thr Ile Ala Asn Leu His Pro Tyr Tyr
            435                 440                 445

Ala Asp Val Leu Pro Leu Leu Gly Leu Pro Asp Gly Gly Leu Glu Gln
            450                 455                 460

Thr Ile Arg His Cys Met Ala Pro Arg Pro Arg Thr Asp Tyr Val Ala
465                 470                 475                 480

Ala Ile Arg Ala Ala Leu Ala Ala Glu Ala Ala Ala Asp Lys Arg
            485                 490                 495

Ala Ala Ser Ala Ser Ala Arg Ala Ala Val Glu Asn Ser Gly Asp Arg
            500                 505                 510

Ala Ala Ala Gly Ala Ala Arg Glu Ala Leu Leu Thr Trp Phe Asp
            515                 520                 525

Leu Arg Ala Ser Glu Arg Trp Gly Val
        530                 535

<210> SEQ ID NO 24
<211> LENGTH: 541
<212> TYPE: PRT
<213> ORGANISM: Equine herpesvirus

<400> SEQUENCE: 24

Met Ala Arg Glu Asp Trp Ser Met Arg Ala Leu Val Asn Thr Leu Ala
1               5                   10                  15

Gly Leu Leu Gly Glu Thr Asp Thr Asp Val Thr Ser Met Glu Pro Ala
            20                  25                  30

Met Leu Met Val Leu Lys Ser Ser Ile Ser Glu Phe Phe Leu Ser Thr
        35                  40                  45

Asp Thr Val Ser Val Glu Glu Ala Ala Glu Leu Phe Pro Arg Leu Gln
    50                  55                  60

Phe Leu Ala Cys Arg Ala Tyr Ala Ala Ser His Thr Pro Glu Ala Ala
65                  70                  75                  80

Met Leu Ala Glu Asn Leu Ser Gly Leu Val Leu Trp Arg Ile His Gln
                85                  90                  95

Asn Trp Thr Asp Arg Glu Thr Glu Ala Val Asp Gln Met Phe Val Leu
            100                 105                 110

Leu Glu Ile Met Asn Gly Glu Ser Gly Val Tyr Met Leu Ser Asn Asn
        115                 120                 125

Asn Leu Arg Ile Ser Ala Lys Tyr Gly Pro Ser Asn Met His Leu Met
    130                 135                 140

Val Ser Thr Trp Leu Gly Thr Phe Arg Asn Val Met Leu Ser Ile Ala
145                 150                 155                 160

Asn Thr Thr Pro Asp Ala Met Phe Asn Ala Arg Arg Ile Glu Ala Ile
                165                 170                 175

Glu Glu Phe Ser Lys Pro Leu Val His Lys Arg Phe Asp Leu Ile Tyr
            180                 185                 190

Asp Met Pro Phe Val Gln Glu Gly Leu Arg Ile Val Ala Ala Lys Ile
        195                 200                 205

Asn Trp Leu Leu Pro Phe Gly Leu Ile Ala Lys Arg Ser Lys Asp Thr
    210                 215                 220

Ser Met Ala Pro Leu Thr Arg Ala Leu Phe Leu Leu Ser Leu Val Asp

```
            225                 230                 235                 240
Ser Tyr Phe Pro Lys Gly Thr Ala Thr Asn Ser Ser Met Lys Ala Leu
                245                 250                 255

Thr Ile Tyr Phe Arg Glu Ile Val Arg Asn Ile Asp Asn Ser Ala Phe
            260                 265                 270

Val Pro Val Thr Glu Val Asn Ala Thr Pro Arg Thr Ala Tyr Glu Val
                275                 280                 285

Arg Val Ser Ser Ala Ile Val His Gln Asn Pro Tyr Val Thr Asp Thr
            290                 295                 300

Lys Ala Gly Met Val Ala Glu Arg Val Arg Thr Asp Ala Glu Ile Leu
305                 310                 315                 320

Ser Ser Gly Ala Leu Leu Ser Ser Gly Ala Leu Ser Ala His Val Thr
                325                 330                 335

Ala Val Ala Lys Leu Leu Ala Phe Asn Asp Gln Asn Asp Thr Ser Ser
            340                 345                 350

Val Ala Arg Ala Arg Val Ala Glu His Ala Ser Asn Thr Trp Glu Ala
                355                 360                 365

Ile Gln Ala Ser Thr Thr Pro Ala Gln Val Val Glu Ala Leu Val Thr
            370                 375                 380

Ala Gly Phe Thr Ser Thr His Cys Gly Ile Leu Glu Arg Val Val Val
385                 390                 395                 400

Asp Tyr Phe Thr Arg Leu Arg Ser Thr Ala Glu Ser Arg Pro Gly Gln
                405                 410                 415

Asp Asn Ser Leu Asp Tyr Ala Gln Gln Val Val Gly Cys Val Ser Ile
            420                 425                 430

Val Gly Gly Val Val Phe Arg Leu Leu Met Ser Tyr Gly Phe Gly Leu
                435                 440                 445

Asp Tyr Ile Arg Asp Tyr Thr Thr Thr Ile Ser Thr Leu Glu Pro Val
            450                 455                 460

Tyr Asn Glu Leu Leu Leu Ala Leu Gly Leu Ala Asp Lys Gly Val Glu
465                 470                 475                 480

Gln Thr Leu Arg Arg Ser Met Ala Pro Arg Pro Tyr Met Asn Tyr Ile
                485                 490                 495

Ser Ala Ala Arg Ala Ala Leu Asp Asn Glu Leu Leu Ile Val Glu Lys
            500                 505                 510

Arg Thr Thr Gly Pro Gly Thr His Ser Ala Ala Arg Glu Ser Leu Leu
            515                 520                 525

Thr Trp Phe Asp Phe Arg Ala Arg Asp Arg Trp Gly Val
            530                 535                 540

<210> SEQ ID NO 25
<211> LENGTH: 540
<212> TYPE: PRT
<213> ORGANISM: Herpes virus

<400> SEQUENCE: 25

Met Asp Asn Ser Gly Pro Leu Met Thr Leu Val Ala Ser Leu Glu Gly
1               5                   10                  15

Leu Val Gly Val Ala Ser Asp Arg Leu Thr Gln Asp Gly Val Leu Arg
                20                  25                  30

Ile Lys Ser Met Ile Ser Glu Phe Phe Leu Ser Thr Asp Ser Ile Glu
            35                  40                  45

Leu Arg Asp Thr Gln Arg Leu Trp Ala Lys Leu Gln Lys Leu Ala Cys
50                  55                  60
```

-continued

```
Asp Ala Tyr Leu His Thr Arg Ser Pro Glu Thr Ala Phe Leu Ala Glu
 65                  70                  75                  80

Asn Leu Pro Gly Leu Ile Phe Trp Arg Phe Lys His Asp Trp Thr Glu
             85                  90                  95

Ser Pro Ile Asn Asp Leu Thr Asp Ile Ser Thr Leu Leu Asp Val Met
        100                 105                 110

Asn Asp Glu Glu Cys Met Ala Cys Ile Thr Thr Ala Gly Leu Arg Val
    115                 120                 125

Ser Ser Phe Leu Gly Pro Ser Asn Ile Tyr Arg Leu Val Ser Glu Trp
130                 135                 140

Ile Val Leu Phe Lys Glu Ile Tyr Leu Gly Val Leu Asn Lys Thr Pro
145                 150                 155                 160

Ser Asp Ala Leu Asn Glu Pro Pro Ile Ser Ser Leu Asp Lys Phe Ser
                165                 170                 175

Glu Pro Leu Val Ser Lys Lys Phe Glu Leu Leu Tyr Gly Met Pro Phe
            180                 185                 190

Val Gln Glu Gly Leu Arg Val Ile Ala Ile Arg Ala Asn Trp Leu Val
        195                 200                 205

Gln Phe Gly Val Met Val Gln Arg Thr Arg Asp Ser Thr Leu Thr Pro
    210                 215                 220

Leu Thr Arg Ala Leu Tyr Met Leu Ala Leu Val Asp Glu Tyr Phe Gln
225                 230                 235                 240

Asp Ile Glu Gln Thr Ser Thr Tyr Thr Thr Leu Val Arg Asp Phe Leu
                245                 250                 255

Glu Leu Thr Gln Glu Ile Asp Glu Gly Ala Leu Val Pro Leu Gln Ala
            260                 265                 270

Ala Asn Leu Ser Pro Arg Thr Ala Tyr Glu Val Arg Ile Ser Ser Ala
        275                 280                 285

Ile Ala His Gln Asn Pro Phe Ile Thr Asn Pro Gln Pro Gly Thr Val
    290                 295                 300

Thr Val Arg Leu Arg Thr Asp Pro Glu Ile Leu Thr Glu Arg His Leu
305                 310                 315                 320

Asn Leu Glu Ala Leu Leu Ile His Val Thr Ala Ile Ile Arg Leu Leu
                325                 330                 335

Asp Ser Lys Asp Ile Thr Tyr Glu Asp Gly Ser Asn Thr Ile Trp Asn
            340                 345                 350

Tyr Val Glu Cys Thr Thr Asn Thr Trp Glu Val Ile Gln Ala Ser
        355                 360                 365

Thr Asn Pro His Gln Ala Ile Glu Ala Leu Ile Gln Ala Gly Phe Thr
    370                 375                 380

Ser Phe His Cys Ser Met Leu Glu Arg Ala Ile Ser Asp Lys Phe Ser
385                 390                 395                 400

Lys Ala Arg Ile Ser Asn Ile Asn Arg His Ser Ile Gln Arg Pro Leu
                405                 410                 415

Leu Asp Glu Ala Gln Gln Ala Ile Gly Cys Val Ala Met Val Gly Ser
            420                 425                 430

Leu Ile Phe Lys Leu Val Thr His Tyr Gly Asn Gly Leu Asp Tyr Ile
        435                 440                 445

Arg His Tyr Thr Thr Thr Leu Ala Asp Leu Pro Leu Val Tyr Gly Asp
    450                 455                 460

Leu Leu Asp Ser Leu Gly Leu Pro Asn Gly Ser Val Glu Gln Ile Ile
465                 470                 475                 480

Arg His Cys Met Ala Pro Lys Pro Tyr Ile Asp Tyr Ile Thr Asn Ser
```

```
                        485                 490                 495
Arg Val Val Phe Glu Thr Glu Leu Asn Leu Val Asp Gln Arg Val Val
                500                 505                 510

Thr Val Glu Gly Asn Thr His Asn Ala Ala Arg Glu Ser Leu Leu Met
                515                 520                 525

Trp Phe Asp Phe Lys Ala Arg Asp Leu Trp Gly Ile
                530                 535                 540

<210> SEQ ID NO 26
<211> LENGTH: 553
<212> TYPE: PRT
<213> ORGANISM: Herpes virus

<400> SEQUENCE: 26

Met Trp Phe Asp Val Phe Cys Ile Val His Pro Thr Val Asp Ile Met
1               5                   10                  15

Glu Thr Ala Ile Thr Gln Asn Leu Leu Asn Asp Leu Lys Ser Leu Ser
                20                  25                  30

Ser Lys Asp Asp Ser Ser Glu Thr Ile Trp Pro Glu Lys Val Glu
            35                  40                  45

Thr Ala Arg Ile Ser Ile Val Lys Phe Leu Arg Ser Thr Gln Glu Ile
        50                  55                  60

Pro Leu Glu Asn Thr Leu Trp Thr Glu Leu His Lys Val Ile Cys Asn
65                  70                  75                  80

Val Tyr Ala His Thr Phe Leu Ile Glu Ala Ser Phe Leu Ala Glu Asn
                85                  90                  95

Leu Pro Gly Leu Ile Phe Trp Lys Leu Glu Ser His Cys Thr Gln Asn
            100                 105                 110

Val Met Gln His Met Glu Thr Leu Lys Gln Leu Cys Asn Asn Ile Gln
        115                 120                 125

Ser Arg Glu Thr Leu Gln Arg Leu Thr Leu His Ser Leu Arg Thr Ser
130                 135                 140

Ala Lys Leu Gly Pro Val Ser Ile Asn Ser Leu Val Thr Asp Trp Ile
145                 150                 155                 160

Asn Met Phe Glu Val Ala Val Arg Asp Ile Asn Glu Ala Thr Lys Leu
                165                 170                 175

Pro Phe Leu Tyr Ala Arg Gln Gly Met Val Glu Ser Ala Val Ala Ala
            180                 185                 190

Leu Thr His Gln Arg Phe Ala Leu Leu Tyr Asp Met Pro Ile Val Gln
        195                 200                 205

Asp Gly Leu Arg Ile Leu Thr Gln Arg Ala Ser Trp Leu Ile Pro Phe
210                 215                 220

Thr Ile Met Trp Ser His Ile Gln Ser Asp Ser Phe Thr Pro Leu Thr
225                 230                 235                 240

Lys Cys Leu Phe Ile Ile Asn Leu Ala Asp Glu Tyr Phe Asp Thr
                245                 250                 255

Pro Val Ser Tyr Leu Thr Asp Leu Phe Asn Asp Asn Ile Ile His Val
            260                 265                 270

Lys Asp Ile Ala Phe Val Pro Ile Glu Glu Ala Ile Val Gln Ala Thr
        275                 280                 285

Thr Val His Gly Ala Arg Ile Asn Ala Ala Leu Ala His Gln Asn Leu
    290                 295                 300

Ser Ile Arg Gln Thr Gln Pro Gly Thr Ala Thr His Arg Leu Arg Val
305                 310                 315                 320
```

```
Asp Val Asn Ile Trp Asp Asn Asn Ile Leu Ser Leu Ser Ala Pro Gly
                325                 330                 335

Ile His Ile Asp Gly Leu Leu His Leu Ile Thr Thr Asp Pro Thr Ala
            340                 345                 350

Glu Thr Thr Ala Gly Ala Ala Val Ala Glu Cys Val Arg Val Ala Trp
            355                 360                 365

Glu Arg Val Gln Ala Ser Thr Ser Pro Asn Ser Leu Val Leu Ala Leu
        370                 375                 380

Leu Glu Ala Gly Phe Thr Arg Tyr Thr Cys Lys Leu Leu Arg Lys Phe
385                 390                 395                 400

Val Thr His Cys Thr Leu Gly Leu His Ser Leu Tyr Asp Thr His Ile
                405                 410                 415

Thr His Glu Val Cys Lys Leu Thr Asp Phe Gln Gln Thr Ile Gly Cys
            420                 425                 430

Val Ser Leu Val Gly Gly Leu Ala Tyr Gln Leu Leu Glu Thr Tyr Ala
        435                 440                 445

Pro Thr Ala His Tyr Val Ser Thr Tyr Thr His Ile Leu Ser Glu Thr
    450                 455                 460

Glu Lys Arg Tyr Glu Thr Leu Ile Pro Ala Leu Gly Leu Pro Pro Gly
465                 470                 475                 480

Gly Leu Gly Gln Ile Met Arg Arg Cys Phe Ala Pro Arg Pro Leu Ile
                485                 490                 495

Ser Ser Ile Gln Leu Ala Arg Lys Thr Leu Val Glu Glu Ile Asn Thr
            500                 505                 510

Ala Glu Thr Arg Lys Thr Val Leu His Leu Gln His Thr Arg Glu Thr
        515                 520                 525

Gln Pro Gly Ala Arg Val Thr Arg Glu Ala Ile Leu Thr Trp Phe Asp
    530                 535                 540

Phe Arg Met Glu Ser Arg Trp Gly Ile
545                 550

<210> SEQ ID NO 27
<211> LENGTH: 547
<212> TYPE: PRT
<213> ORGANISM: Herpes virus

<400> SEQUENCE: 27

Met Glu Glu Pro Ile Cys Tyr Asp Thr Gln Lys Leu Leu Asp Asp Leu
1               5                   10                  15

Ser Asn Leu Lys Val Gln Glu Ala Asp Asn Glu Arg Pro Trp Ser Pro
            20                  25                  30

Glu Lys Thr Glu Ile Ala Arg Val Lys Val Val Lys Phe Leu Arg Ser
        35                  40                  45

Thr Gln Lys Ile Pro Ala Lys His Phe Ile Gln Ile Trp Glu Pro Leu
    50                  55                  60

His Ser Asn Ile Cys Phe Val Tyr Ser Asn Thr Phe Leu Ala Glu Ala
65                  70                  75                  80

Ala Phe Thr Ala Glu Asn Leu Pro Gly Leu Leu Phe Trp Arg Leu Asp
                85                  90                  95

Leu Asp Trp Thr Ile Glu Glu Pro Gly Asn Ser Leu Lys Ile Leu Thr
            100                 105                 110

Gln Leu Ser Ser Val Val Gln Asp Ser Glu Thr Leu His Arg Leu Ser
        115                 120                 125

Ala Asn Lys Leu Arg Thr Ser Ser Lys Phe Gly Pro Val Ser Ile His
    130                 135                 140
```

-continued

Phe Ile Ile Thr Asp Trp Ile Asn Met Tyr Glu Val Ala Leu Lys Asp
145                 150                 155                 160

Ala Thr Thr Ala Ile Glu Ser Pro Phe Thr His Ala Arg Ile Gly Met
                165                 170                 175

Leu Glu Ser Ala Ile Ala Ala Leu Thr Gln His Lys Phe Ala Ile Ile
            180                 185                 190

Tyr Asp Met Pro Phe Val Gln Glu Gly Ile Arg Val Leu Thr Gln Tyr
        195                 200                 205

Ala Gly Trp Leu Leu Pro Phe Asn Val Met Trp Asn Gln Ile Gln Asn
    210                 215                 220

Ser Ser Leu Thr Pro Leu Thr Arg Ala Leu Phe Ile Ile Cys Met Ile
225                 230                 235                 240

Asp Glu Tyr Leu Thr Glu Thr Pro Val His Ser Ile Ser Glu Leu Phe
                245                 250                 255

Ala Asp Thr Val Asn Leu Ile Lys Asp Glu Ala Phe Val Ser Ile Glu
            260                 265                 270

Glu Ala Val Thr Asn Pro Arg Thr Val His Glu Ser Arg Ile Ser Ser
        275                 280                 285

Ala Leu Ala Tyr Arg Asp Pro Tyr Val Phe Glu Thr Ser Pro Gly Met
    290                 295                 300

Leu Ala Arg Arg Leu Arg Leu Asp Asn Gly Ile Trp Glu Ser Asn Leu
305                 310                 315                 320

Leu Ser Leu Ser Thr Pro Gly Ile His Ile Glu Ala Leu Leu His Leu
                325                 330                 335

Leu Asn Ser Asp Pro Glu Ala Glu Thr Thr Ser Gly Ser Asn Val Ala
            340                 345                 350

Glu His Thr Arg Gly Ile Trp Glu Lys Val Gln Ala Ser Thr Ser Pro
        355                 360                 365

Ser Met Leu Ile Ser Thr Leu Ala Glu Ser Gly Phe Thr Arg Phe Ser
    370                 375                 380

Cys Lys Leu Leu Arg Arg Phe Ile Ala His His Thr Leu Ala Gly Phe
385                 390                 395                 400

Ile His Gly Ser Val Val Ala Asp Glu His Ile Thr Asp Phe Gln Gln
                405                 410                 415

Thr Leu Gly Cys Leu Ala Leu Val Gly Gly Leu Ala Tyr Gln Leu Val
            420                 425                 430

Glu Thr Tyr Ala Pro Thr Thr Glu Tyr Val Leu Thr Tyr Thr Arg Thr
        435                 440                 445

Val Asn Glu Thr Glu Lys Arg Tyr Glu Thr Leu Leu Pro Ala Leu Gly
    450                 455                 460

Leu Pro Pro Gly Gly Leu Gly Gln Ile Met Arg Arg Cys Phe Ala Pro
465                 470                 475                 480

Arg Pro Leu Ile Glu Ser Ile Gln Ala Thr Arg Val Ile Leu Leu Asn
                485                 490                 495

Glu Ile Ser His Ala Glu Ala Arg Glu Thr Thr Tyr Phe Lys Gln Thr
            500                 505                 510

His Asn Gln Ser Ser Gly Ala Leu Leu Pro Gln Ala Gly Gln Ser Ala
        515                 520                 525

Val Arg Glu Ala Val Leu Thr Trp Phe Asp Leu Arg Met Asp Ser Arg
    530                 535                 540

Trp Gly Ile
545

<210> SEQ ID NO 28
<211> LENGTH: 545
<212> TYPE: PRT
<213> ORGANISM: Herpes virus

<400> SEQUENCE: 28

```
Met Ser Ala Val Thr Thr Asp Glu Ile Trp Pro Leu Lys Val Leu Leu
1               5                   10                  15

Asp Thr Leu Arg Ser Leu Ser Ser Arg Thr Ser Pro Thr Glu Pro Trp
            20                  25                  30

Gly Ala Thr Ala Thr Ala Glu Ala Arg Ala Ala Ile Gly Ser Phe Phe
        35                  40                  45

Leu Ala Ser Gly Thr Met Ser Ile Leu Gln Val Glu Leu Thr Trp Arg
    50                  55                  60

Asp Thr Phe Ser Ala Ile Leu Glu Val Tyr Lys Gln Thr Arg Ser Pro
65                  70                  75                  80

Glu Ala Ser Met Leu Ala Gln Asn Phe Val Gly Leu Ile Leu Trp Arg
                85                  90                  95

Ile Ser Val Arg Trp Asp Lys Thr Ser Trp Gln Glu Asn Ser His Arg
            100                 105                 110

Leu Arg Arg Leu Val Ala Glu Met Thr Gly Glu Glu Ala Ile Ser Trp
        115                 120                 125

Leu Ser Arg Asn Asn Leu Arg Ile Ser Ala Pro Phe Gly Pro Ser Val
    130                 135                 140

Met Trp Pro Leu Ile Ser Glu Trp Phe Ala Val Phe Glu Asp Ala Ala
145                 150                 155                 160

Asn His Ala Phe Thr Tyr Thr Pro Glu His Leu Leu Ser Glu Arg Glu
                165                 170                 175

Phe Ser Phe Asn Val Gly Asp Leu Ala Ala Ser Leu Ala His Lys Arg
            180                 185                 190

Phe Glu Leu Ile Tyr Asp Phe Pro Phe Val Gln Glu Gly Ile Arg Leu
        195                 200                 205

Val Ser Ile Ala Ser Gly Trp Ile Ala Pro Phe Val Ile Met Tyr Arg
    210                 215                 220

Cys Thr Thr Asn Arg Val Phe Thr Pro Leu Thr Arg Ile Leu Phe Thr
225                 230                 235                 240

Ile Ala Leu Val Asp Gln Tyr Phe Arg Gly Leu His Ala Pro Gln Pro
                245                 250                 255

Phe Gln Ile Lys Asp Arg Phe Ala Glu Asp Val Gly Ala Leu Gly Ser
            260                 265                 270

Lys Glu Leu Ile Pro Ala Leu Glu Ala Asn Ser Thr Lys Arg Thr Ser
        275                 280                 285

Tyr Glu Val Arg Ala Ser Ala Ile Ala Tyr Glu Ser Pro Phe Val
    290                 295                 300

His Thr Ile Gln Pro Gly Met Ala Ala Asp Lys Leu Arg Asn Gly Ser
305                 310                 315                 320

Asp Ile Ile Met Ser Asp Thr Ser Leu Thr Glu Asp Ser Leu Ala Ile
                325                 330                 335

His Leu Ser Ala Val Leu Arg Leu Ile Ser Asp Ile Gly Leu Glu Glu
            340                 345                 350

Asp Asn Gly Ala Ile Asp Ala Ala Lys Ala Lys Leu Ser Asn Ser Ala
        355                 360                 365

Arg Arg Ala Trp Asp Ala Ile Gln Tyr Ser Ser Ser Pro Lys Gln Leu
    370                 375                 380
```

```
Leu Glu Ala Leu Ile Glu Arg Gly Phe Val Arg Gln Val Cys Arg Ala
385                 390                 395                 400

Tyr Glu Ser Ala Leu Lys Thr Tyr Phe Thr Arg Asn Tyr Gly Ser Val
            405                 410                 415

Asp Glu Gly Asp Ile Phe Asp Asp Val Gln Gln Val Gly Cys Val
            420                 425                 430

Ala Val Ile Gly Asn Val Val Phe Gly Leu Ile Glu Ser Tyr Gly Pro
            435                 440                 445

Gly Met Thr Tyr Leu Ser Asn Tyr Met Glu Asn Cys Val Ile Ser Glu
        450                 455                 460

Ser Asp Ser His Phe Ile Glu Ala Leu Gly Leu Glu Arg Ala Ile Ile
465                 470                 475                 480

Ser Gln Ile Ile Gly Arg Cys Ile Pro Pro Ile Pro His Glu Asp Tyr
                485                 490                 495

Ile Lys Ala Ala Arg Ala Val Leu Val Ala Glu Met Asp His Val Ala
            500                 505                 510

Ser Lys Ser Glu Ala Val Gly Phe Arg Gln Ser Ile Arg Ser Ala Lys
            515                 520                 525

Glu Ser Leu Met Leu Trp Phe Asp Asn Arg Ala Asn Glu Ile Trp Gly
    530                 535                 540

Ile
545

<210> SEQ ID NO 29
<211> LENGTH: 539
<212> TYPE: PRT
<213> ORGANISM: Herpes virus

<400> SEQUENCE: 29

Met Ser Glu Thr Gln Gly Glu Ala Arg Phe Pro Leu Lys Thr Leu Leu
1               5                   10                  15

Asp Thr Leu Arg Ser Leu Ser Ala Gly Thr Ala Pro Leu Glu Pro Trp
            20                  25                  30

Gly Asn Ala Thr Ala Ala Glu Ala Arg Thr Ala Ile Gly Ser Phe Phe
        35                  40                  45

Gln Ala Leu Glu Thr Met Ser Ile Gln Gln Val Glu Ser Thr Trp Arg
    50                  55                  60

Asp Ala Phe Ala Ala Val Leu Glu Val Tyr Lys Gln Thr Gly Ser Pro
65                  70                  75                  80

Glu Ala Ala Met Leu Ala Gln Asn Phe Val Gly Phe Ile Leu Trp Arg
                85                  90                  95

Thr Ser Val Arg Trp Asp Lys Met Ser Trp Lys Asp Asp Ser Arg Arg
            100                 105                 110

Leu Arg Arg Leu Ala Ala Glu Met Thr Gly Glu Glu Ala Ile Ala Trp
        115                 120                 125

Leu Thr Arg Asn Gly Leu Arg Arg Ser Cys Pro Phe Gly Pro Ser Val
    130                 135                 140

Leu Trp Pro Leu Ile Ser Glu Trp Leu Thr Ile Phe Glu Glu Ile Ala
145                 150                 155                 160

Thr Asp Ala Phe Asp Tyr Thr Ser Glu Gly Leu Leu Ser Gly Arg Gln
                165                 170                 175

Pro Ala Pro Asn Ala Leu Glu Leu Pro Ala Ser Leu Thr Gln Thr Arg
            180                 185                 190

Phe Lys Leu Ile Tyr Asp Phe Pro Phe Val Gln Glu Gly Ile Arg Leu
```

```
            195                 200                 205
Ile Ser Ile Ala Val Gly Trp Ile Thr Pro Phe Val Ile Met Ser Arg
210                 215                 220

Cys Thr Thr Asn Arg Ala Phe Thr Pro Leu Thr Arg Ile Leu Phe Thr
225                 230                 235                 240

Leu Ala Leu Val Asp Gln Tyr Phe Lys Ser Pro Arg Ser Pro His Pro
                245                 250                 255

Ser Gln Leu Lys Asp Leu Phe Ala Glu Asp Ala Ser Leu Gly Ser
            260                 265                 270

Arg Glu Leu Ile Ser Ala Val Glu Ala Asn Asn Met Lys Arg Thr Ala
                275                 280                 285

Tyr Asp Val Arg Ala Ser Ala Ala Ile Ala Tyr Gly Asp Pro Tyr Val
290                 295                 300

Tyr Ala Val Gln Pro Gly Met Val Ala Glu Lys Leu Arg Asn Gly Pro
305                 310                 315                 320

Asp Ile Ile Leu Ala Asp His Ala Leu Thr Glu Asp Ala Leu Ala Ile
                325                 330                 335

His Met Ser Ala Val Val Arg Leu Ile Thr Asp Gly Asp Leu Asn Asp
                340                 345                 350

Gly Gly Gly Ala Leu Asp Ala Ala Lys Ala Lys Leu Ser Glu Ser Ala
                355                 360                 365

Arg Arg Ala Trp Gly Ala Val Gln His Ser Ser Pro Arg Gln Leu
370                 375                 380

Leu Glu Ala Leu Ile Glu Arg Gly Phe Val Arg Gln Ala Cys Arg Val
385                 390                 395                 400

Tyr Glu Ser Ala Leu Lys Ala Asn Leu Gly Lys Thr Arg Gly Thr Val
                405                 410                 415

Asn Glu Leu Asp Thr Phe Asp Asp Val Gln Gln Val Ile Gly Asn Ile
                420                 425                 430

Val Phe Gly Leu Met Glu Ser Tyr Gly Pro Gly Met Thr Tyr Leu Thr
            435                 440                 445

Asn Tyr Met Asp Asn Gly Leu Pro Pro Asp Ala Asp Ser Asp Phe Ile
            450                 455                 460

Lys Val Leu Gly Leu Asp Ser Ala Ile Ile Ala Gln Ile Leu Gly Arg
465                 470                 475                 480

Cys Ile Pro Pro Asn Pro His Glu Asp Tyr Val Lys Ser Ala Arg Ala
                485                 490                 495

Ile Leu Ala Ala Glu Met Asp Ser Ala Ile Arg Gln Ser Gly Ala Gly
                500                 505                 510

Thr Ala Asn Arg Ala Ile Gln Phe Ala Lys Glu Ser Leu Met Leu Trp
                515                 520                 525

Phe Asp Ser Arg Ala Glu His Ile Trp Gly Ile
            530                 535

<210> SEQ ID NO 30
<211> LENGTH: 544
<212> TYPE: PRT
<213> ORGANISM: Herpes virus

<400> SEQUENCE: 30

Met Ser Ala Leu Gly Lys Gly Asp Asn Tyr Pro Leu Asn Ala Leu Leu
1               5                   10                  15

Asp Thr Leu Gln Thr Leu Cys Ala Glu Asn Ser Pro Thr Glu Pro Trp
                20                  25                  30
```

-continued

```
Pro Val Thr Val Ile Ser Glu Ala Arg Ala Ile Gly Thr Phe Phe
         35              40              45

Leu Ser Ser Thr Gln Met Ser Ile Gln Gln Val Glu Ser Thr Trp Arg
 50              55                      60

Asp Val Phe Ser Val Ile Leu Glu Val Tyr Gln Arg Thr Lys Ser Pro
 65              70              75                      80

Glu Ala Ala Met Leu Ala Gln Asn Phe Thr Gly Leu Ile Leu Trp Arg
                 85              90                  95

Val Ser Val Arg Trp Asp Lys Thr Ser Trp Arg Asp Glu Ser Ile Arg
             100             105             110

Leu Arg Lys Leu Val Gly Glu Met Thr Gly Glu Glu Pro Ile Thr Trp
         115             120             125

Leu Ser Arg Asn Asn Leu Arg Val Ser Ala Ser Phe Gly Pro Asn Val
     130             135             140

Met Gly Pro Leu Ile Thr Asp Trp Phe Ala Glu Phe Glu Asp Thr Val
145             150             155             160

Thr Ser Ala Val Ser Tyr Thr Pro Glu Cys Leu Leu Ser Glu Arg Glu
                 165             170             175

Arg Ile Pro Asn Val Trp Asn Leu Thr Asp Ser Leu Ala His Lys Arg
             180             185             190

Phe Glu Leu Ile Tyr Asp Phe Pro Phe Val Gln Glu Gly Ile Arg Leu
         195             200             205

Ile Ala Arg Thr Val Gly Trp Val Pro Phe Val Ile Leu Tyr Arg
     210             215             220

Cys Thr Thr Asn Arg Ala Phe Thr Pro Leu Thr Arg Ile Leu Phe Thr
225             230             235             240

Ile Ala Phe Ile Asp Gln Tyr Phe Arg Gly Lys Gly Ala Ser Gln His
                 245             250             255

Ser Val Leu Lys Glu Arg Phe Ala Glu Asp Cys Asn Ala Leu Gly Ser
             260             265             270

Glu Glu Leu Met Ser Ala Ser Gln Ala Asn Leu Thr Lys Arg Thr Ser
         275             280             285

Tyr Glu Val Arg Ala Ser Ala Ala Ile Ala Tyr Gly Asp Pro Phe Ile
     290             295             300

Tyr Gly Ile Gln Pro Gly Met Val Ala Glu Arg Leu Arg Ser Gly Glu
305             310             315             320

Asp Ile Ile Val Ser Ser Thr Ser Leu Thr Glu Asp Ser Leu Ala Ile
                 325             330             335

His Ile Ser Ala Val Leu Gln Leu Ile Ser Ser Asp Gly Ser Asp His
             340             345             350

Ser Thr Ser Val Ile Asp Glu Ala Arg Thr Lys Leu Ser Glu Ser Val
         355             360             365

Arg Arg Ala Trp Asp Ala Ile Gln Tyr Ser Ser Ser Pro Lys Gln Leu
     370             375             380

Leu Glu Ala Leu Ile Asp Asn Gly Phe Val Arg Gln Ser Cys Gln Ala
385             390             395             400

Tyr Glu Ser Ala Leu Lys Thr Tyr Met Ala Lys Asn Tyr Arg Asn Ser
                 405             410             415

Val Glu Thr Ile Phe Asn Asp Leu Gln Gln Val Ile Gly Cys Val Ala
             420             425             430

Val Ile Gly Asn Ile Val Phe Gly Leu Ile Glu Ser Tyr Gly Pro Gly
         435             440             445

Met Asn Tyr Leu Glu Asn Tyr Val Asp Gly Ser Leu Pro Pro Glu Ser
```

```
                450             455             460
Asp Ser Glu Phe Ile Phe Ala Leu Gly Leu Glu His Gly Leu Ile Ser
465                 470                 475                 480

Gln Ile Leu Gly Arg Cys Ile Pro Pro Asp Thr His Asp Asp Tyr Val
                485                 490                 495

Lys Thr Thr Arg Ser Val Leu Leu Ala Glu Met Asp Leu Ile Ala Arg
                500                 505                 510

Lys Met Asp Val Gly Gly Ser Ala Arg Ala Leu Ser Ser Ala Arg Glu
                515                 520                 525

Ser Leu Leu Leu Trp Phe Asp His Arg Ala Glu Val Ile Trp Gly Leu
                530                 535                 540

<210> SEQ ID NO 31
<211> LENGTH: 573
<212> TYPE: PRT
<213> ORGANISM: Herpes virus

<400> SEQUENCE: 31

Met Asp Ser Gly Asp Gln Leu Ser Asp Asn Glu Tyr Tyr Asp Leu Asp
1               5                   10                  15

Glu Asp Asn Thr Cys Ser Asp Asn Arg Ser Pro Arg Pro Val Gly Arg
                20                  25                  30

Trp Leu Leu Lys Asp Met Ile Val Ala Leu Lys Glu Ile Ile Asn Thr
            35                  40                  45

Gln Ser Thr Pro Arg Trp Thr Glu Val Glu Ala Ser Lys Val Lys Ala
        50                  55                  60

Ile Val Ser Thr Phe Cys Leu Ser Gln Glu Gln Met Thr Ile Pro Gln
65                  70                  75                  80

Ile Ser His Ser Trp Lys Glu Ala Phe Asp Leu Leu Leu Val Ala Phe
                85                  90                  95

Ser Asn Thr Gln Thr Pro Glu Val Ala Ile Ile Ile Glu Asn Phe Thr
                100                 105                 110

Gly Leu Val Ile Trp Arg Leu Val Ser Trp Asp Arg Asn Thr Val
            115                 120                 125

Lys Ala Asp Val Thr Lys Leu Met Ala Leu Val Arg Asp Leu Thr Ser
            130                 135                 140

Glu His Val Thr Gln Ser Leu Thr Arg Gln Asn Leu Arg Leu Ser Thr
145                 150                 155                 160

Ser Tyr Gly Val Ser Ala Met Arg Gly Ile Leu Leu Ser Trp Leu Thr
                165                 170                 175

Thr Phe Glu Ala Ala Val Thr Val Leu Ala Thr Thr Pro Asp Val
            180                 185                 190

Leu Leu Asp Ser Glu Arg Leu Gly Phe Arg Lys Asp Arg Val Pro Phe
            195                 200                 205

Thr Ser Arg Tyr Ile Arg Ile Ile Tyr Asp Phe Pro Phe Val Gln Glu
        210                 215                 220

Gly Leu Arg Phe Leu His Arg Asn Ala Asn Trp Met Ile Pro Phe Lys
225                 230                 235                 240

Ile Met Thr Arg Cys Ala Ser Asp Thr Ile Tyr Ser Pro Leu Val Arg
                245                 250                 255

Thr Ile Tyr Thr Ile Ser Leu Val Asp Gln Tyr Phe Trp Gly Ala Gly
            260                 265                 270

Arg Ser Arg Pro Lys Arg Leu Val Asp Gln Phe Val Lys Asp Thr Asp
        275                 280                 285
```

```
Leu Leu Gly Asp Ala Glu Leu Met Ser Pro Gly Ala Asn Ser Thr
    290                 295                 300
Lys Arg Thr Ser Trp Glu Val Arg Leu Ser Ala Ala Leu Ala Tyr Gln
305                 310                 315                 320
Asp Pro Phe Val Arg Glu Val Gln Pro Gly Met Ala Ser Val Arg Val
                325                 330                 335
Arg Thr Ser Pro Asp Met Val Leu Arg Gly Pro Val Phe Gly Pro
                340                 345                 350
Ala Leu Cys Ile His Ser Ala Ala Val Leu Asn Val Ile Ser Gly Ser
            355                 360                 365
Lys Gln Asp Glu Phe Asp Leu Gly Arg Leu Asn Gln Ala Ala Lys Thr
370                 375                 380
Thr Ile Thr Glu Ala Ala Arg Ala Ala Trp Asp Thr Ile Gln His Ser
385                 390                 395                 400
Asn Thr Pro Gln Gln Val Ile Asp Ala Leu Ile Ser Thr Gly Phe Val
                405                 410                 415
Ala Gln Asn Cys Arg Asn Tyr Glu Val Ala Leu Thr Ser Met Tyr Ser
                420                 425                 430
Arg Ala Thr Thr Asp Asn Gly Tyr Ala Leu Asn Asp Thr Gln Gln Val
                435                 440                 445
Ile Gly Cys Val Ser Met Val Gly Asn Val Val Phe Gly Leu Ile Asp
    450                 455                 460
Ser Tyr Gly Arg Asp Ala Asp Tyr Ile Asp Ala Tyr Ala Glu Ala Met
465                 470                 475                 480
Ser Ser Leu Glu Ser Asp Ser Gly Asp Phe Leu Ser Ala Ile Gly Leu
                485                 490                 495
Pro Lys Gly Gly Ile Glu Gln Thr Ile Arg His Cys Met Ala Pro Arg
            500                 505                 510
Pro Ile Thr Asp Tyr Ile Arg Ala Ala Arg Gln Ala Leu Val Gln Glu
            515                 520                 525
Ile Glu Thr Ala Ser Ser Ile Tyr Lys Gly Arg Leu Ser Ser Arg Leu
            530                 535                 540
Gln Thr His His Thr Ser Thr His Asn Ser Val Arg Gly Ser Leu Leu
545                 550                 555                 560
Leu Trp Phe Asp Phe Arg Ala Lys Gln Ile Trp Gly Ile
                565                 570

<210> SEQ ID NO 32
<211> LENGTH: 636
<212> TYPE: PRT
<213> ORGANISM: Herpes virus

<400> SEQUENCE: 32

Met Val Ser Pro Thr Pro Thr Pro Pro Lys Glu Gly Arg Ala Ala
1               5                   10                  15
Thr Pro Pro Lys Glu Gly Arg Ala Ala Thr Pro Pro Arg Asp Asp Arg
                20                  25                  30
Ala Pro Pro Val Pro Lys Asp Asn Thr Ala Ala Thr Pro Ser Asp Asn
            35                  40                  45
Ala Arg Thr Thr Pro Ser Thr Lys Glu Asp Gly Ala Ala Ala Pro Pro
    50                  55                  60
Pro Ala Ala Pro Pro Gly Asp Gly Arg Ala Pro Ser Pro Ser Gly Asn
65                  70                  75                  80
Ser Arg Pro Gly His Pro Thr Asp Gly Pro Leu Gln Ser Leu Leu Gly
                85                  90                  95
```

```
Ala Leu Ala Ser Leu Ala Ala Gly Pro Ala Ser Pro Ala Glu Thr
            100                 105                 110

Pro Arg Asp Ala Asp Glu Asp Ser Val Leu Leu Ala Ala Lys Leu Arg
            115                 120                 125

Ala Ala Ile Ala Ala Phe Leu Leu Ser Thr Ala Pro Ile Arg Val Val
            130                 135                 140

Asp Ala Arg Thr His Trp Arg Pro Leu Leu Glu Arg Leu Cys Asp Leu
145                 150                 155                 160

His Gly Ala His Gly Leu Pro Glu Thr Ala Leu Leu Ala Glu Asn Leu
                165                 170                 175

Pro Gly Leu Leu Ala His Arg Leu Ala Val Ala Leu Pro Asp Asp Pro
            180                 185                 190

Glu Arg Ala Phe Glu Ala Met Asp Asp Leu Lys Ala Gly Val Leu Ala
            195                 200                 205

Thr Thr Ser Pro Glu Ala Thr Arg Leu Leu Glu Ala Ala Gly Leu Arg
210                 215                 220

Thr Ala Ala Leu Gly Pro Ala Arg Thr Arg Gln Cys Val Thr Glu
225                 230                 235                 240

Trp Thr Asp Arg Trp Arg Ser Val Ser Glu Ser Cys Leu Arg Leu Asp
            245                 250                 255

Pro Arg Ala Ala Ser Gly Ala Pro Ala Asp Ala Ser Pro Val Ser
            260                 265                 270

Pro Ile Pro Leu Gly Gln Pro Gly Ala Gly Leu Thr Thr Pro Ala Tyr
            275                 280                 285

Ser Thr Ile Phe Pro Ala Pro Phe Val Gln Glu Gly Leu Arg Phe Leu
            290                 295                 300

Ala Arg Ala Ser Asn Trp Ala Thr Leu Phe Ser Thr His Leu Gln Arg
305                 310                 315                 320

Val Asp Asp Ala Thr Leu Thr Pro Leu Thr Arg Ala Leu Phe Thr Leu
            325                 330                 335

Ala Leu Val Asp Glu Tyr Leu Thr Thr Arg Asp Arg Gly Ile Val Ala
            340                 345                 350

Pro Pro Arg Leu Leu Glu Gln Phe Glu His Thr Val Arg Glu Ile Asp
            355                 360                 365

Pro Ala Ile Met Ile Pro Pro Ile Glu Ala Asn Lys Met Val Arg Thr
            370                 375                 380

Arg Glu Glu Val Arg Val Ser Ala Ala Leu Asn His Leu Thr Pro Arg
385                 390                 395                 400

Ser Ala Arg Ala Pro Pro Gly Thr Leu Met Thr Arg Val Arg Thr Asp
                405                 410                 415

Ala Ala Val Phe Asp Pro Glu Glu Pro Leu Leu Ser Ser Ala Leu
            420                 425                 430

Ala Ile Phe Gln Pro Ala Val Ala Leu Leu Gly Ser Gly Glu Pro
            435                 440                 445

Pro Ser Ala Gly Ala Gln Arg Arg Leu Leu Ala Leu Leu His Gln Thr
            450                 455                 460

Trp Ala Leu Ile Gln Asn Thr Gly Ser Pro Ser Val Val Ile Asn Ala
465                 470                 475                 480

Leu Ile Asp Ala Gly Phe Thr Pro Leu His Cys Ser His Tyr Leu Ser
                485                 490                 495

Ala Leu Glu Gly Phe Leu Ala Thr Gly Gly Ala Ser Arg Gly Leu Ala
            500                 505                 510
```

```
Gly Pro Gly Leu Ser Glu Ile Gln Gln Leu Phe Gly Cys Ile Ala Leu
            515                 520                 525

Thr Gly Ala Asn Val Phe Ala Leu Ala Arg Glu Tyr Gly Tyr His Ser
530                 535                 540

Gly Tyr Val Arg Ala Phe Arg Arg Ile Gln Asp Ala Cys Glu Lys Ala
545                 550                 555                 560

His Ala Arg Leu Cys Glu Ala Ala Gly Leu Thr Gly Val Leu Ser
                565                 570                 575

Gln Thr Leu Ala Arg Val Met Gly Pro Val Thr Pro Thr Glu His Leu
            580                 585                 590

Ala Ser Leu Arg Arg Ala Leu Val Gly Glu Phe Glu Ser Ala Glu Arg
595                 600                 605

Arg Phe Gly Ala Gly Arg Ala Ser Pro Leu Arg Glu Thr Val Leu Ile
    610                 615                 620

Trp Val Asp Val Tyr Gly Gln Thr Glu Trp Asp Ile
625                 630                 635

<210> SEQ ID NO 33
<211> LENGTH: 655
<212> TYPE: PRT
<213> ORGANISM: Herpes virus

<400> SEQUENCE: 33

Met Val Ser Pro Thr Pro Thr Pro Pro Thr Glu Glu Asn Arg Ser Arg
1               5                   10                  15

Pro Ala Pro Pro Lys Glu Ala Arg Gly Ser Ala Ala Thr Ser Pro
            20                  25                  30

Lys Glu Thr Arg Ser Arg Thr Thr Pro Pro Lys Glu Ala Arg Gly
        35                  40                  45

Ser Ala Ala Thr Ser Pro Glu Asn Val Arg Thr Ala Pro Ala Pro Gly
    50                  55                  60

Asp Thr Arg Ala Ala Ala Pro Pro Thr Pro Glu Glu Thr Arg Ala Pro
65                  70                  75                  80

Pro Pro Pro Ala Thr Pro Pro Glu Asp Val Arg Ala Ala Thr Pro Ser
                85                  90                  95

Gly Asp Ala Arg Leu Gly Pro Pro Asp Gly Pro Leu Gln Ser Leu
            100                 105                 110

Leu Gly Ala Leu Thr Ser Leu Ala Thr Ala Arg Pro Ala Pro Pro Thr
        115                 120                 125

Glu Ala Ser Gly Glu Ala Gly Glu Asp Ala Val Leu Leu Ala Ala Arg
130                 135                 140

Leu Arg Ala Ala Ile Ala Ala Phe Leu Leu Ser Gly Ala Pro Ile Arg
145                 150                 155                 160

Val Ala Asp Ala Arg Thr His Trp Arg Pro Leu Leu Glu Arg Leu Cys
                165                 170                 175

Ala Leu His Gly Ala His Gly Leu Pro Glu Thr Ala Leu Leu Ala Glu
            180                 185                 190

Asn Leu Pro Gly Leu Leu Ala His Arg Leu Ala Val Ala Leu Pro Asp
        195                 200                 205

Ala Pro Asp Arg Ala Phe Glu Ala Met Asp His Leu Arg Ala Ala Val
210                 215                 220

Leu Asp Ala Ala Ser Pro Glu Ala Thr Arg Leu Leu Glu Ala Ala Gly
225                 230                 235                 240

Leu Arg Thr Ala Ala Ala Leu Gly Pro Ala Arg Thr Arg Gln Cys Val
                245                 250                 255
```

-continued

```
Ala Glu Trp Thr Asp Arg Trp Arg Ser Val Thr Glu Ser Cys Leu Arg
            260                 265                 270

Leu Asp Pro Arg Ala Ser Ser Ala Pro Gly Gly Ala Asp Pro Pro
            275                 280                 285

Val Ser Pro Val Pro Leu Gly Gln Pro Ser Ala Gly Leu Ala Thr Pro
290                 295                 300

Ala Tyr Ser Pro Ile Phe Pro Ala Pro Phe Val Gln Glu Gly Leu Arg
305                 310                 315                 320

Phe Leu Ala Arg Ala Ser Asn Trp Ala Thr Leu Phe Ser Thr His Leu
                325                 330                 335

Gln Ser Val Asp Asp Ala Thr Leu Thr Pro Leu Thr Arg Ala Leu Phe
            340                 345                 350

Thr Leu Ser Leu Val Asp Glu Tyr Leu Thr Thr Arg Asp Arg Gly Ile
            355                 360                 365

Val Ala Pro Pro Arg Leu Leu Glu Gln Phe Glu Arg Thr Val Arg Glu
370                 375                 380

Ile Asp Pro Ala Ile Met Ile Pro Pro Ile Glu Ala Asn Lys Met Val
385                 390                 395                 400

Arg Ser Arg Glu Glu Val Arg Val Ser Ala Ala Leu Asn His Leu Thr
                405                 410                 415

Pro Arg Ser Ala Arg Ala Pro Pro Gly Thr Leu Met Ser Arg Val Arg
            420                 425                 430

Thr Asp Ala Ala Val Phe Asp Pro Glu Glu Pro Phe Leu Ser Ala Ser
            435                 440                 445

Ala Leu Ala Ile Phe Gln Pro Ala Val Ala Ala Leu Leu Gly Ser Gly
        450                 455                 460

Glu Pro Pro Ser Ala Gly Ala Gln Arg Arg Leu Leu Ala Leu Leu His
465                 470                 475                 480

Gln Thr Trp Ala Leu Ile Gln Asn Thr Gly Ser Pro Ser Val Val Ile
                485                 490                 495

Asn Ala Leu Ile Asp Ala Gly Phe Thr Pro Leu His Cys Ser His Tyr
            500                 505                 510

Leu Ser Ala Leu Glu Gly Phe Leu Ala Ala Gly Gly Ala Ala Arg Gly
            515                 520                 525

Leu Ala Gly Pro Pro Ala Leu Ser Glu Val Gln Gln Leu Phe Gly Cys
530                 535                 540

Val Ala Leu Thr Gly Ala Asn Val Phe Ala Leu Ala Arg Glu Tyr Gly
545                 550                 555                 560

Tyr His Ser Gly Tyr Val Arg Ala Phe Arg Val Gln Asp Ala Cys
                565                 570                 575

Glu Gln Ala His Ala Arg Leu Cys Glu Ala Ala Gly Leu Ala Gly Gly
            580                 585                 590

Val Leu Ser Gln Thr Leu Ala Arg Val Met Gly Pro Val Thr Pro Thr
            595                 600                 605

Glu His Leu Ala Ser Leu Arg Arg Ala Leu Val Gly Glu Phe Glu Ser
        610                 615                 620

Ala Glu Arg Arg Phe Gly Ala Gly Arg Pro Ser Pro Leu Arg Glu Thr
625                 630                 635                 640

Val Leu Ile Trp Ile Asp Val Tyr Gly Gln Thr Glu Trp Asp Ile
                645                 650                 655
```

<210> SEQ ID NO 34
<211> LENGTH: 570

<212> TYPE: PRT
<213> ORGANISM: Herpes virus

<400> SEQUENCE: 34

```
Met Ser Asp Ser Ala Leu Gln Val Pro Ala Gly Met Thr Pro
 1               5                  10                  15

Pro Ser Ala Pro Pro Asn Gly Pro Leu Gln Val Leu Leu Gly Ser
            20                  25                  30

Leu Thr Asn Leu Arg Arg Pro Pro Ser Pro Ser Ser Glu Pro Ala Gly
        35                  40                  45

Ser Ala Asp Glu Pro Ala Phe Leu Ser Ala Ala Lys Leu His Ala Ala
    50                  55                  60

Thr Ala Ala Phe Leu Leu Ser Gly Ala Ala Val Gly Pro Ala Glu Ala
65                  70                  75                  80

Arg Ala Cys Trp His Pro Leu Leu Glu Gln Leu Cys Ala Leu His Arg
                85                  90                  95

Ala His Gly Leu Pro Glu Thr Ala Leu Leu Ala Glu Asn Leu Pro Gly
            100                 105                 110

Leu Leu Val His Arg Met Ala Val Ala Leu Pro Glu Thr Pro Glu Ala
        115                 120                 125

Ala Phe Arg Glu Met Asp Val Ile Lys Asp Thr Val Leu Ala Ile Thr
    130                 135                 140

Gly Ser Asp Thr Thr His Ala Leu Glu Ala Ala Gly Leu Arg Thr Thr
145                 150                 155                 160

Ala Ala Leu Gly Pro Val Arg Val Arg Gln Cys Ala Val Glu Trp Ile
                165                 170                 175

Asp Arg Trp Arg Thr Val Thr Gln Ser Cys Leu Ala Met Asn Pro Arg
            180                 185                 190

Thr Ser Leu Glu Ala Leu Gly Glu Met Ser Leu Lys Met Ser Pro Val
        195                 200                 205

Pro Leu Gly Gln Pro Gly Ala Asn Leu Thr Thr Pro Ala Tyr Ser Leu
    210                 215                 220

Leu Phe Pro Ser Pro Ile Val Gln Glu Gly Leu Arg Phe Leu Ala Leu
225                 230                 235                 240

Val Ser Asn Trp Val Thr Leu Phe Ser Ala His Leu Gln Arg Ile Asp
                245                 250                 255

Asp Ala Ala Leu Thr Pro Leu Thr Arg Ala Leu Phe Thr Leu Ala Leu
            260                 265                 270

Val Asp Asp Tyr Leu Thr Thr Pro Asp Arg Gly Ala Val Val Pro Pro
        275                 280                 285

Pro Leu Leu Ala Gln Phe Gln His Thr Val Arg Glu Ile Asp Pro Ala
    290                 295                 300

Ile Met Ile Pro Pro Leu Glu Ala Thr Lys Met Val Arg Ser Arg Glu
305                 310                 315                 320

Glu Val Arg Val Ser Thr Ala Leu Ser Arg Val Ser Pro Arg Ser Ala
                325                 330                 335

Cys Ala Pro Pro Gly Thr Leu Met Ala Arg Val Arg Thr Asp Ala Ala
            340                 345                 350

Val Phe Asp Pro Asp Val Pro Phe Leu Ser Ala Ser Ala Leu Ala Ile
        355                 360                 365

Phe Arg Pro Ala Val Thr Gly Leu Leu Gln Leu Gly Glu Pro Pro Ser
    370                 375                 380

Ala Gly Ala Gln Gln Arg Leu Leu Ala Leu Leu Gln Gln Thr Trp Ala
385                 390                 395                 400
```

Leu Val Gln Asn Ser Asn Ser Pro Ser Val Val Ile Asn Thr Leu Thr
            405                 410                 415

Asp Ala Gly Phe Thr Pro Ala His Cys Thr Gln Tyr Ile Ser Ala Leu
            420                 425                 430

Glu Gly Phe Leu Val Ala Gly Val Pro Ala Arg Thr Pro Pro Gly His
            435                 440                 445

Gly Leu Ser Glu Ile Gln Gln Leu Phe Gly Cys Ile Ala Leu Ala Gly
            450                 455                 460

Ala Asn Val Phe Gly Leu Ala Arg Glu Tyr Gly His Tyr Ala Gly Tyr
465                 470                 475                 480

Val Lys Thr Phe Arg Arg Ile Gln Gly Ala Ser Glu His Thr His Gly
            485                 490                 495

Arg Leu Cys Glu Ala Val Gly Leu Ser Gly Gly Val Leu Ser Gln Thr
            500                 505                 510

Leu Ala Arg Ile Met Gly Pro Ala Val Pro Thr Glu His Leu Ala Ser
            515                 520                 525

Leu Arg Arg Thr Leu Val Gly Glu Phe Glu Thr Ala Glu Arg Arg Phe
            530                 535                 540

Ser Ala Gly Gln Pro Ser Leu Leu Arg Glu Thr Ala Leu Ile Trp Leu
545                 550                 555                 560

Asp Val Tyr Gly Gln Thr His Trp Asp Leu
            565                 570

<210> SEQ ID NO 35
<211> LENGTH: 570
<212> TYPE: PRT
<213> ORGANISM: Herpes virus

<400> SEQUENCE: 35

Met Ala Asp Arg Gly Leu Pro Ser Glu Ala Pro Val Val Thr Thr Ser
1               5                   10                  15

Pro Ala Gly Pro Pro Ser Asp Gly Pro Met Gln Arg Leu Leu Ala Ser
            20                  25                  30

Leu Ala Gly Leu Arg Gln Pro Pro Thr Pro Thr Ala Glu Thr Ala Asn
        35                  40                  45

Gly Ala Asp Asp Pro Ala Phe Leu Ala Thr Ala Lys Leu Arg Ala Ala
    50                  55                  60

Met Ala Ala Phe Leu Leu Ser Gly Thr Ala Ile Ala Pro Ala Asp Ala
65                  70                  75                  80

Arg Asp Cys Trp Arg Pro Leu Leu Glu His Leu Cys Ala Leu His Arg
                85                  90                  95

Ala His Gly Leu Pro Glu Thr Ala Leu Leu Ala Glu Asn Leu Pro Gly
            100                 105                 110

Leu Leu Val His Arg Leu Val Val Ala Leu Pro Glu Ala Pro Asp Gln
        115                 120                 125

Ala Phe Arg Glu Met Glu Val Ile Lys Asp Thr Ile Leu Ala Val Thr
    130                 135                 140

Gly Ser Asp Thr Ser His Ala Leu Asp Ser Ala Gly Leu Arg Thr Ala
145                 150                 155                 160

Ala Ala Leu Gly Pro Val Arg Val Arg Gln Cys Ala Val Glu Trp Ile
                165                 170                 175

Asp Arg Trp Gln Thr Val Thr Lys Ser Cys Leu Ala Met Ser Pro Arg
            180                 185                 190

Thr Ser Ile Glu Ala Leu Gly Glu Thr Ser Leu Lys Met Ala Pro Val 195                 200                 205

Pro Leu Gly Gln Pro Ser Ala Asn Leu Thr Thr Pro Ala Tyr Ser Leu
210                 215                 220

Leu Phe Pro Ala Pro Phe Val Gln Glu Gly Leu Arg Phe Leu Ala Leu
225                 230                 235                 240

Val Ser Asn Arg Val Thr Leu Phe Ser Ala His Leu Gln Arg Ile Asp
                245                 250                 255

Asp Ala Thr Leu Thr Pro Leu Thr Arg Ala Leu Phe Thr Leu Ala Leu
                260                 265                 270

Val Asp Glu Tyr Leu Thr Thr Pro Glu Arg Gly Ala Val Pro Pro
            275                 280                 285

Pro Leu Leu Ala Gln Phe Gln His Thr Val Arg Glu Ile Asp Pro Ala
290                 295                 300

Ile Met Ile Pro Pro Leu Glu Ala Asn Lys Met Val Arg Ser Arg Glu
305                 310                 315                 320

Glu Val Arg Val Ser Thr Ala Leu Ser Arg Val Ser Pro Arg Ser Ala
                325                 330                 335

Cys Ala Pro Pro Gly Thr Leu Met Ala Arg Val Arg Thr Asp Val Ala
                340                 345                 350

Val Phe Asp Pro Asp Val Pro Phe Leu Ser Ser Ala Leu Ala Val
            355                 360                 365

Phe Gln Pro Ala Val Ser Ser Leu Leu Gln Leu Gly Glu Gln Pro Ser
370                 375                 380

Ala Gly Ala Gln Gln Arg Leu Leu Ala Leu Gln Gln Thr Trp Thr
385                 390                 395                 400

Leu Ile Gln Asn Thr Asn Ser Pro Ser Val Val Ile Asn Thr Leu Ile
                405                 410                 415

Asp Ala Gly Phe Thr Pro Ser His Cys Thr His Tyr Leu Ser Ala Leu
                420                 425                 430

Glu Gly Phe Leu Ala Ala Gly Val Pro Ala Arg Thr Pro Thr Gly His
            435                 440                 445

Gly Leu Gly Glu Val Gln Gln Leu Phe Gly Cys Ile Ala Leu Ala Gly
450                 455                 460

Ser Asn Val Phe Gly Leu Ala Arg Glu Tyr Gly Tyr Ala Asn Tyr
465                 470                 475                 480

Val Lys Thr Phe Arg Arg Val Gln Gly Ala Ser Glu His Thr His Gly
                485                 490                 495

Arg Leu Cys Glu Ala Val Gly Leu Ser Gly Val Leu Ser Gln Thr
            500                 505                 510

Leu Ala Arg Ile Met Gly Pro Ala Val Pro Thr Glu His Leu Ala Ser
            515                 520                 525

Leu Arg Arg Ala Leu Val Gly Glu Phe Glu Thr Ala Glu Arg Arg Phe
530                 535                 540

Ser Ser Gly Gln Pro Ser Leu Leu Arg Glu Thr Ala Leu Ile Trp Ile
545                 550                 555                 560

Asp Val Tyr Gly Gln Thr His Trp Asp Ile
            565                 570

<210> SEQ ID NO 36
<211> LENGTH: 612
<212> TYPE: PRT
<213> ORGANISM: Herpesvirus saimiri

<400> SEQUENCE: 36

```
Met Thr Gln Ala Thr Arg Thr Arg Val Pro Val Glu Trp His Glu Leu
1               5                   10                  15

Ile Ala Ala Ala Glu Asn Asp Leu Arg Glu His Ala Pro Ala Pro Ser
                20                  25                  30

His Val Gly Ser Ile Trp Asn Leu Val Asp Thr Leu Glu Pro Leu Ala
            35                  40                  45

Thr Gln Leu Arg Glu Met Ser Arg Ala Ala Thr Ala Ala Ala Pro Pro
        50                  55                  60

Arg Leu Ser Pro Gly Ala Gly Arg Lys Leu Val Gly His Gly Ser
65                  70                  75                  80

Ala Tyr Pro Pro Glu Gln Thr Phe Leu Leu Val Ala Arg Leu Arg Ala
                85                  90                  95

Ala Phe Ala Ser Phe Leu Leu Ala Pro Thr Ala Ala Pro Glu His
                100                 105                 110

Val Arg Ser Gly Trp Pro Arg Leu Ile Ser Leu Leu Cys Glu Leu His
            115                 120                 125

Arg Gly Leu Ser Leu Thr Glu Thr Ala Leu Leu Glu Asn Leu Pro
        130                 135                 140

Gly Leu Ala Val His His Ile Asp Val Ala Val Pro Arg Asp Arg Ala
145                 150                 155                 160

Gly Ala Cys Arg Asp Met Ser Ala Val Ile Ala Cys Val Arg Lys Met
                165                 170                 175

Ala Gly Pro Glu Thr Val Asp Ala Leu Glu Glu Leu Gly Leu Arg Thr
                180                 185                 190

Ser Ser Pro Leu Gly Pro Ile Ser Thr Gln Arg Asn Val Leu Asp Trp
            195                 200                 205

Val Gln Arg Trp Leu Ala Val Thr Lys Ser Met His Glu Ala Asp Pro
210                 215                 220

Arg Glu Ser Ala Asp Phe Ser Ser Ala Pro Pro Leu Lys Asn Leu Ala
225                 230                 235                 240

Thr Leu Pro Leu Gly Gln Pro Gly Ala Gly Leu Ala Ala Pro Lys Tyr
                245                 250                 255

His Leu Ile Phe Gly Ala Pro Phe Val Gln Arg Gly Leu Arg His Leu
            260                 265                 270

Ala Glu Val Gly Asn Arg Val Cys Val Val Gly Ala Tyr Leu Arg Arg
        275                 280                 285

Ala Asp Asp Ala Ala Leu Thr Pro Leu Ala Arg Ala Leu Phe Thr Leu
    290                 295                 300

Ala Leu Val Asp Glu His Val Pro Ser Gly Gly Val Pro Ser Leu
305                 310                 315                 320

Leu Val Gln Arg Phe Arg Arg Asp Val Ala Leu Val Asp Pro Thr Ile
                325                 330                 335

Met Ile Pro Pro Leu Glu Ala Asn Pro Met Pro Arg Thr Arg Gly Glu
                340                 345                 350

Val Arg Ile Ser Ser Ala Leu Ser Thr Arg Thr Pro Gly Val Thr Cys
            355                 360                 365

Ala Pro Pro Gly Thr Leu Ile Thr Arg Val Arg Thr Asp Ser Asp Val
    370                 375                 380

Phe Gly Thr His Pro Glu His Val Ser Ala Ala Leu Ala Val Phe
385                 390                 395                 400

Gln Pro Ala Val Ser Ser Leu Leu Gln Ala Gly Glu Thr Glu Ala Thr
                405                 410                 415

Pro Glu Val Arg Gln Arg Met Leu Gly Leu Leu His Glu Thr Trp Ala
```

-continued

```
                    420               425               430
Arg Leu Gln Asn Thr Thr Ser Ala Asp Val Ala Leu Ala Thr Leu Val
            435               440               445

Asp Ala Gly Phe Thr Pro Ala Asn Cys Ala Ala Tyr Leu Ser Ala Leu
        450               455               460

Glu Gly Phe Leu Ala Ser Gly His Leu Val Ala Ser Ala Asp Ser Gly
465               470               475               480

Glu Lys Asp Ala Arg Gly Leu Asp Gly Arg Glu Leu Gly Glu Ile Gln
                485               490               495

Gln Leu Phe Gly Cys Ile Ser Ile Leu Gly Arg Gly Ile Phe Gln Leu
            500               505               510

Ala Arg Glu Tyr Gly Pro His Ala Glu Tyr Val Lys Thr Phe Lys Arg
        515               520               525

Ile Gln Ala Ala Cys Glu Gln Arg His Ala Gln Leu Ser His Ala Ala
            530               535               540

Gly Leu Ser Gln Gly Val Leu Gly Gln Ala Leu Ala Arg Ile Met Ser
545               550               555               560

Pro Thr Thr Pro Thr Glu His Leu Ala Ala Leu Arg Arg Ala Leu Val
                565               570               575

Asp Glu Phe Glu Val Ala Glu Arg Arg Phe Asn Glu Gly His Pro Ser
            580               585               590

Leu Leu Arg Glu Pro Val Met Ala Trp Val Asp Ile Tyr Gly Gln Thr
        595               600               605

Ala Trp Asp Val
        610
```